US011426499B2

(12) United States Patent
Bartlett et al.

(10) Patent No.: US 11,426,499 B2
(45) Date of Patent: Aug. 30, 2022

(54) BREAST PUMPS

(71) Applicant: LANSINOH LABORATORIES, INC., Alexandria, VA (US)

(72) Inventors: Rush Bartlett, Austin, TX (US); Mahmut Melih Kavurka, Izmir (TR); Hasan Keser, Izmir (TR); Faik Koklu, Izmir (TR); Gokhan Onur, Izmir (TR); Peter Lawrence Visconti, Gurnee, IL (US); Frank Tinghwa Wang, Taipei (TW)

(73) Assignee: Lansinoh Laboratories, Inc., Alexandria, VA (US)

( * ) Notice: Subject to any disclaimer, the term of this patent is extended or adjusted under 35 U.S.C. 154(b) by 139 days.

(21) Appl. No.: 16/563,097

(22) Filed: Sep. 6, 2019

(65) Prior Publication Data

US 2020/0078502 A1 Mar. 12, 2020

Related U.S. Application Data

(60) Provisional application No. 62/756,370, filed on Nov. 6, 2018, provisional application No. 62/727,897, filed on Sep. 6, 2018.

(51) Int. Cl.
*A61M 1/06* (2006.01)
*A61M 1/00* (2006.01)

(52) U.S. Cl.
CPC ............ *A61M 1/06* (2013.01); *A61M 1/80* (2021.05); *A61M 2205/16* (2013.01); *A61M 2205/3331* (2013.01); *A61M 2205/502* (2013.01)

(58) Field of Classification Search
None
See application file for complete search history.

(56) References Cited

U.S. PATENT DOCUMENTS 2,301,781 A * 11/1942 Higbee ............... A61J 19/00
604/245
3,911,920 A 10/1975 Susinn
(Continued)

FOREIGN PATENT DOCUMENTS

| EP | 0000339 | 1/1979 |
| JP | 2003299727 | 10/2003 |
| WO | WO2014143130 | 9/2014 |

OTHER PUBLICATIONS

"Elvie Pump" Elvie.com [online]. Retrieved from the Internet: <URL: https://www.elvie.com/shop/elvie-pump>, 12 pages. Retrieved on Sep. 3, 2019.

(Continued)

*Primary Examiner* — Nathan R Price
*Assistant Examiner* — Weng Lee
(74) *Attorney, Agent, or Firm* — Merchant & Gould P.C.

(57) ABSTRACT

An example breast pump system can include: a control unit including a processor and memory, the control unit including an interface to control the breast pump system; a vacuum unit controlled by the control unit, the vacuum unit including pump motors to create suction for pumping milk; a support mechanism located remotely from the control unit; and a member extending between the control unit and the support mechanism, the member being movable to allow the control unit to be repositioned relative to the support mechanism. The memory encodes instructions which, when executed by the processor, cause the breast pump system to: select at least a first pump motor from the plurality of pump motors for a first pumping timeframe; and select at least a second pump motor from the plurality of pump motors for a second pumping timeframe.

15 Claims, 63 Drawing Sheets

(56) References Cited

U.S. PATENT DOCUMENTS

| | | | |
|---|---|---|---|
| 4,263,912 A | 4/1981 | Adams | |
| 4,323,067 A | 4/1982 | Adams | |
| 4,673,388 A | 6/1987 | Schlensog et al. | |
| 4,799,922 A | 1/1989 | Beer | |
| 4,856,663 A | 8/1989 | Epp | |
| 4,857,051 A | 8/1989 | Larsson | |
| 4,884,013 A | 11/1989 | Jackson | |
| 4,930,652 A | 6/1990 | Murphy | |
| 4,961,726 A | 10/1990 | Richter | |
| 4,964,851 A | 10/1990 | Larsson | |
| 4,966,580 A | 10/1990 | Turner | |
| 5,531,338 A | 7/1996 | Sklar | |
| 5,542,921 A | 8/1996 | Meyers | |
| 5,656,026 A | 8/1997 | Joseph | |
| 5,728,137 A | 3/1998 | Anderson | |
| 5,810,772 A | 9/1998 | Niederberger | |
| 5,941,847 A | 8/1999 | Huber | |
| 5,957,081 A | 9/1999 | van der Lely | |
| RE36,324 E | 10/1999 | Yoda | |
| 6,023,639 A | 2/2000 | Hakky | |
| 6,110,140 A | 8/2000 | Silver | |
| 6,200,295 B1 | 3/2001 | Burchett | |
| 6,461,324 B1 | 10/2002 | Schlensog | |
| 6,471,660 B1 | 10/2002 | Covington | |
| 6,497,677 B2 | 12/2002 | Silver | |
| 6,884,229 B2 | 4/2005 | Renz | |
| 6,966,904 B2 | 11/2005 | Ruth | |
| 7,029,454 B2 | 4/2006 | Watanabe | |
| 7,048,120 B2 | 5/2006 | Pond | |
| 7,294,120 B1 | 11/2007 | Eidsen et al. | |
| 7,320,678 B2 | 1/2008 | Ruth | |
| 7,413,557 B2 | 8/2008 | Samson et al. | |
| 7,648,467 B2 | 1/2010 | Wang | |
| 7,662,127 B2 | 2/2010 | Silver | |
| 7,875,000 B2 | 1/2011 | Krebs | |
| 8,052,635 B1 | 11/2011 | Kelly | |
| 8,360,102 B2 | 1/2013 | Khouri | |
| 8,444,596 B2 | 5/2013 | Paterson | |
| 8,545,438 B2 | 10/2013 | Kazazoglu | |
| 8,961,454 B2 | 2/2015 | Chen | |
| 8,979,819 B2 | 3/2015 | Sherman | |
| 8,998,879 B2 | 4/2015 | Sherman | |
| 9,248,077 B1 | 2/2016 | Kelly | |
| 9,539,376 B2 | 1/2017 | Makower | |
| 9,539,377 B2 | 1/2017 | Makower | |
| 9,616,156 B2 | 4/2017 | Alvarez | |
| 9,623,160 B2 | 4/2017 | Alvarez | |
| 9,642,952 B1 | 5/2017 | Kelly | |
| 9,782,526 B2 | 10/2017 | Sherman | |
| D809,646 S | 2/2018 | Mason | |
| D811,579 S | 2/2018 | Chang | |
| D828,542 S | 9/2018 | Mason | |
| 10,080,825 B2 | 9/2018 | Bartlett | |
| 10,086,120 B2 | 10/2018 | Bartlett | |
| 10,105,474 B2 | 10/2018 | Barral | |
| D832,995 S | 11/2018 | Mason | |
| D834,177 S | 11/2018 | Chang | |
| 10,857,271 B2 | 12/2020 | Bartlett et al. | |
| 2002/0072701 A1 | 6/2002 | Nuesch | |
| 2002/0156419 A1 | 10/2002 | Silver | |
| 2004/0178162 A1 | 9/2004 | Zucker-Franklin | |
| 2005/0234400 A1* | 10/2005 | Onuki | A61M 1/06 604/74 |
| 2006/0025718 A1 | 2/2006 | Ostrowski | |
| 2007/0118078 A1 | 5/2007 | McNally | |
| 2007/0135761 A1* | 6/2007 | Cheng | A61M 1/066 604/74 |
| 2007/0235405 A1 | 10/2007 | Fatema | |
| 2008/0021380 A1* | 1/2008 | Thommen | A61M 1/06 604/74 |
| 2008/0039778 A1 | 2/2008 | Goldie | |
| 2008/0177224 A1 | 7/2008 | Kelly et al. | |
| 2008/0255503 A1 | 10/2008 | Quackenbush | |
| 2009/0227943 A1 | 9/2009 | Schultz | |
| 2009/0254028 A1 | 10/2009 | Brittner | |
| 2010/0016789 A1* | 1/2010 | Bosshard | A61M 1/06 604/74 |
| 2010/0049122 A1 | 2/2010 | Jaeger-Waldau | |
| 2010/0324477 A1 | 12/2010 | Paterson | |
| 2011/0054436 A1 | 3/2011 | Griffis | |
| 2011/0168292 A1 | 7/2011 | Luzbetak | |
| 2011/0251552 A1 | 10/2011 | Brittner | |
| 2012/0232524 A1 | 9/2012 | Hyun | |
| 2012/0265169 A1 | 10/2012 | Sherman | |
| 2013/0005023 A1 | 1/2013 | Min | |
| 2013/0030379 A1 | 1/2013 | Ingram | |
| 2013/0281983 A1 | 10/2013 | Sherman | |
| 2014/0031744 A1* | 1/2014 | Chen | A61M 1/066 604/74 |
| 2014/0052106 A1 | 2/2014 | Sherman | |
| 2014/0135683 A1 | 5/2014 | Hradisky | |
| 2014/0180205 A1 | 6/2014 | Lee | |
| 2014/0276629 A1 | 9/2014 | Bauer | |
| 2014/0288466 A1 | 9/2014 | Alvarez | |
| 2015/0133894 A1 | 5/2015 | Sherman | |
| 2015/0283311 A1 | 10/2015 | Alvarez | |
| 2016/0038662 A1 | 2/2016 | Felber | |
| 2016/0082165 A1 | 3/2016 | Alvarez et al. | |
| 2016/0100888 A1* | 4/2016 | Ferrari | A61M 1/062 312/401 |
| 2016/0296681 A1 | 10/2016 | Gaskin et al. | |
| 2016/0331675 A1 | 11/2016 | Dann | |
| 2017/0065753 A1* | 3/2017 | Nowroozi | A61M 1/062 |
| 2017/0072118 A1* | 3/2017 | Makower | A61M 1/062 |
| 2017/0095600 A1 | 4/2017 | Sherman | |
| 2018/0110906 A1 | 4/2018 | Barack | |
| 2018/0193559 A1 | 7/2018 | Hirata et al. | |
| 2018/0361040 A1 | 12/2018 | O'Toole et al. | |
| 2018/0369464 A1 | 12/2018 | Aalders et al. | |

OTHER PUBLICATIONS

"Medela Launches SonataTM Nationwide and Redefines the Breast Pump," Medelabreastfeedingus.com [online] Retrieved from the Internet: <URL: http://www.medelabreastfeedingus.com/media-center/271/medela-launches-sonata-nationwide-and-redefin>, 4 pages, Jan. 3, 2017.

Bartlett et al., "Closed Loop Electric Breast Pump," U.S. Appl. No. 62/727,880, filed Sep. 6, 2018, 32 pages.

Bartlett et al., "Vibratory Waveform for Breast Pump," U.S. Appl. No. 62/727,909, filed Sep. 6, 2018, 25 pages.

Kent et al., "Importance of Vacuum for Breastmilk Expression," Breastfeed. Med., 3(1):11-19, Mar. 2008.

Mitoulas et al., "Effect of vacuum Profile on Breast Milk Expression Using an Electric Breast Pump," J. Hum. Lact. 18(4): 353-360, Nov. 2002.

Sumiko et al, 変動リズムを含む 吸引によるさく乳 の特徴(第1報)排乳量の時間的変化 と母親使用感 会議録 [Study of Breast Pump Suction with Variable Rhythm Temporal Change in Breast Milk Flow and Mothers' Feelings] Japanese Journal of Maternal Health, 59(3):247, 2018 [Poster with English annotations].

International Search Report and Written Opinion in PCT/US2019/049959 dated Jan. 31, 2020, 17 pages.

* cited by examiner

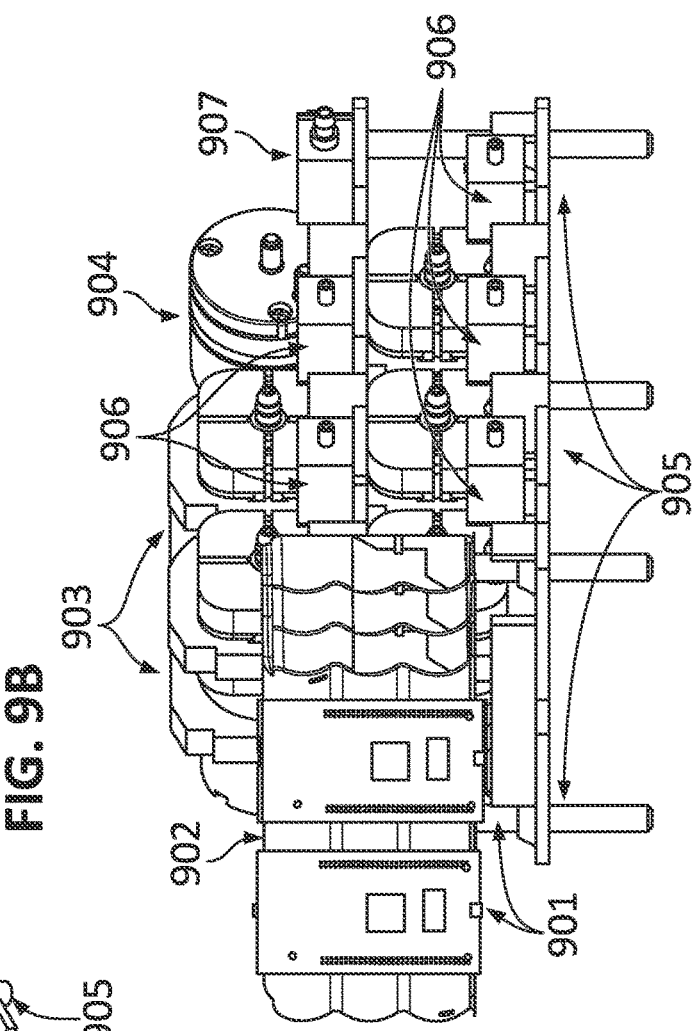
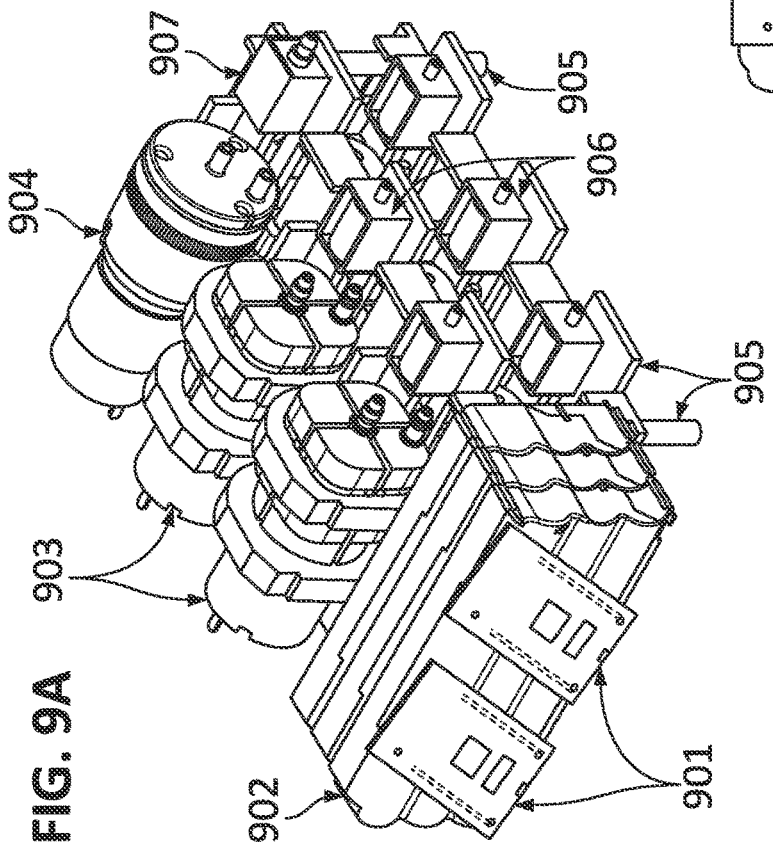
FIG. 9A
FIG. 9B

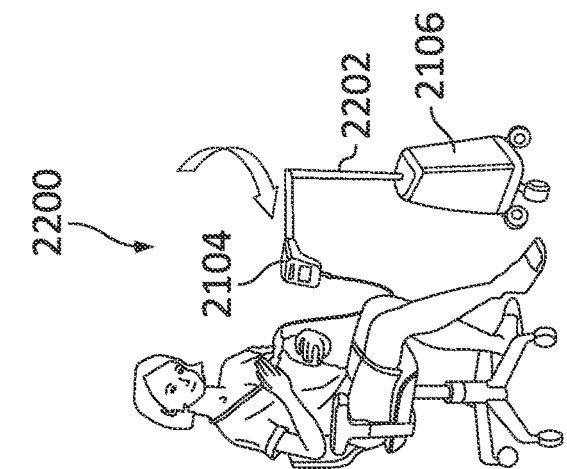
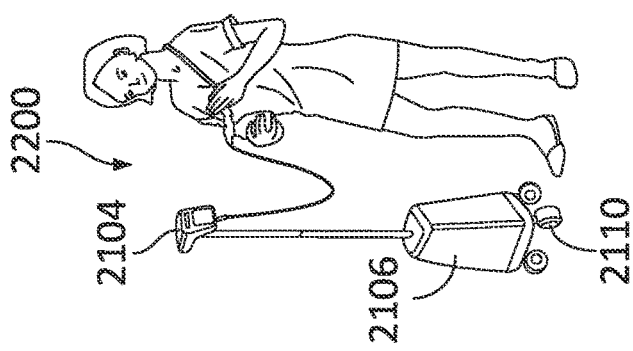
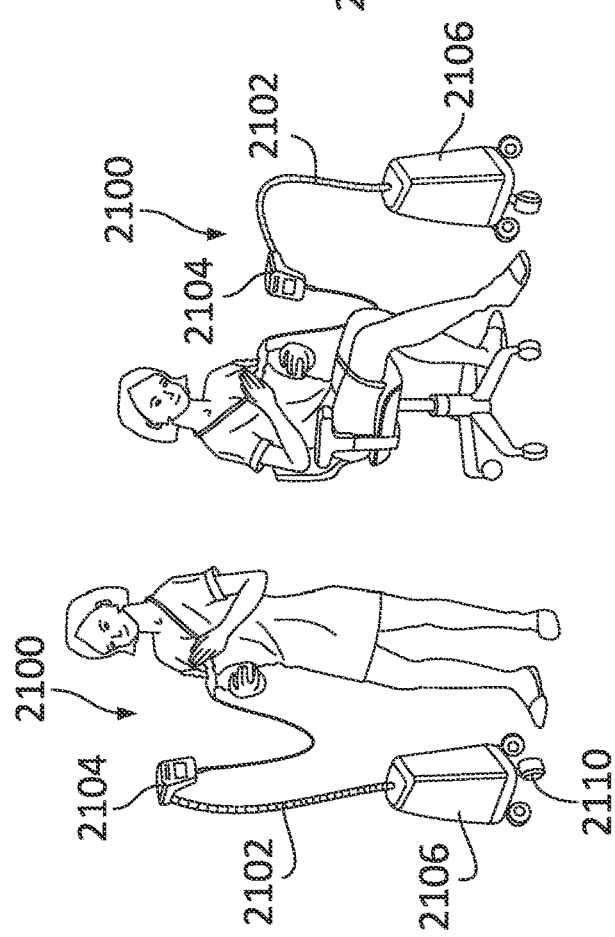

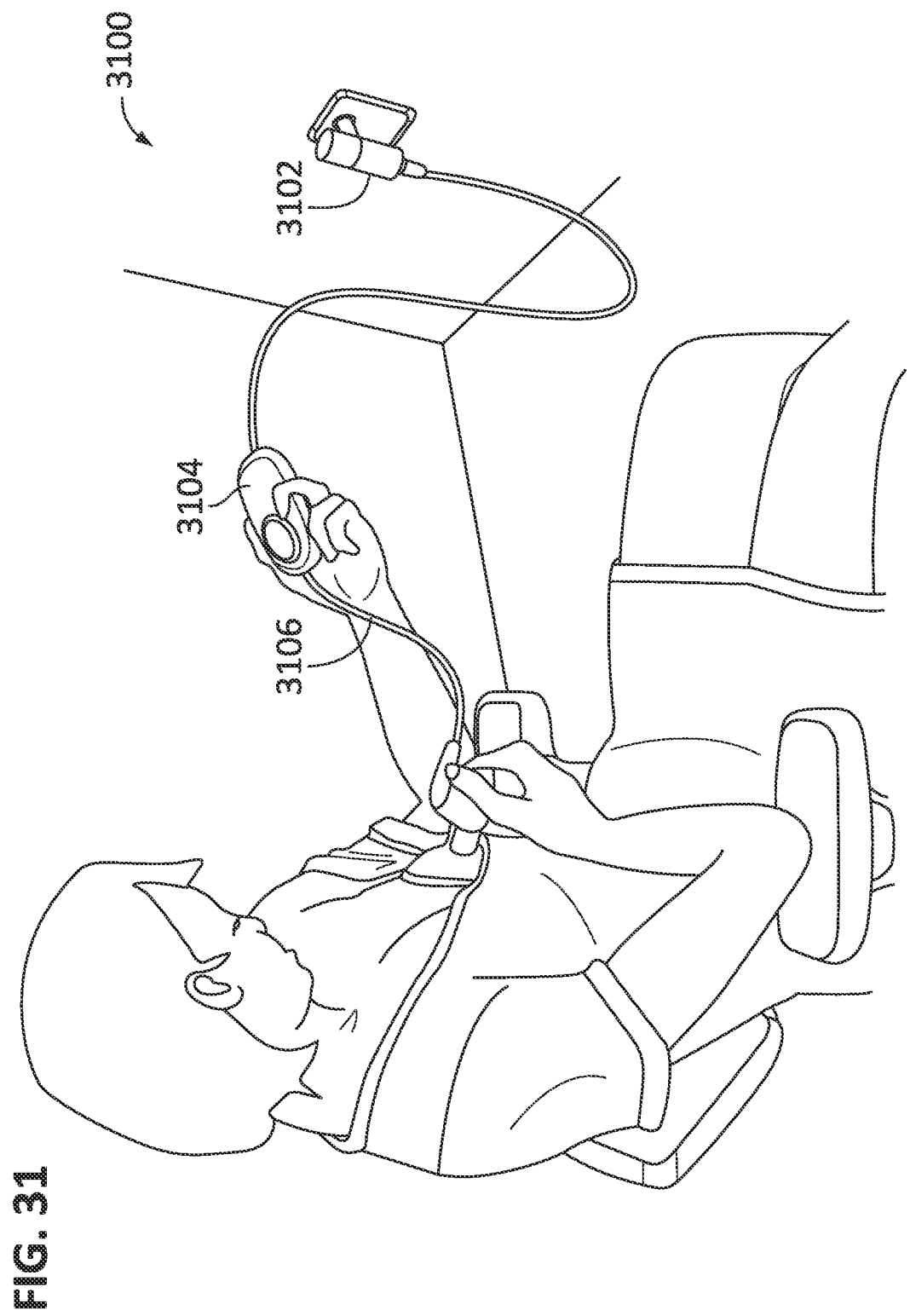

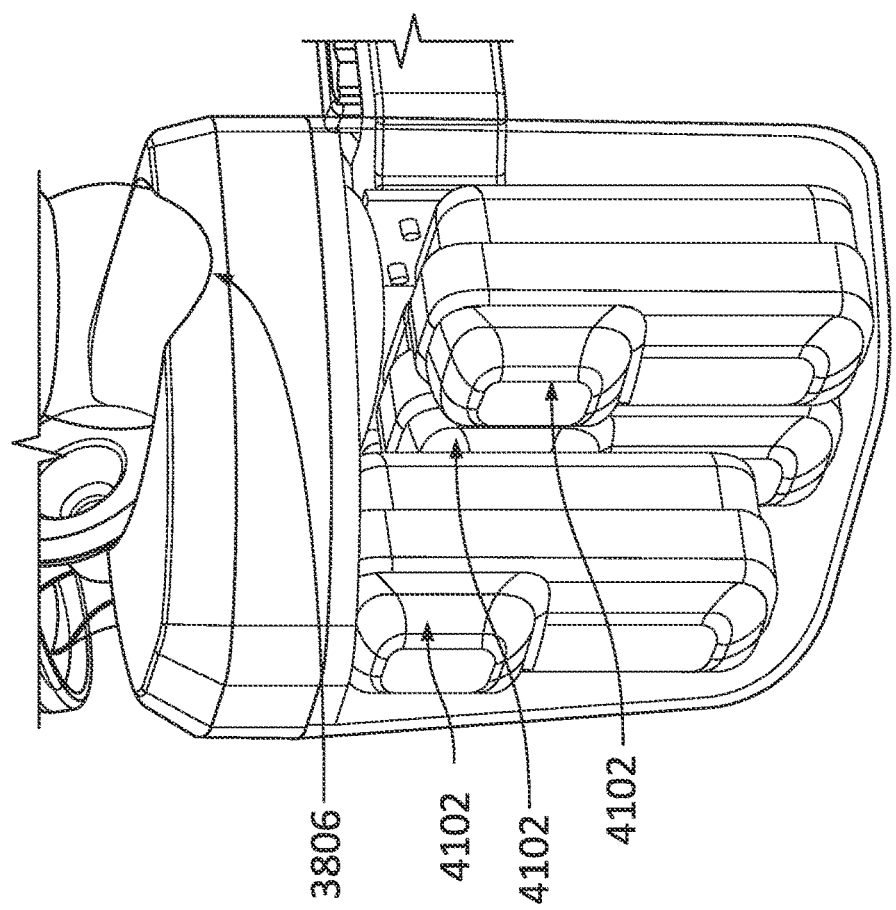
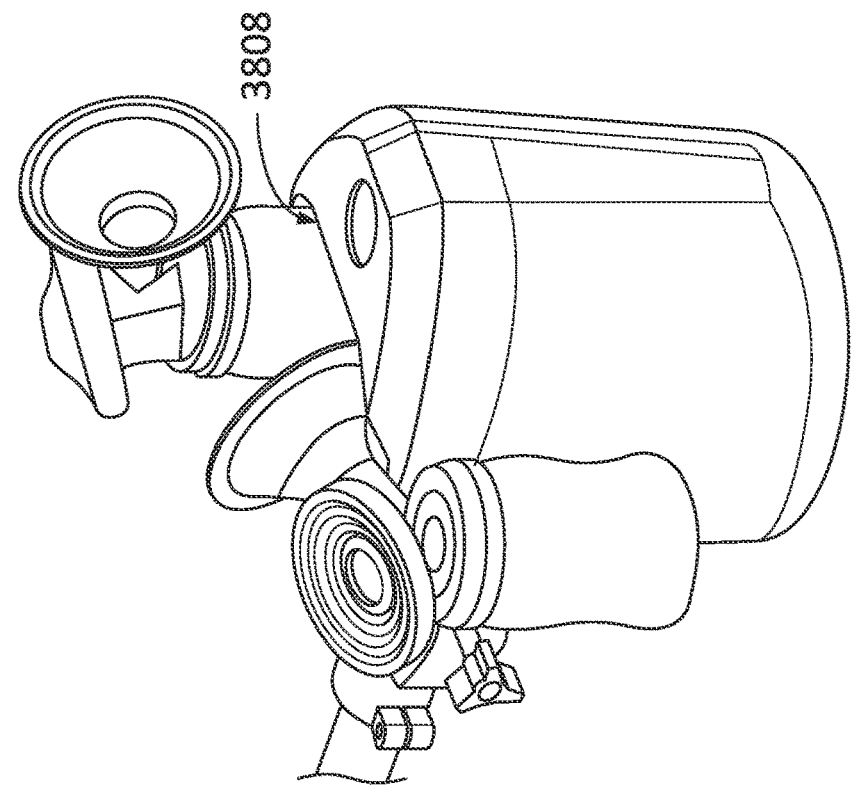

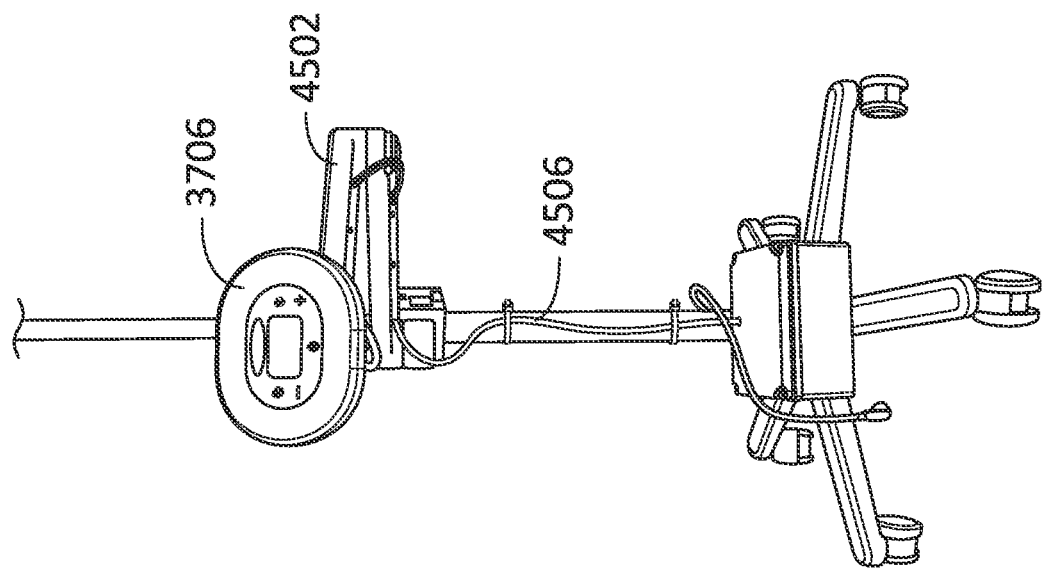
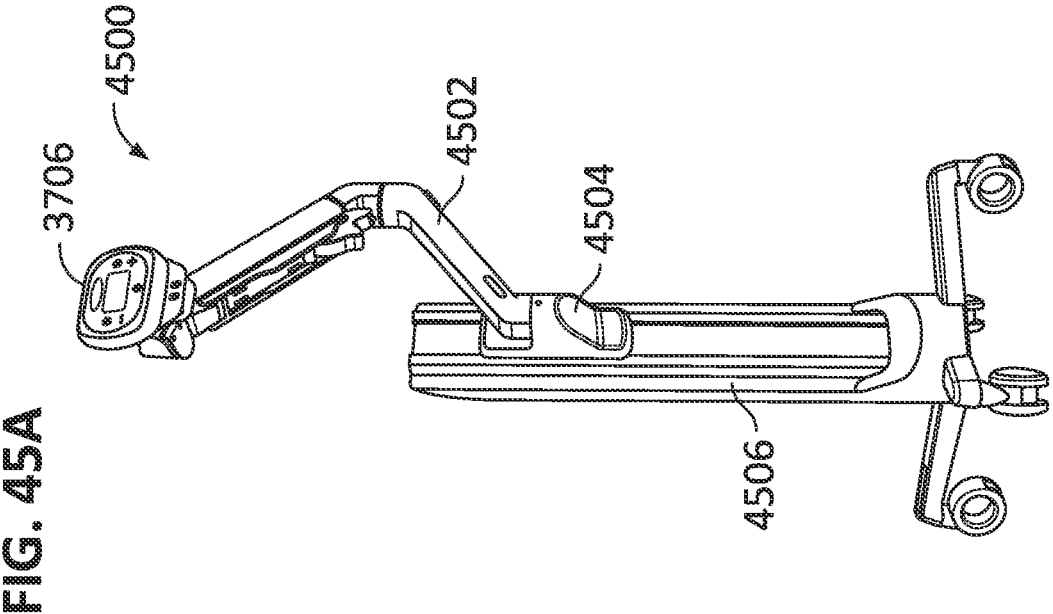

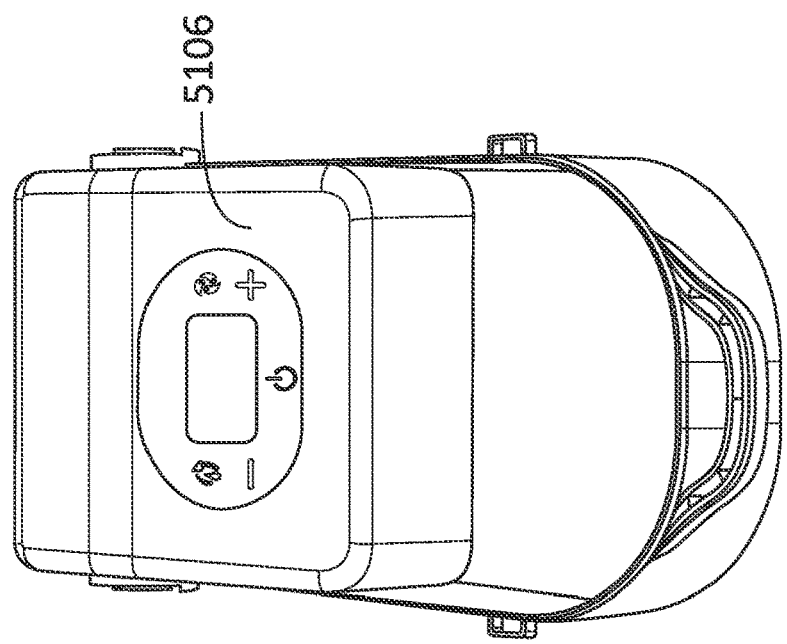
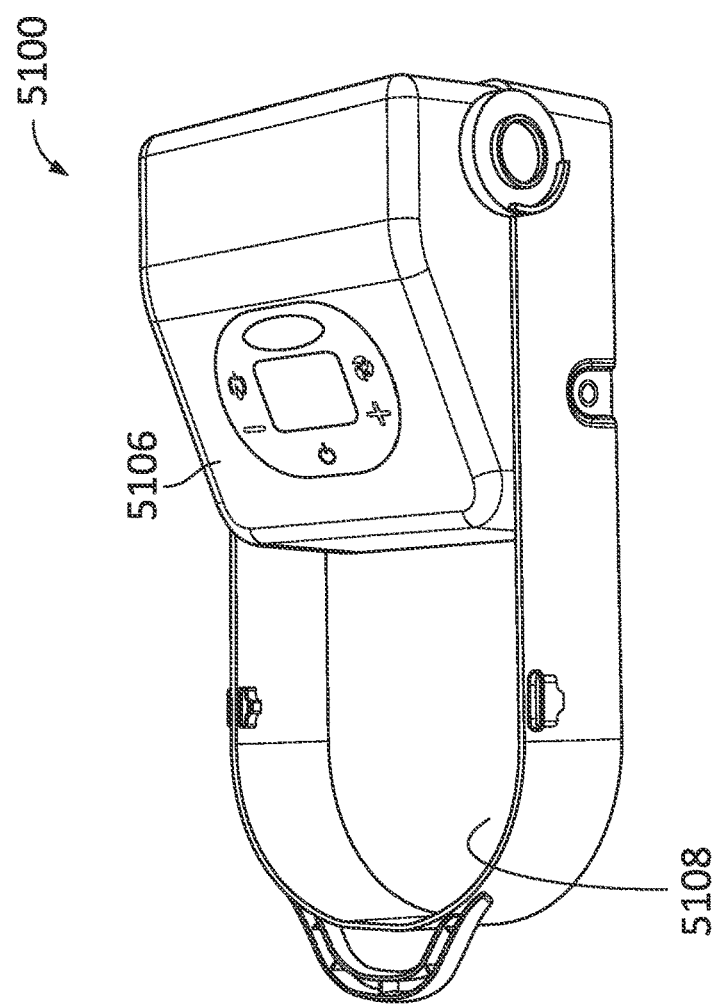

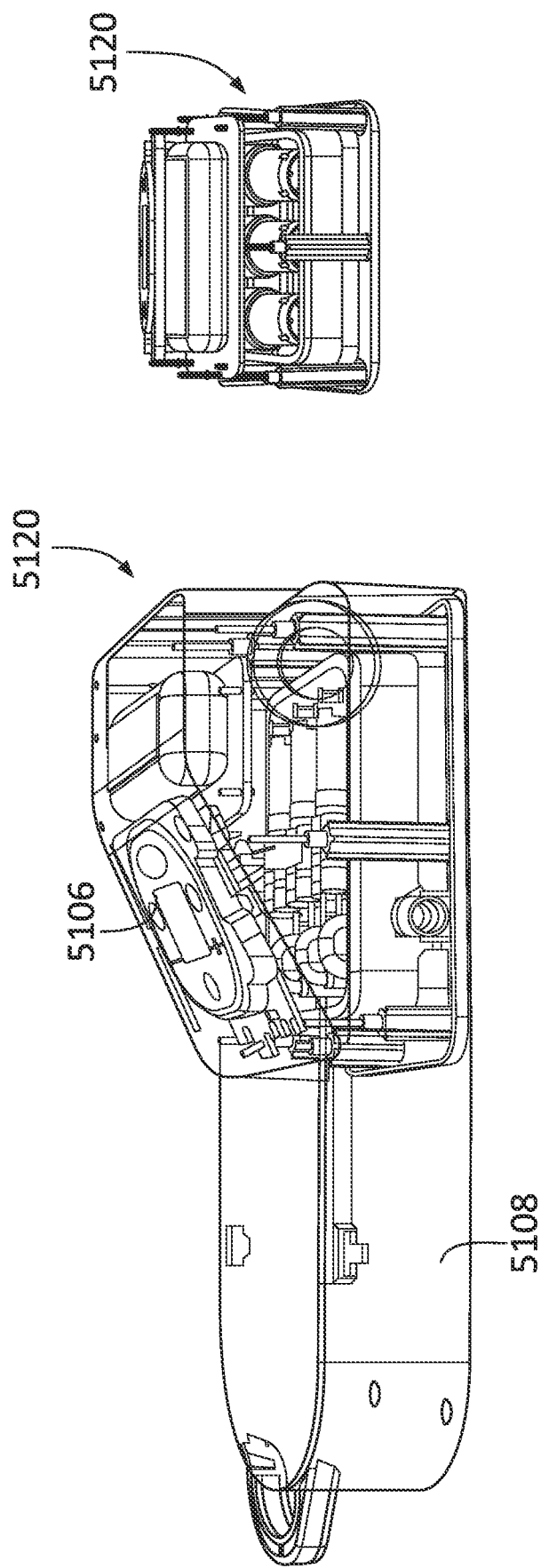

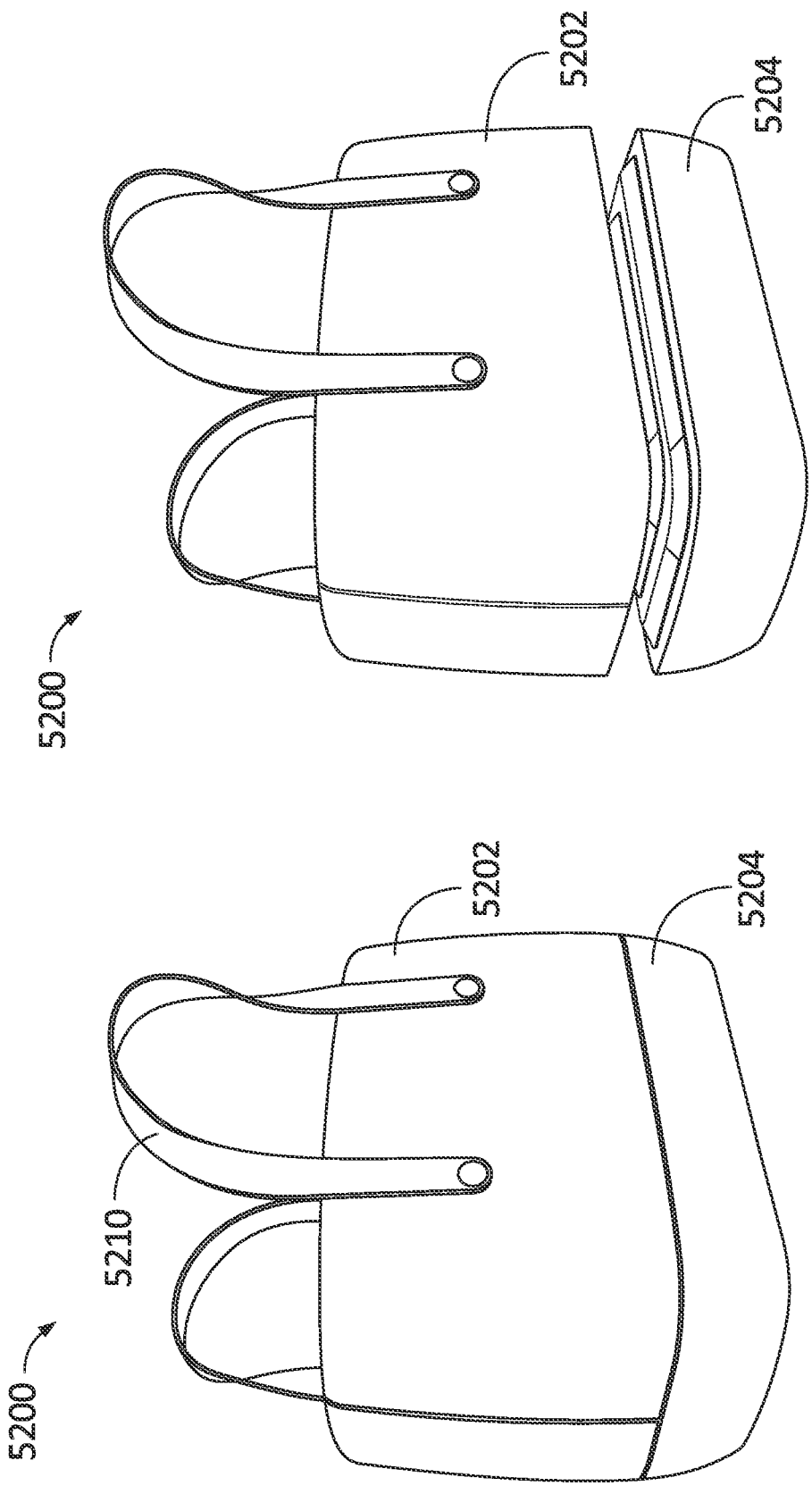

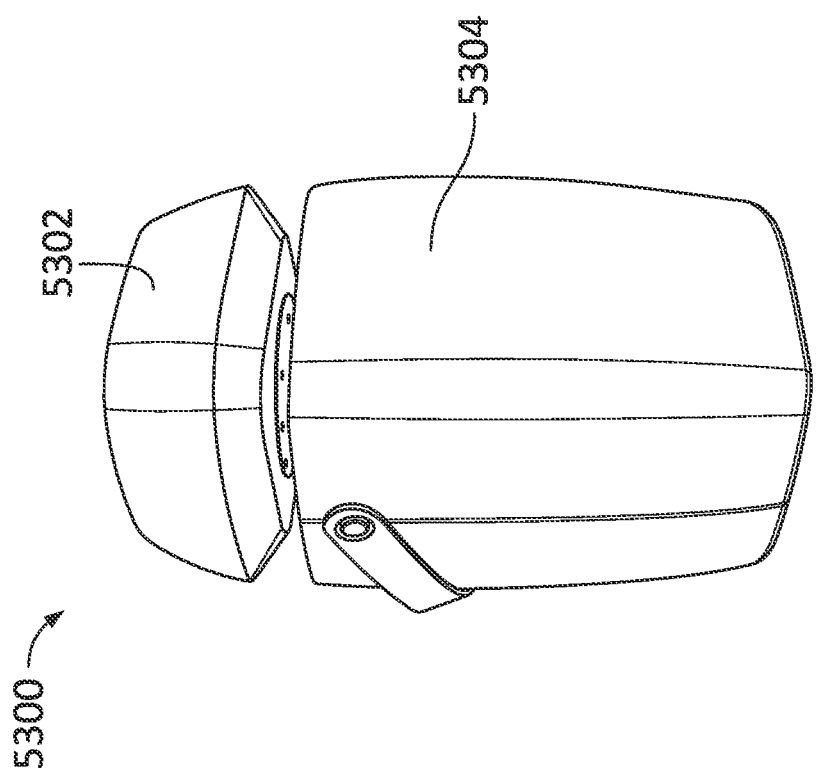
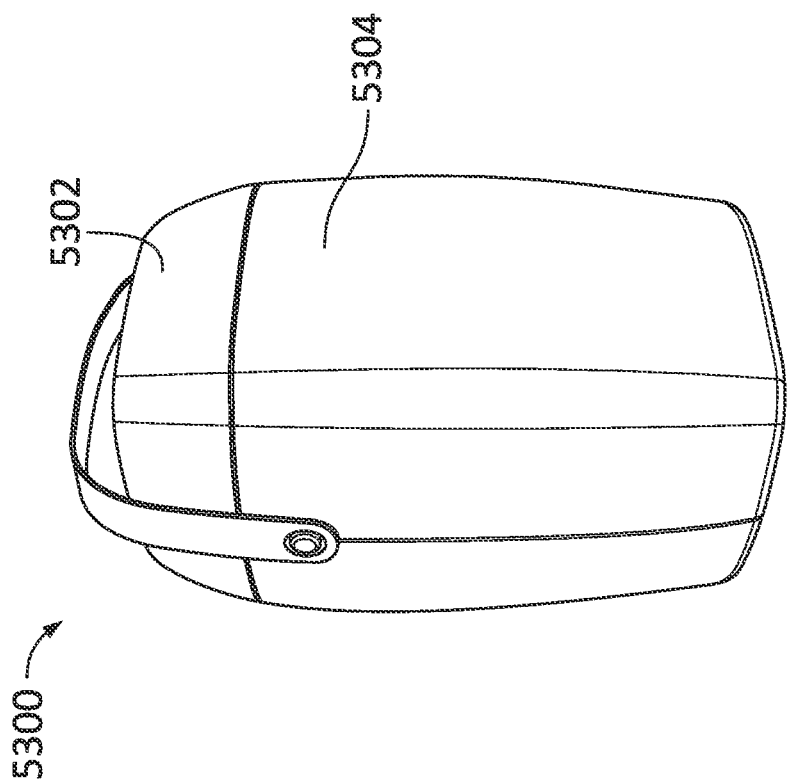

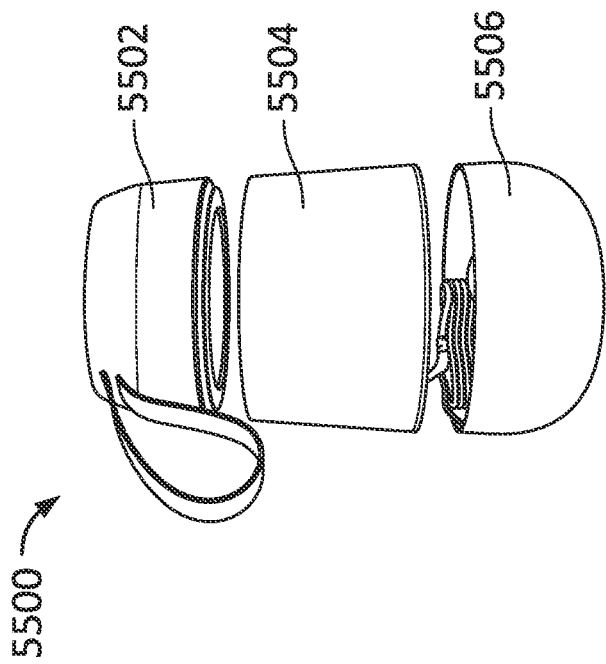
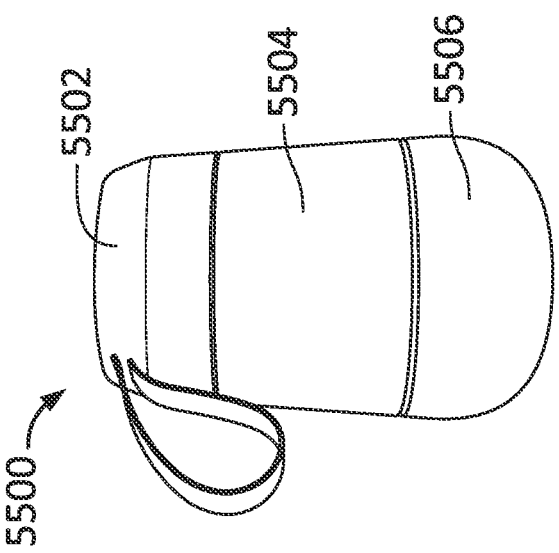

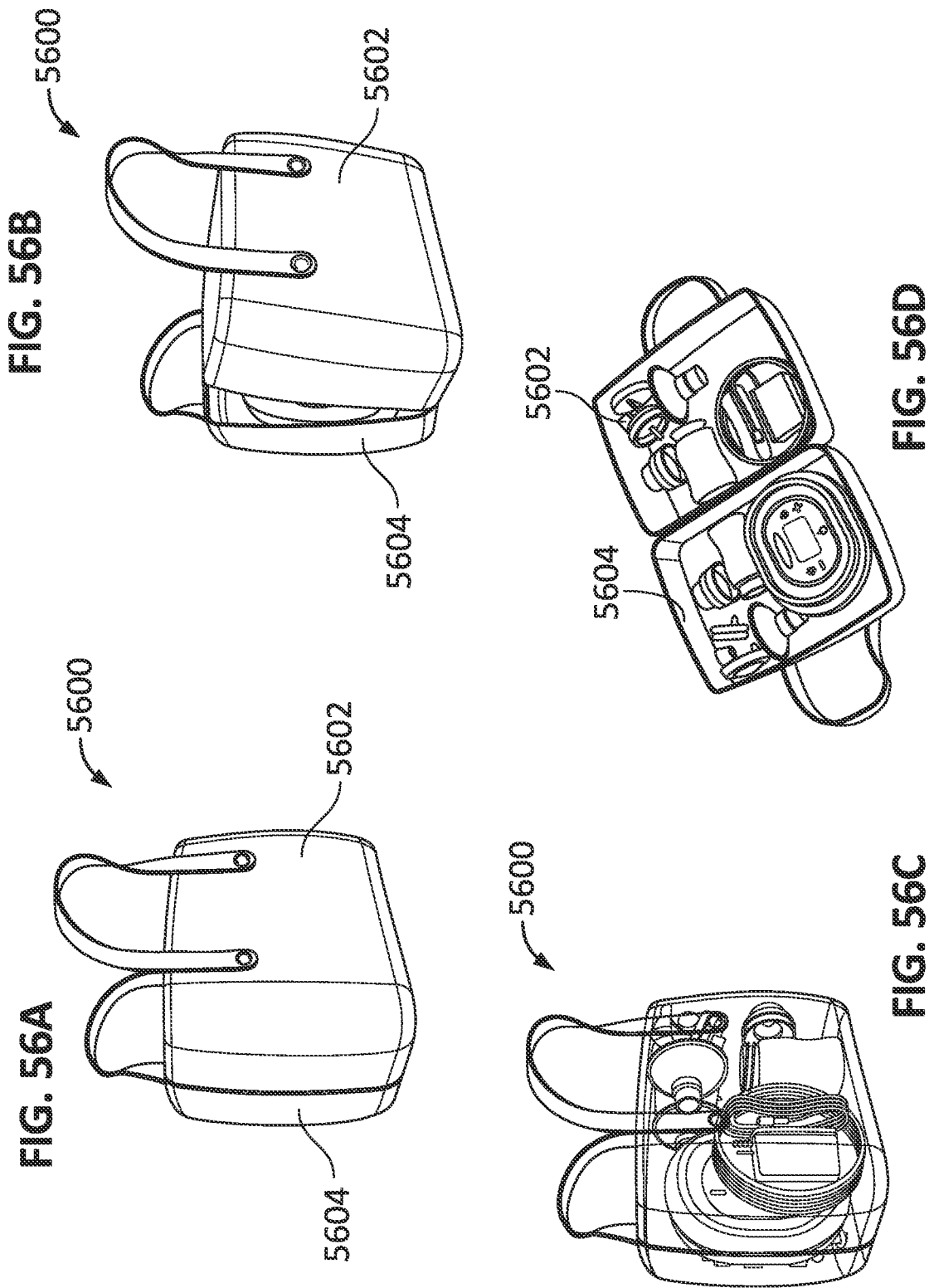

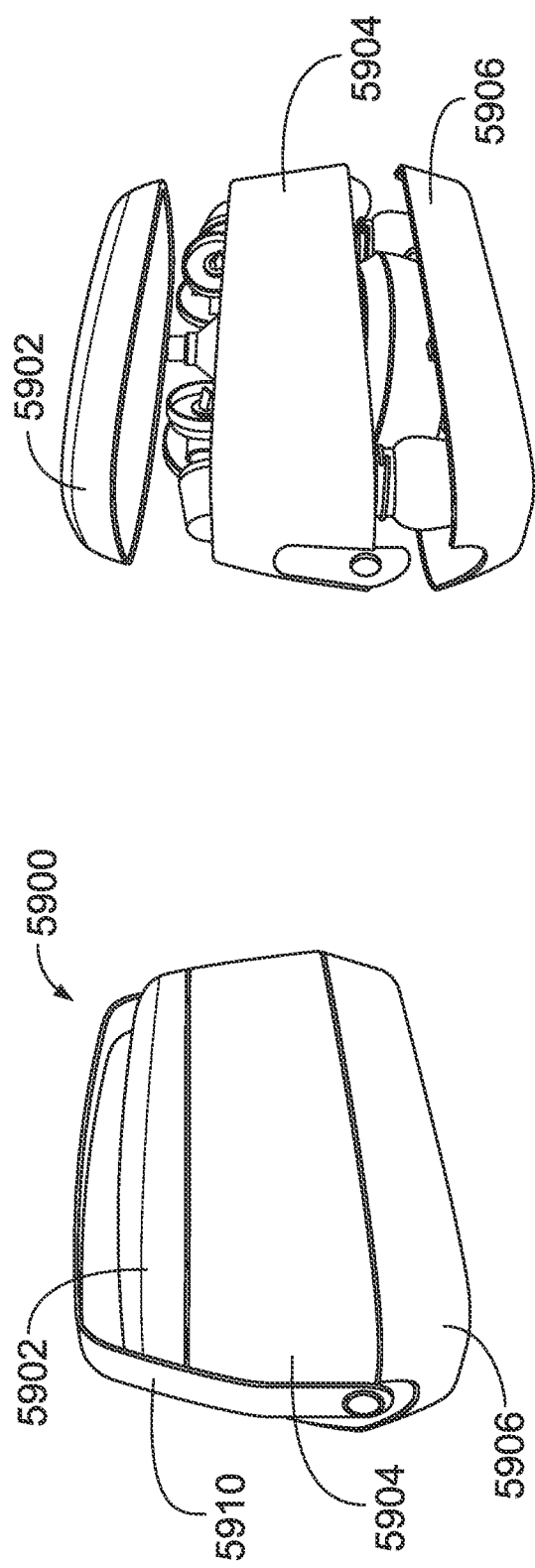

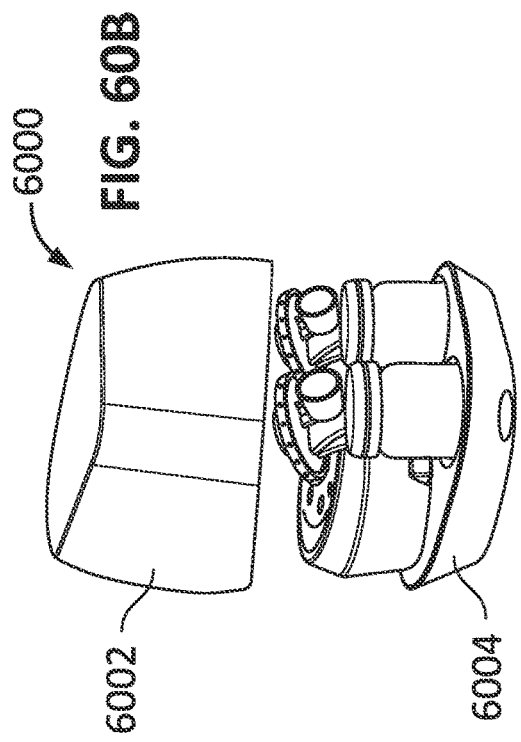
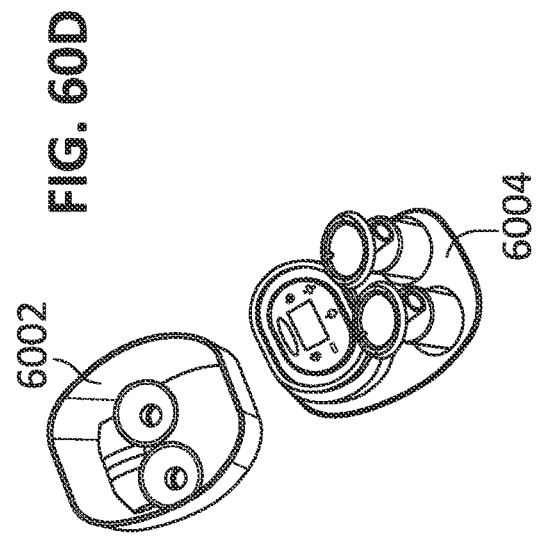
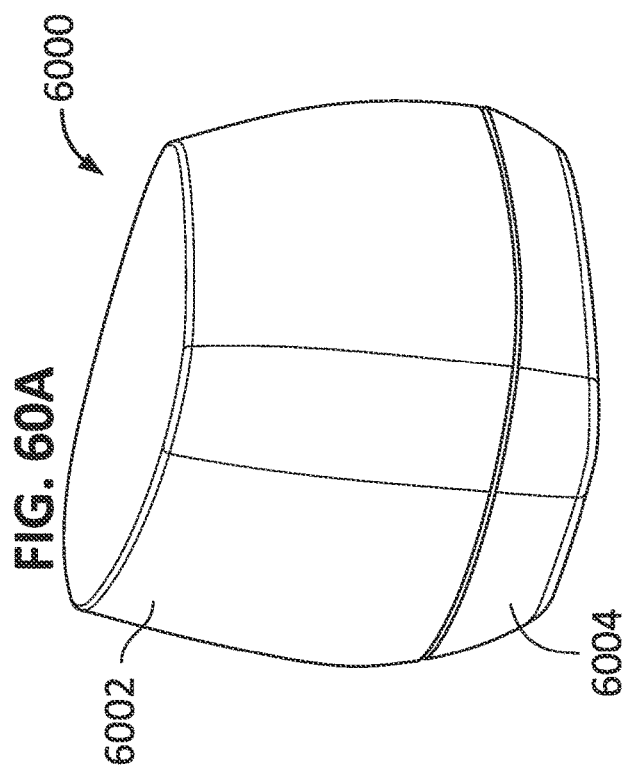
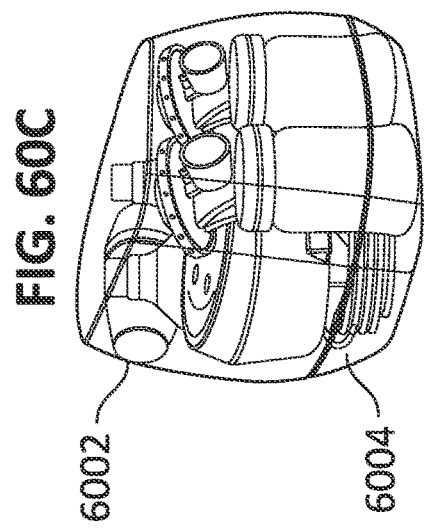

BREAST PUMPS

BACKGROUND

Breast milk expression and collection through pumps is an essential tool for nursing mothers. When mothers are not able to be in the same proximity to the baby, breast pumps provide a vital lifeline to capture milk when it is available, so milk supply remains high and the baby can consume the milk on its own schedule.

Today, pumps are also used outside of a retail setting in the hospital, as well as in the rental market. In the hospital and rental spaces, pumps need to last for multiple mothers who may be one of just many different users of a pump over a multi-year life span that the pump is intended to be in service. Breast pumps today generally include a single motor connected to at most two diaphragms and/or they are systematically connected to a single printed circuit board and/or single solenoid or pressure release valve.

Breast pump manufacturers have continually focused on improving pump reliability by sourcing specialized components that have singular high reliability, which has limited the reliability and performance characteristics of pumps largely to single components of each type within a single breast pump. Unfortunately, as a result, most pumps cannot function at a high degree of performance for more than one or two years without repair and maintenance, due to the limitations of each individual component.

BRIEF SUMMARY

The present application describes an alternative method of providing a high reliability breast pump that is unique in its advantages, function, and composition compared to existing multi-user and single-user breast pumps. The method involves using multiple redundant components in concert with a control system inside the pump housing.

The disclosed device is a high reliability design for a breast pump in which the entire pumping system can perform longer without ceasing to function compared to traditional breast pumps. Traditional breast pumps only contain one motor to drive suction to one or both breasts or, in rare occasions, breast pumps contain two motors that independently suction one breast at a time in double pumping mode.

The present application describes a breast pump with multiple motors, electrical components, seals, diaphragms, batteries, and/or other components made to serve as redundant back up configurations such that if one component fails the replacement component is able to start up in its place after the system re-routes or adjusts the current path of power circuit or adjusts the flow path of the vacuum. Previous breast pump systems are made to last one or two years with one motor or at most two motors aligned for a single breast. Two or more breast pump motors may be configurable with one or both breasts in addition to the potential to add redundant components of other elements such as but not limited to a redundant printed circuit board. Other components may also be duplicated and may be independently controlled to turn on or off by a computer control system, PCB, power circuit, mechanical switch, or other mechanism known to those skilled in the art.

The present application describes devices where the control unit may be moved some distance away from at least a portion of a main part of a breast pump configuration. This distance is created by a mechanism having a breast pump unit at a lower center of gravity than a movable control unit. In other embodiments, this is accomplished by the vacuum suction being part of a secondary device or structure that the control unit can connect to and be movable in space relative to an outlet suction portion via a tube. In yet other embodiments, the control unit and pump are housed in one unit but that unit is only one part of a greater system which includes a docking station such that the user could move part of the pumping mechanism to a different area of space without needing to be connected physically to this other main part of the pumping system.

This disclosure provides multiple different embodiments such that a user could use adjust the position of major parts of the pumping system in space relative to each other with ease to facilitate easier workflows within the breast pumping regime.

Finally, the present application describes pumps that both incorporate multiple redundant components and devices where the control unit may be moved some distance away from at least a portion of a main part of a breast pump configuration.

BRIEF DESCRIPTION OF THE DRAWINGS

FIGS. 9A and 9B depicts exemplary top angled three dimensional and side angle three-dimensional views of a breast pump with multiple internal components that may be redundant and/or configured for series or parallel actuation by one or more control units in a highly compact configuration.

FIGS. 21A and 21B depict an exemplary embodiment of a breast pump device for use with one or multiple users where the center of mass is close to the ground and the interactive mechanism is on bendable snake tube that can pivot in many directions.

FIGS. 22A and 22B depict an exemplary embodiment of a breast pump device for use with one or multiple users where the center of mass is close to the ground and the interactive mechanism is on a pivoting or rotating pole that has at least one semi ridged or ridged section on a hinge.

FIG. 31 depicts an exemplary breast pump embodiment used in a medical or research setting such that the source of suction is in a separate location from the control unit and a flexible tube connects directly to the wall or other stationary source of suction such as but not limited to an in house hospital vacuum system.

FIGS. 41A and 41B depict exemplary views of a vacuum unit of the pump system of FIG. 38.

FIGS. 45A and 45B depict an exemplary view of an alternative pump system.

FIGS. 51A-51F depict an exemplary view of a portable pump system.

FIGS. 52A-52D depict an exemplary view of an alternative portable pump system.

FIGS. 53A-53D depict an exemplary view of an alternative portable pump system.

FIGS. 55A-55D depict an exemplary view of an alternative portable pump system.

FIGS. 56A-56D depict an exemplary view of an alternative portable pump system.

FIGS. 59A-59D depict an exemplary view of an alternative portable pump system.

FIGS. 60A-60D depict an exemplary view of an alternative portable pump system.

Figure 1:
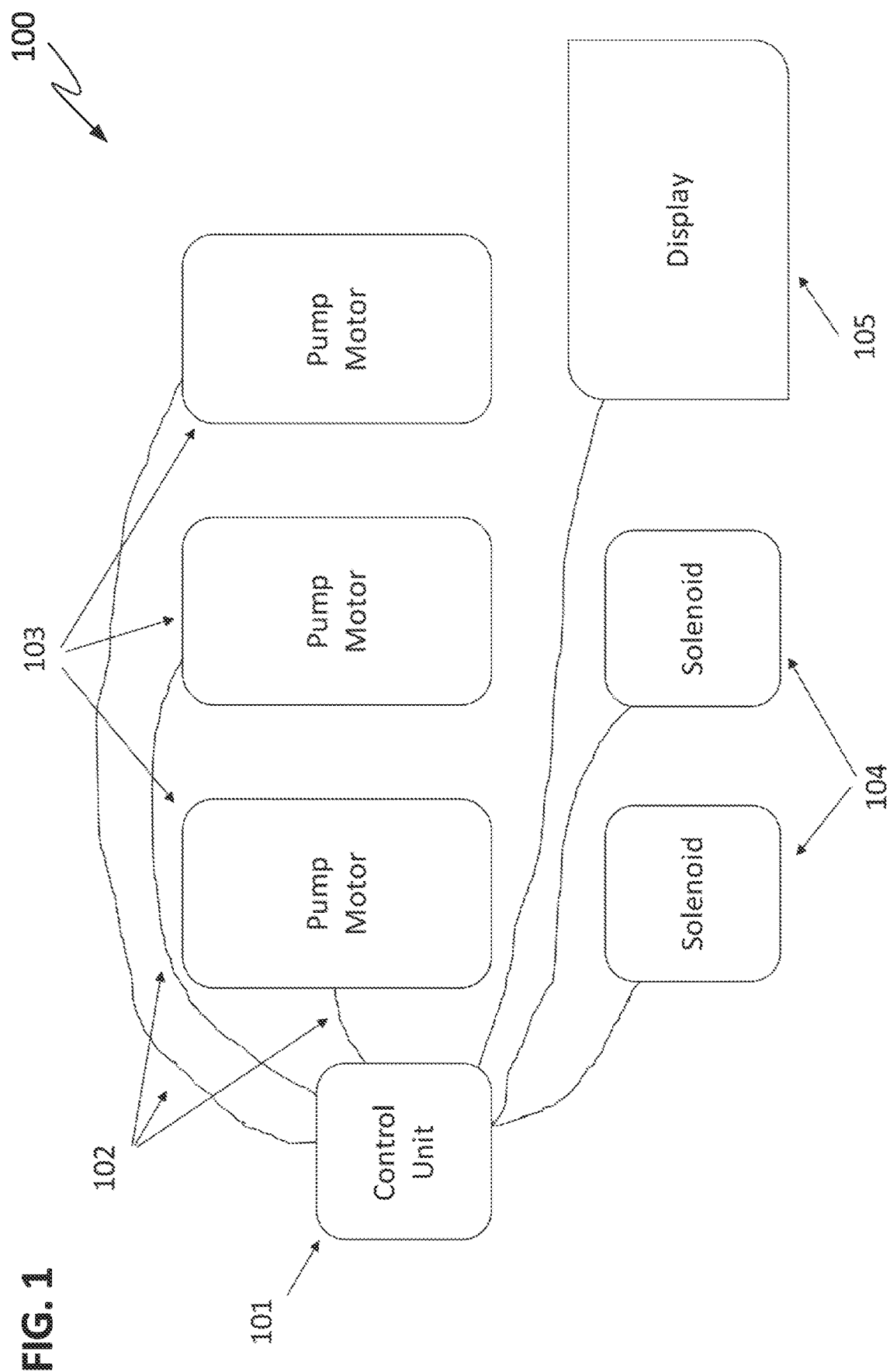
FIG. 1 depicts an exemplary breast pump configuration with multiple pumps and multiple solenoids linked together at one central control unit system and/or a display so that multiple fail-safe motors, solenoids, and/or other pump parts are included within the pump system.

The drawings are not intended to be limiting in any way, and it is contemplated that various embodiments may be carried out in a variety of other ways, including those not necessarily depicted in the drawings.

DETAILED DESCRIPTION

In some aspects, the present application describes a long-life breast pump apparatus that automatically facilitates the internal switching of components from one to another by the machine itself. A human may or may not be prompted to confirm a change or acknowledge if one component has reached the end of its life or has failed. In some embodiments, the mechanism detects when to deactivate one component and only use active components or automatically deactivates one component after a certain number of use cycles, hours, or power up times.

In other aspects, multiple embodiments are disclosed of devices where the control unit may be moved some distance away from at least a portion of a main part of a breast pump configuration.

In yet further configurations, multiple embodiments are disclosed of devices that incorporate both internal switching of components and control units moved away from a portion of a main part of a breast pump configuration.

Referring now generally to FIGS. 1-20, some embodiments include multiple motors inside a breast pump housing with at least one PCB controlling the multiple motors. Each motor may be configured independently or together by the software in the housing circuit or by an external mobile application communicating with the pump motors through blue tooth, Wi-Fi, near field, RFID, or other mechanism that allows data to be sent to and from a mobile device.

In one such embodiment, multiple motors are assembled inside a pumping mechanism, and the computer system detects when a motor is not functioning properly by measuring the current draw compared to vacuum output, vacuum output alone, or other sensory element that would enable the electronics in the pump to turn off the faulty or near the end of its useful life pump motor and then automatically turn on a new pump motor that is still good.

If there are three (or more) motors inside a pump, then the software may also detect how many cycles each motor has performed. After a certain number of cycles, the motor may be marked expired in the pump software system, such that the pump may no longer be called upon to be used by the pump mechanism and only the remaining two pump motors may be used. Then, after the second motor has reached the end of the allotted cycles, the pump would automatically switch to the third and final pump, which could run until it fails mechanically or until it reaches the pre-set limit of the number of cycles. The pump at this time could message the company that services the pump to alert them that the pump has failed and also this messaging process alerting the company of pump failures could alert to pending failures or even the usage rates of the pump so the company could proactively and accurately replace the pump prior to an end of life failure of the last pump motor.

In another embodiment, if there are multiple motors present, such as but not limited to five motors present, then the software could alternate between motors during each time the pump is in operation. For example, the pump is turned on and the first motor would be used for the entire pumping session, a set amount of time, or another time interval such as for a single cycle. The system would use the second motor for a second pumping session, a second set amount of time, and/or for another second time interval such as for a second single cycle. This process could happen for each motor such that the use of the motors could occur periodically over time such that they would wear evenly but because there are multiple pumps the wearing process would take a multiple amount of time before the entire mechanism was unable to perform at a sufficient level to be effective.

The pump mechanism could detect which motors are failing with a sensor such as but not limited to an electrical sensor, power sensor, piezo electric sensor, force sensor, vacuum sensor, or any other sensor known to those skilled in the art as a sole sensor or in combination with other sensors or sensing capabilities in order to determine if a motor or the seal around the motor is failing. In the event that a failure is detected, a message could be but need not be sent to the company for a service request or useful life depletion update as well as the signal of failure could prompt the pump mechanism to deprecate that failing motor and no longer use it for further continued operation. The user could be prompted that the pump is taking this action or the action could occur without any notification to the user in order to create a seamless experience.

The types of motors that could be used in this setup include but are not limited to a DC motor, brushless motor, piezoelectric motor, stepper motor, nitinol actuation motor, solenoid, or other mechanism that allows for the movement of components to create and/or release a vacuum and/or vibration effect. It is also understood that the duplication of the motors in the pumping mechanism can also correspondingly dictate the duplication of the sealing diaphragms in the motors and all of the other components necessary to use a motor in a complete flow circuit such as tubing, electrical wiring, circuitry, motor housings, support struts, silencing sound dampeners, seals, and many other components known to those skilled in the art which could also be duplicated beyond what would otherwise normally be expected in today's currently limited breast pump designs which only comprise one motor, one PCB, one or two seals, and at most two motors if one motor is made to be used for one breast independently. The present disclosure contemplates multiple fail-safe mechanisms and a system by which the pump apparatus detects and manages the failures over time to provide for a seamless long lasting user experience of the pump apparatus.

In yet another embodiment, multiple different types of motors could be used within a housing simultaneously and/or in a programmed sequence to each other. This method would allow for more precise tuning of the vacuum produced from the one or multiple pumps such that a variety of uniform and non-uniform rise and fall times, hold times, and/or vibratory patterns could be created by utilizing the different motors of same or different size and performance characteristics within the housing. The multiple motors housed inside could be the same identical motor or they could comprise at least one different motor or motors that have been specified to perform certain functions in a more optimal way than others such as one type of motor better at producing a fast rise time alone or in combination with other motors and/or another type of motor rated for energy efficiency when used in battery operation mode for the pump.

In this way, depending on the power source available, waveform desired by the type of mom pumping (NICU Baby, Just delivered, preemie, milk just coming in/engorged, full term, normal milk) the oscillation of the waveform and features within the waveform can be adjusted using the different motors within the pump housing. The motors may be identical but they do not have to be identical and as another exemplary example, the motors can be chosen such that motor 4 is 2 times larger than motor 2, which is 2 times larger than motor 1. The different size of the motor would have a different pressure profile or power consumption profile, which can then be leveraged to generate an approximation of any type of profile efficiently. This is accomplished by turning one or more of the different sized motors on at the same time.

Pump working configuration of the present disclosure would be changeable for each motor that is chosen by the user. The motor unit that is going to work would be chosen from the screen independently. The system would use the second motor for decreasing period of the cycle time that would lead faster pumping session that leads to pump more milk in a short time interval. The disclosed device is a long life breast pump system in which system let running more than one pumps which is near the end of life together with a working solenoid valve to enhance the life time of the breast pump system. The present disclosure comprises to get a longer life time by letting system to cross-run among the same type of pumps and solenoids. System automatically replace defected motor with the non-defected motor and letting it work with previous solenoid valve which were working with defected motor previously.

Additional configurations of the pump may not need to include a solenoid and/or vent valve in the system. In these non-solenoid configurations, the pump outlet flows may be switched to push air into the reduced pressure side of the tubing of one or more pumps that may be operating in a suction mode. In another configuration, one pump may be turned on as a suction mode and then a corresponding outlet pressure would be piped into a holding chamber that would build pressure and then become released into the system to neutralize and/or increase some proportional amount of partial vacuum to an increased level of pressure in the system.

In yet another embodiment, a user could manually unplug and plug in the power sources of individual pumps that are meant to be actuated when the device is on. In addition but not necessarily a required element, if the pump fails the plug in ports could be closed off or manually blocked to inform the user that the pump in question has failed and is no longer an active choice for powering up the system. In this configuration the pump motors could be connected internally to the same air conduit but individual pumps would need to be toggled on and off manually by the action of a user. Other such embodiments where the user facilitates this action by a mechanical switch, slide switch, or other mechanism apparent to those skilled in the art could also facilitate the action of manually toggling between different configurations of one or multiple pumps to be activated through the manual action of the user.

In addition, the power on button could be configured like a rotary retractable pin such that if the rotary dial of the push button were pressed it would rotate until a first pin location that was open for a viable pump was connected. Then if pressed again it would move to the off position or onto a second rotary position for a second pump to be activated. In addition, alternative levers or buttons could be used to manually switch one or multiple pumps on or off such that each individual pump motor has its own on and off switch and the user could activate one or multiple motors manually if they desired to turn on additional suction and ensure that the rise and fall time was actuated to the desired effect. This could also be done by inserting a card that would tell the machine which pump motors to turn on and in what order mechanically through the action of the inserted card.

In one such embodiment of a breast pump configuration, the purpose of using multiple pumps in a pump unit may be to increase the overall reliability of the pump unit. Multiple pumps could be connected to the suction port via a mechanical one-way valve such as a diaphragm valve, spring valve, duckbill valve, or similar design known to those skilled in the art such that the valve would restrict the fluid air path connection when the pump is not operating to restrict the inactive pump away from the flow channel through mechanical action. This result in only the pumps that are active to be in fluid connection to the suction port. Pumps that are not active would not affect the performance of the pump unit and the system may or may not need to include a pressure sensor. However, if a pressure sensor is present the pressure sensor will allow the processing system to determine which motor has failed, and to use another motor by switching between which motor to power on which would mechanically open the valve through the action of full suction force through that in line flow area.

Other valves may be configured such that they have multiple breaking pressures and when there is a pressure drop along the line the valve does not open but it would pop open when the motor that is closed to that valve is actuating such that the motor's suction force could be propagated down the flow path to the breast shield area. If a system does not contain a pressure sensor, the processing system can prompt the user to identify if any motor has failed through the interaction with an LCD or similar user interface to mark pumps as failed for future attempts.

FIG. 1 depicts one exemplary configuration of a high reliability breast pump 100 and/or more tunable breast pump configurations of internal components. In this embodiment, one or more pump motors 103 are linked together through connections 102 to a control unit 101. Additionally, one or multiple solenoids 104 or other types of pressure release components known to those skilled in the art are linked to the control unit 101 such that through the action of the control unit system 101 which may comprise one or multiple circuit boards, CPUs, memory chips, pressure and/or electrical sensors, will facilitate the actuation of the pump motors 103 and/or solenoids 104 to produce the desired pump performance.

In the case of one high reliability performance configuration the control unit 101 could configure each motor 103 and solenoid 104 to actuate as a single component without additional components being turned on during a breast pump cycle and/or operation of a user. In this way, the pump useful life could be extended such that when one component wears out it could automatically switch over to the next component that had not been drained of its useful life yet. In another configuration the control unit 101 could be programmed to actuate multiple pumps 103 and/or solenoids 104 together at the same time in order to produce higher suction and/or suction release, oscillating waveforms, waveforms with rapid rise or fall in pressure changes, or other such waveforms that would be desired by the configuration of multiple components acting in concert with each other simultaneously.

In addition, the action of the components and/or the control of the components would be provided through a display 105 such that the user could see desired performance characteristics and/or control the action of the pump by providing inputs to the pump system.

Figure 2:
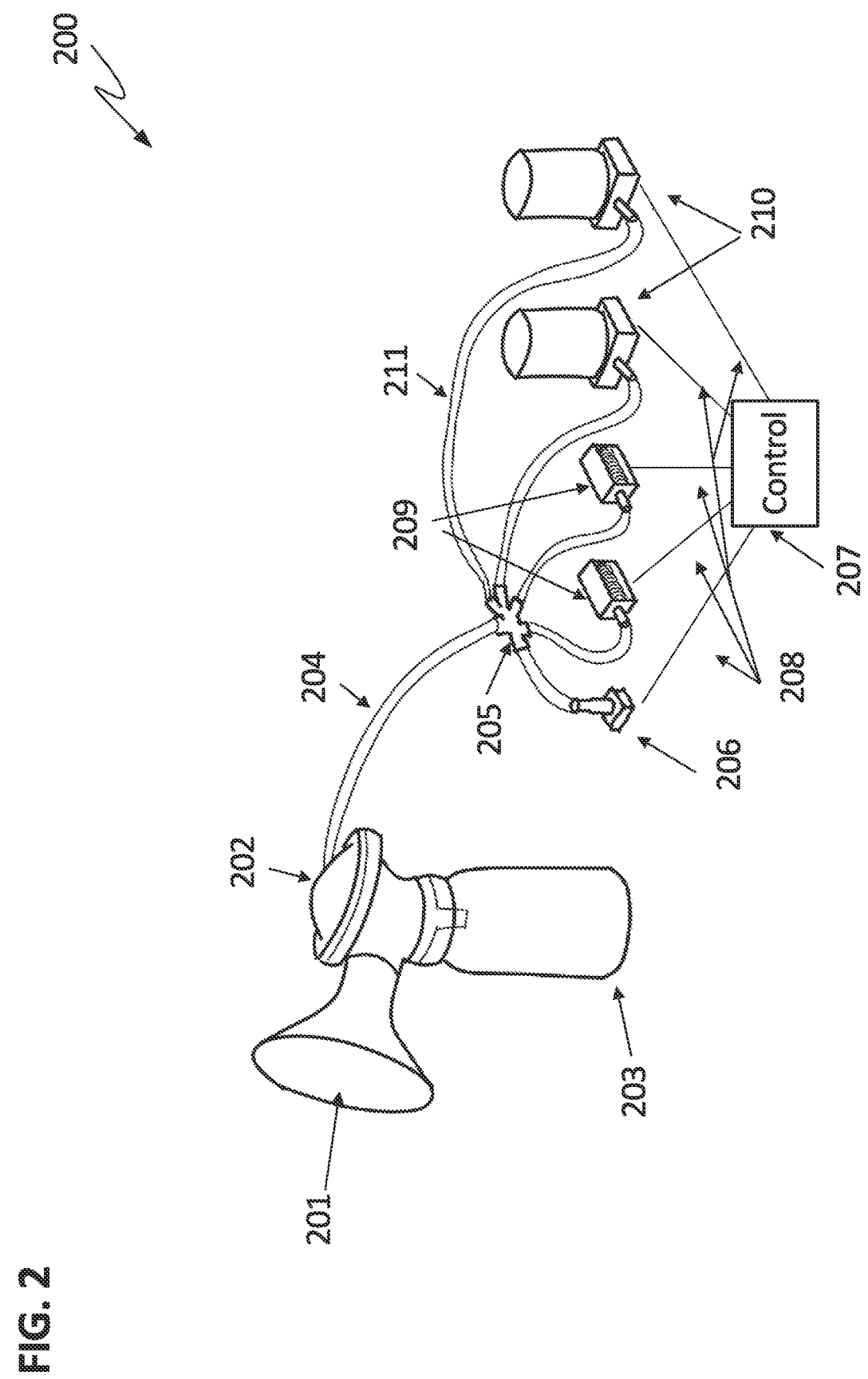
FIG. 2 depicts an exemplary breast pump configuration with many different replicated internal components to increase reliability and/or also provide for additional functionality with multiple pump motors and/or solenoids acting in concert with each other under the direction of a control units system that may itself comprise one or more redundant components.

FIG. 2 depicts an exemplary breast pump configuration 200 with internal system components linked together through suction air lines 204 and 211 by a central routing hub 205. The breast pump 200 could be configured with one or multiple solenoids 209 and one or multiple breast pump motors 210 and/or one or multiple pressure sensors 206 that would provide signal back to a control unit system 207. The control unit system 207 would provide input signals and/or receive output signals through connectors 208 to the solenoid or solenoids 209, motor or motors 210, and pressure sensor or sensors 206.

The action and modulation of the components solo or in concert with other components would be determined by the desired characteristics of the pump such as for a high reliability mode where few components are turned on simultaneously or for distinct performance modes where different components may be turned on simultaneously to produce the desired pump suction vacuum curves according to time and pressure. Vacuum wave form curves would actuate through the tubing 204 which would preferably made of a semi-ridged or ridge construction material as not to squeeze shut when under vacuum as it delivers the suction waveform to a receiving housing 202 that provides a source of suction to a breast pump flange attachment 201 which is configured to receive a breast.

Milk produced when the pressure is actuated in the breast pump flange system 201 by the source of suction 202 would flow down into a receiving container 203 which may or may not be configured to at least be partially separated from an anterior breast receiving chamber by a duckbill or other similar valve that would at least partially close upon producing at least partial vacuum in the system.

Figure 3:
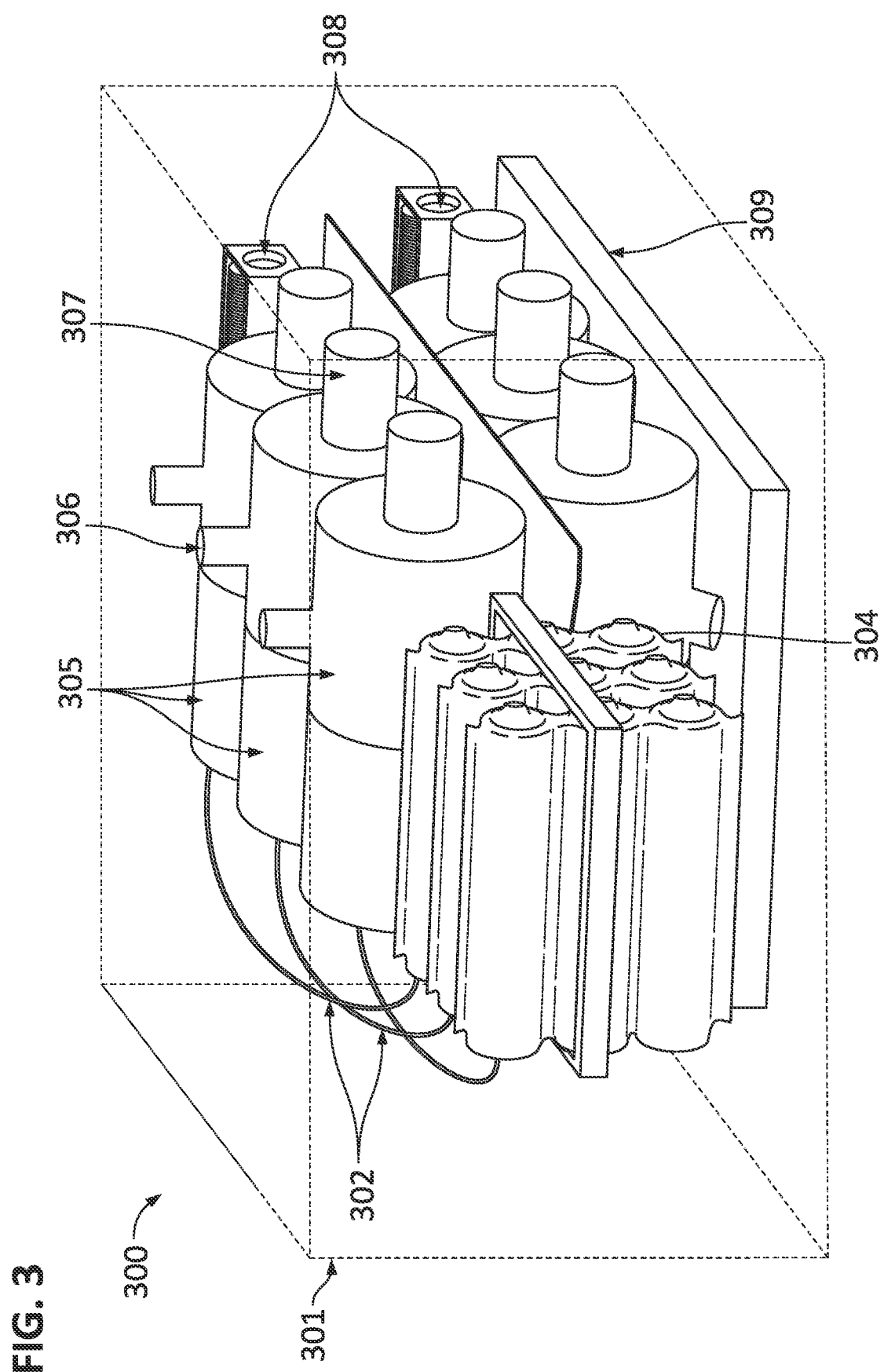
FIG. 3 depicts an exemplary three dimensional side internal view of one such configuration of a high reliability breast pump containing multiple pumps stacked next to and on top of each other to conform to a compact shape and such other parts including multiple solenoids and/or PCBs, and one or more lithium ion batteries inside a housing.

FIG. 3 demonstrates an exemplary three-dimensional internal view of how multiple breast pump internal components would be configured inside a breast pump housing shell 301. Inside the shell 301 would comprise one or more motors 305 that may be configured to stack or slot together to minimize dead space inside the housing 301. It may also be desired to have support structures for these multiple pump motors 305 and also allow for these motors to easily connect by members 302 to control unit or units 309 that could be structurally supported and/or connected together if desired. Additionally, a battery 304 may also be desired to be configured inside the housing so as to be easily removed in the same compartment as the motors 305 or in a separate bottom receptacle that could be easily accessed for removal.

One or more solenoids 308 may also be desired to be included in the design to control the release of pressure from the system. It should also be noted that other pressure release components may be used instead or in concert with solenoids such as but not limited to a pressure release valve, vent valve, purge valve, mechanical diaphragm, positive pressure motor or flow from one or more of the motors 305 included or additional motors such that the positive pressure outlet could be re-routed into the system with or without a separating valve, and/or any other mechanism know to those skilled in the art.

Figure 4:
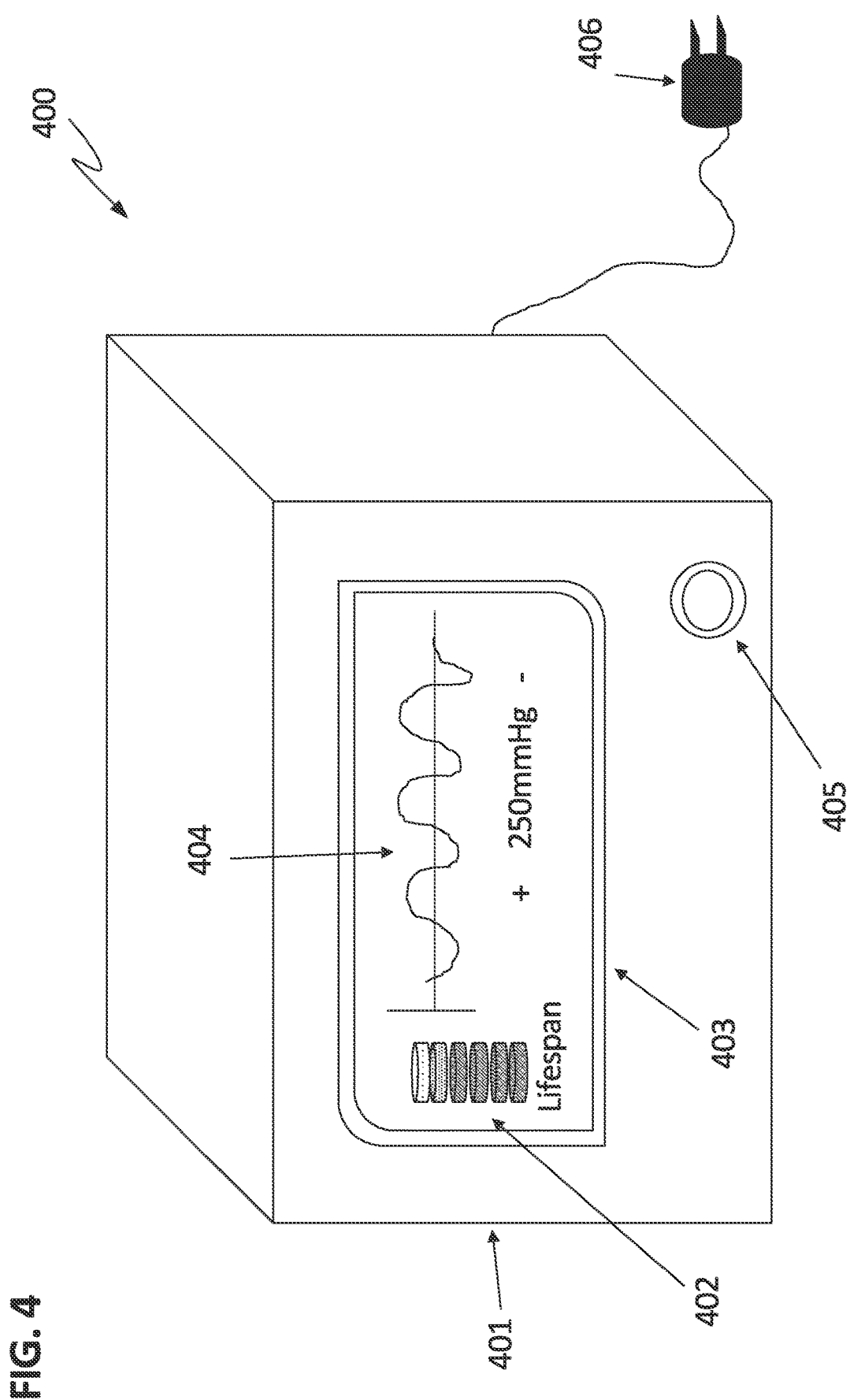
FIG. 4 depicts an exemplary outer housing three-dimensional representative view of one such breast pump configuration outer housing configured to include multiple internal components as fail-safe backups inside and a display indicating how many fail-safe backups still contain useful life.

FIG. 4 demonstrates an exemplary outer three-dimensional view of a breast pump housing 401, a display 403 that may or may not also include useful information for the users such as a component reliability or lifetime use indicator 402 and/or pressure performance curve 404. The housing may also include buttons 405 that could be used to turn the system off and on as well as control the actuation of the pressure in the system. The activation and/or operation of the system may additionally be done by facilitating the user's interaction with a control screen 403 that could have touch enabled button features. The pump 401 may be configured to hold a battery internally and/or it may be configured to have an external method of securing power such as an electrical plug 406.

Figure 5:
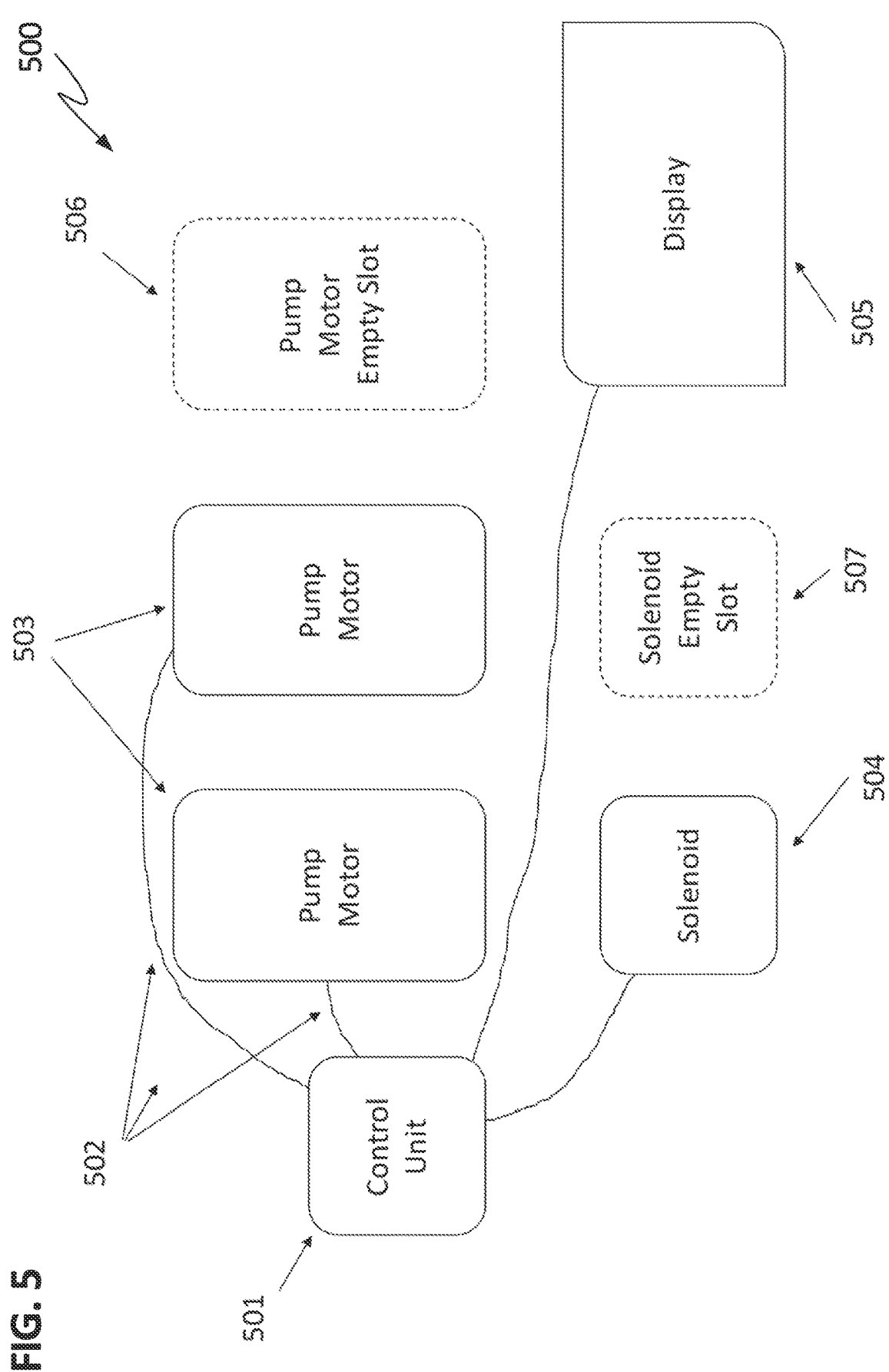
FIG. 5 depicts an exemplary breast pump configuration with the options to include multiple pump motors and/or other components such as but not limited to solenoids and/or control units such that if one part is not present a void space would be available and/or configurable to receive that part to easily allow for different models of pumps with similar housing components for different markets requiring different reliability specifications.

FIG. 5 demonstrates an exemplary breast pump configuration 500 with one or more control units 501 that are connected 502 to at least one or more pump motors 503 and/or solenoids 504 as well as potentially at least one display unit 505. Additionally, the internal configuration of the pump may be made to purposefully leave open slots to receive additional components such as an open slot for an additional pump motor 506 and/or an open slot for additional components such as a solenoid 507 which would allow a business or a consumer to adjust internal configurations to optimize for cost and performance as would be desired by different markets without needing to re-configure the overall outer design of the breast pump unit.

Figure 6:
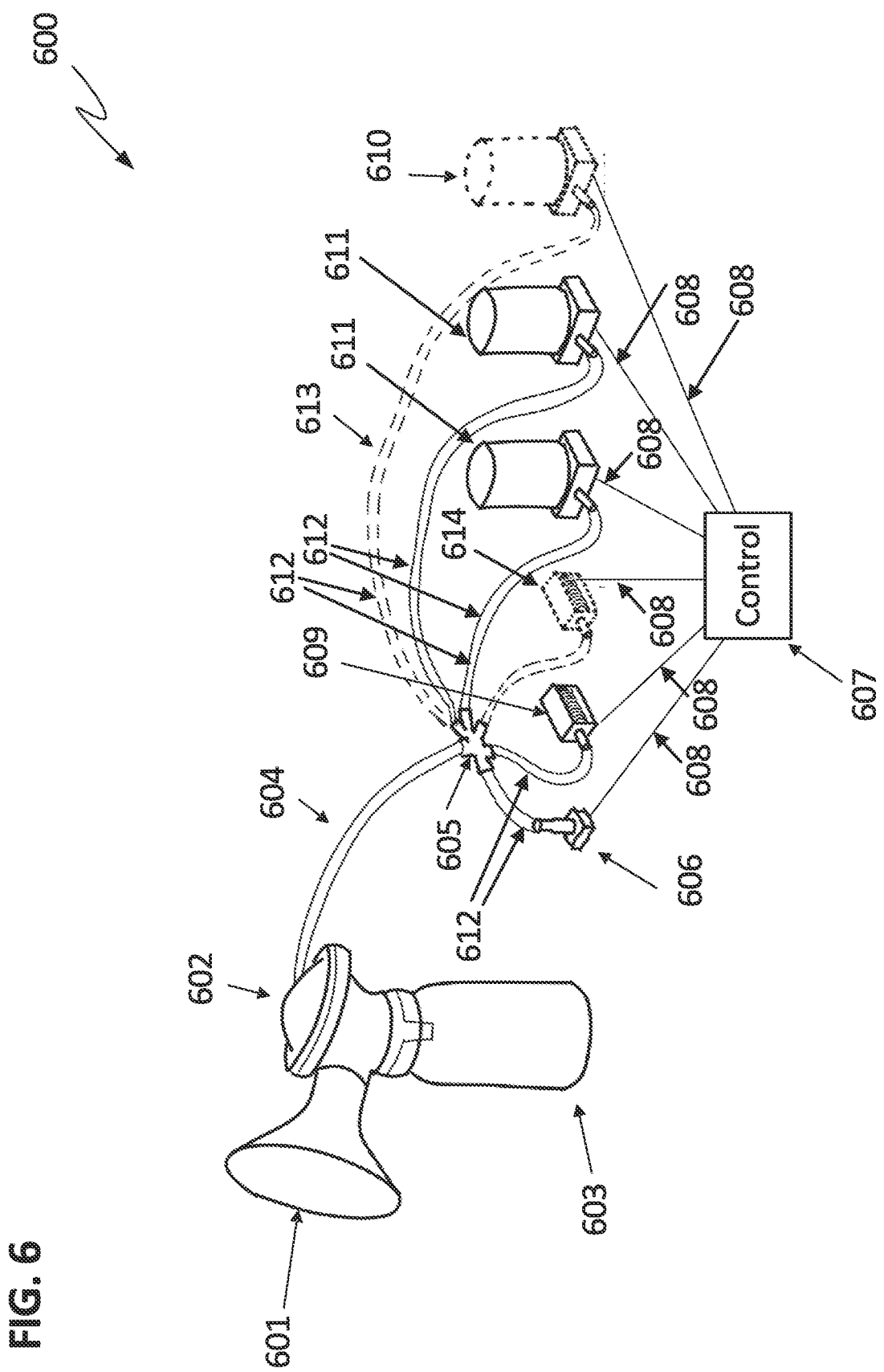
FIG. 6 depicts an exemplary breast pump configuration with options to include or not include multiple redundant or supplementary internal components such as additional motors, solenoids, and/or vacuum sensors, configured to be operated through the action of a central control unit.

FIG. 6 demonstrates an exemplary embodiment of a breast pump internal configuration 600 and an exemplary external breast receiving receptacle 601. The configuration could also be configured where a breast receptacle could instead be something that is any hands free breast cups, freemie cups, or other configurations distinct from that demonstrated herein but know to those skilled in the art. This pump configuration could comprise at least one or more pump motors 611, and/or at least one or more pressure sensors 606 and/or at least one or more solenoids 609 that are connected by wires 608 to a central control unit 607 that may comprise one or more circuit boards, memory units, processors, and/or other control system components.

In addition, tubing 612 would connect the air streams and/or pressure waves and/or vacuum waves between the various components to a central splitting hub 605 that would actuate to facilitate the vacuum and/or pressure stream through a main tube 604 from the specific peripheral tubes 612 that are in operation to a source of suction connection 602 in a breast pump receiving apparatus 601 such that a breast would express milk into a collection compartment or container 603. In addition but not necessarily a requirement of the system, space within the system may be configured to accept additional tubing 613, connectors for power or signals to or from components, pump motors 610, solenoids 614, or other components that would be useful to allow for acceptance into a reserved open space. These open spaces would be useful to configure a device for specific markets that have different requirements based on performance, life of warrantee, and/or cost.

Figure 7A:
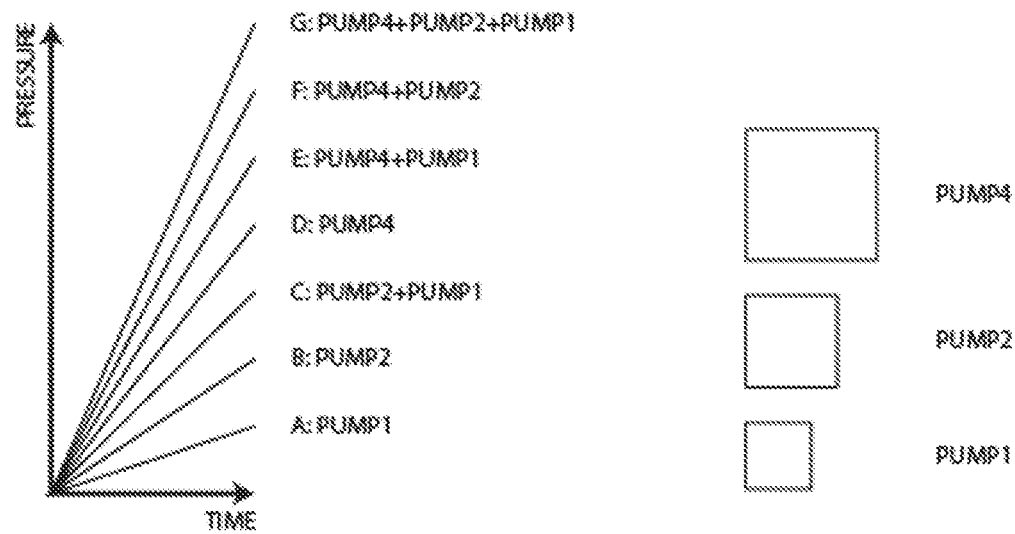
FIGS. 7A, 7B, and 7C depict exemplary breast pump pressure configuration diagrams that could be achieved by activation of a single or multiple of the same or different types of internal components by a control unit to produce different pressure increase, vacuum, and/or pressure reduction wave forms with simultaneous and/or sequential activation of motors and solenoids of different size, speed, strength, cycle programming, and/or responsiveness specifications.
Figure 7B:
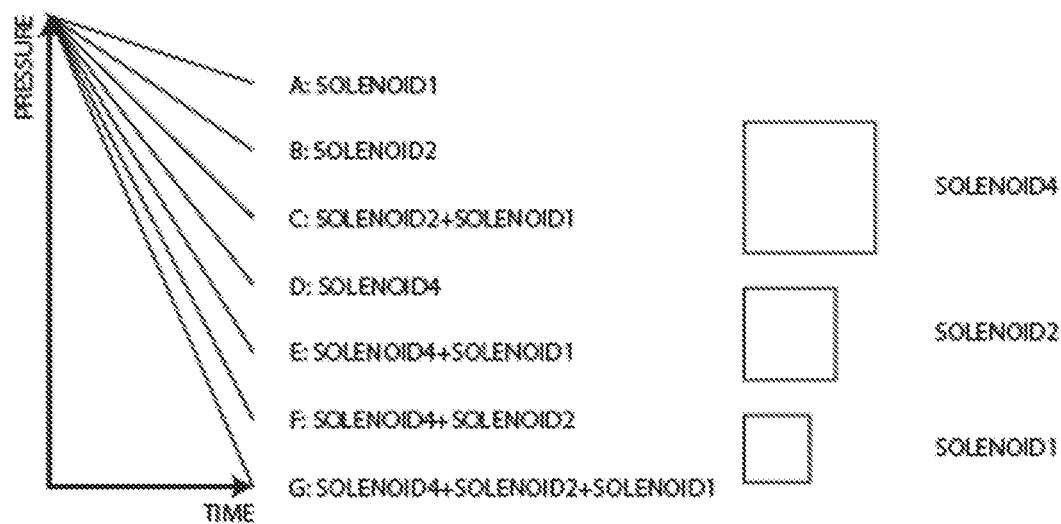
Figure 7C:
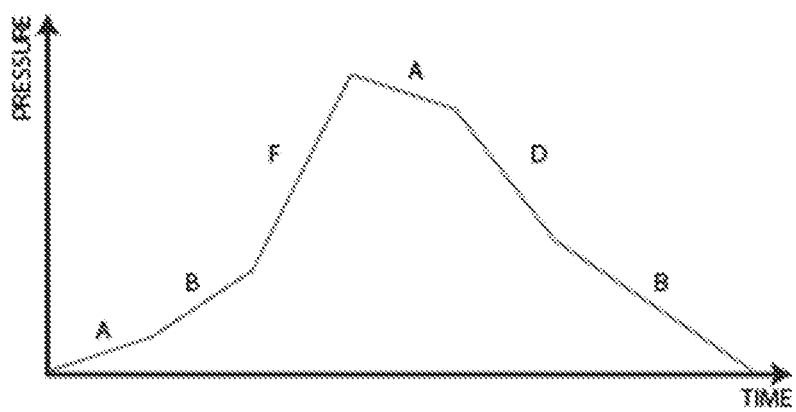

FIGS. 7A, 7B, and 7C describe exemplary pump pressure curves that are representative of different combinations of single or multiple components of the same or different models of pumps, motors, and/or solenoids in combination or separately to actuate to produce different suction and/or pressure release patterns by the overall operation of the breast pump system.

FIG. 7A represents pressure change over time based on the actuation of pumps in different configuration. It should also be noted that the present embodiment described in FIG. 7A could serve to reduce or increase pressure and pumps or motors and solenoids could be used in combinations with each other with different or identical models of each to produce increasing or decreasing pressure variations within an oscillating pump curve suction and relaxation wave.

FIG. 7B represents pressure change over time based on the actuation of solenoids of different types in combinations with each other. It should also be noted that the present embodiment described in FIG. 7B could serve to reduce or increase pressure and solenoids and pumps or motors could be used in combinations with each other with different or identical models of each to produce increasing or decreasing pressure variations within an oscillating pump curve suction and relaxation wave.

FIG. 7C describes how the slope of pressure increase or slope of pressure decrease over time could be modulated based on the use of single and/or multiple solenoids and/or pumps in combination over time as described in the corresponding FIGS. 7A and 7B as plotted in a combined graph over time. These present embodiments are useful to describe how a breast pump suction waveform could be made to change more precisely by modulating the use of multiple components in series or parallel with each other as desired by the system.

Figure 8:
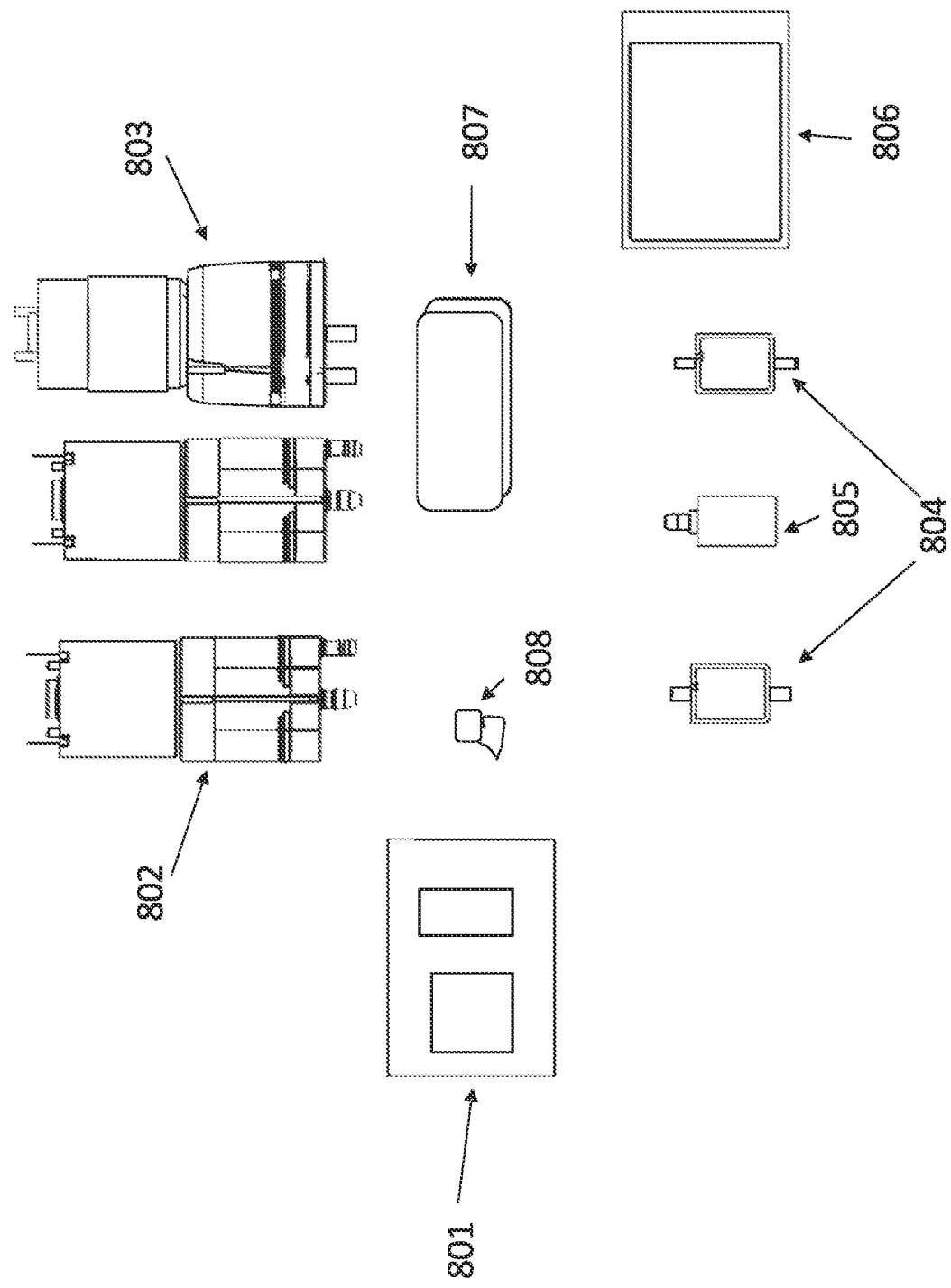
FIG. 8 depicts several exemplary components that could be included as single or multiple components internal to the presently described breast pump such as but not limited to a control unit, pressure sensor, battery, pump motors of different kinds, solenoids of different kinds, and/or a display unit.

FIG. 8 describes exemplary components that could be used within a multiple component breast pump housing. These include a control unit 801 which may or may not include a separate or embedded pressure sensor 808 or other sensing component such as to sense electrical power, impedance, resistance, capacitance, voltage, current, and/or other sensing component know those skilled in the art.

Additionally, within the multiple-component breast pump housing one or multiple pump motors of type A 802 or of additional types B 803 or even of a third or many multiples of different types could be included. Lithium Ion or other type of rechargeable batteries 807 could be included within the housing to power the motors 802 and 803 or other components such as solenoids of type A 804 or type B 805 or even of a third or many multiples of different types. Additionally a display unit 806 could be present to provide information back to the user or serve as one of several different user input mechanisms or devices with which the user could control or help direct the action of the system to operate.

FIG. 9A and FIG. 9B show an exemplary breast pump design that includes multiple redundant and/or duplicative components which may be used singularly in series or in parallel as desired by the chosen operating characteristics of the breast pump system. Within the housing could comprise one or more circuit boards 901 or other control apparatus which may be used one at a time or simultaneously. Also, within the breast pump housing may be one or more batteries 902, although some models may not have or need batteries 902. One or multiple breast pump motors 903 and 904 could be present within the system and each motor may perform a different purpose or may or may not be a different type of motor 904. One or multiple solenoids 906 and 907 could be part of the system hardware as or other pressure venting device components such as bleeder valves, pinholes, or other elements could be used as well.

Different types of pressure relief models 906 and 907 could be used such that components would not all need to be exactly the same if more than one component was chosen for the configuration. In addition, a support structure and/or stand 905 may or may not be desired to be included such that the multiple components could be configured in a compact space instead of leaving too much dead space in a suboptimal structural configuration. The structural support or stand 905 may include sound dampening feet and/or intermediary support buffers between levels and/or the feet of the support such that sound created by the actuation of the device would not be able to so easily vibrate the surface that the device was sitting on thereby reducing the sound created.

Figure 10:
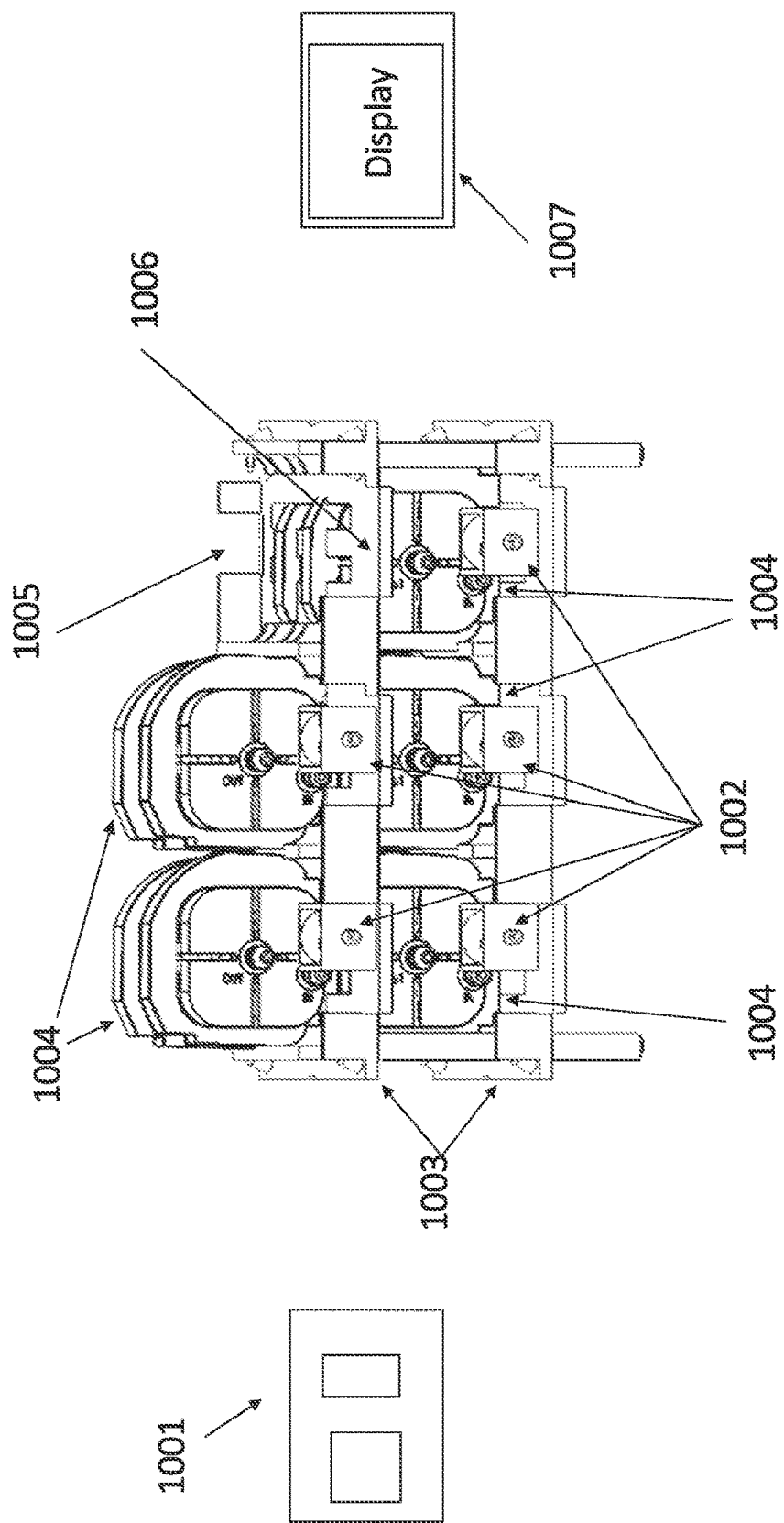
FIG. 10 depicts an exemplary side three-dimensional view with multiple redundant components in a compact structure where several component slots have been purposefully left open to receive one or more additional components such as but not limited to additional pumps and/or solenoids based on the desired market considerations for additional reliability or performance or less reliability and performance.

FIG. 10 demonstrates an exemplary side view of a breast pump system internal component setup where a control unit 1001 is configured to connect to a breast pump internal structural housing 1003 and that internal structural housing 1003 has additional slots configured to accept additional components that may not may not be present in all models such as but not limited to an additional motor slot 1005 and/or an additional solenoid slot 1006. In addition, the pump internal mechanism would include at least one motor 1004 but potentially multiple motors 1004 and may in addition include at least one pressure modulation device such as but not limited to a solenoid 1002. Each of these components of solenoids 1002 and/or motors 1004 could be the same model units or different model units as desired by the performance specifications of the model of the overall breast pump system.

In addition, a display unit 1007 could be configured to allow the user to see how the system is operating and/or control the operation of the system at least partially by providing input to the system from the user. The system may operate in several different modes that are only limited by the number of combinations in which unique components could be articulated with each other or separately. For example, if the system has one motor only then the system would only be able to configure in an on or off state or in various states of throttling up and down of that motor speed but if you included a second motor in the apparatus system then the number of combinations would be multiplied by the various different combinations of each motor which may be working in concert or against each other as desired by the system.

This combination increases exponentially as additional components are put in combination such as more motors and/or solenoids of the same or different types. It should also be understood that high reliability modes would likely preferentially mean that a pump control unit would detect which motor is operating efficiently and if a motor starts to operate inefficiently it would terminate the use of that motor component within the operation of the system. In addition, the pump could be configured to operate such that one motor and solenoid combination would be used for each pumping session of a user and then a second pumping session of the user would use a different motor and solenoid combination. This action would reduce the net number of cycles on each component and also allow components to wear evenly as the pump control unit system switched between components that were used in the last cycle and components that were on deck to be used in the future.

Other configurations of the system could include examples where multiple components were turned on simultaneously to provide peak performance and/or as a method of reducing the amount of stress and/or strain on any one component by spreading the load across multiple components. In the case where a component is purposefully missing and an open slot is present the control system would be able to detect that such a component is missing in the same way it would be able to detect that a component was malfunctioning. In this situation the control unit would establish a new operating profile for the pump with the remaining components to further extend the life of the pumping apparatus overall as experienced by the user of the system.

Figure 11:
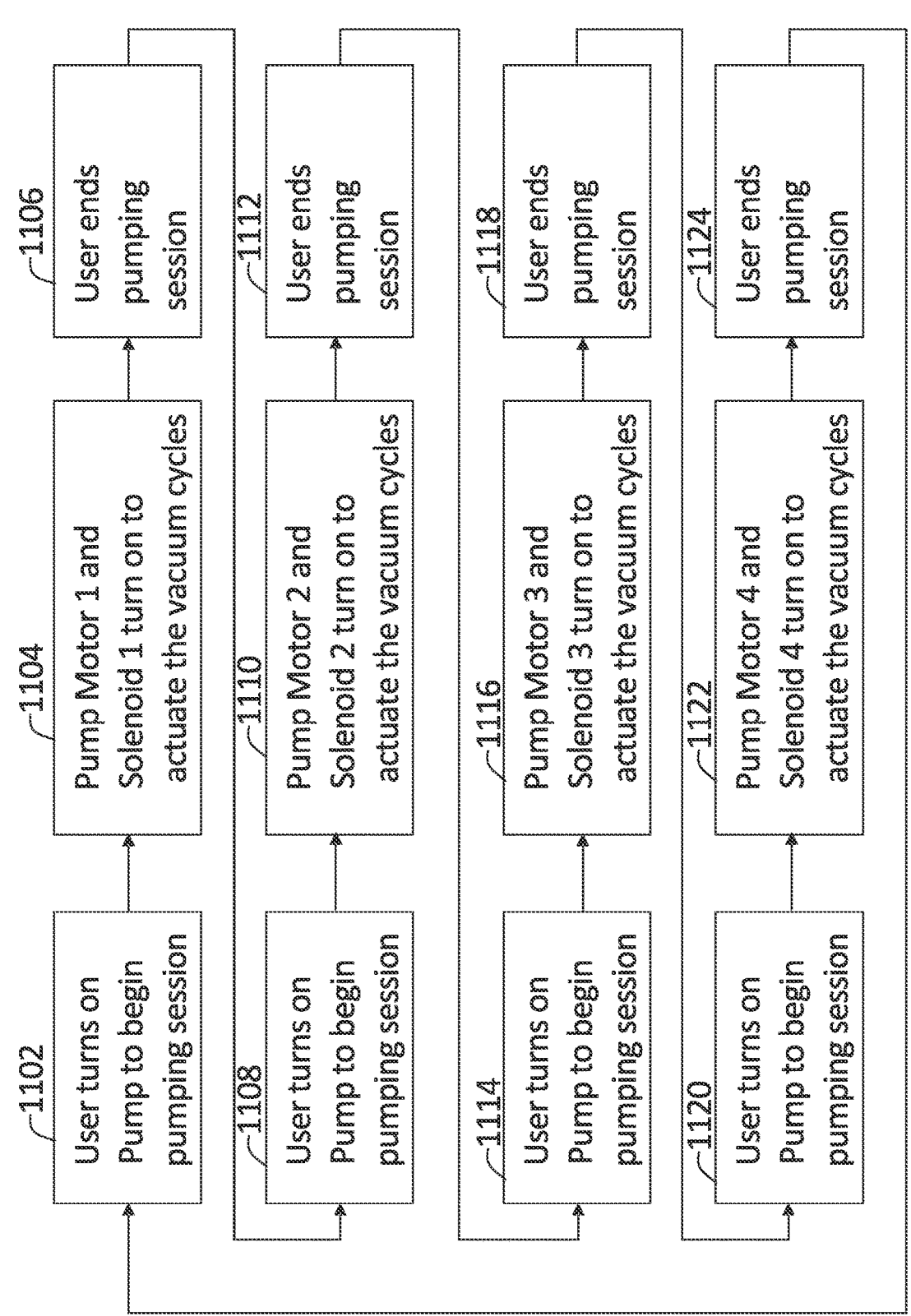
FIG. 11 depicts an exemplary flow diagram of a system turning on select components in a sequential step to preserve the useful life of components by actuating a new set of components each time a user turns on the pump.

FIG. 11 depicts an exemplary flow diagram 1100 of a system turning on select components in a sequential step to preserve the useful life of components by actuating a new set of components each time a user turns on the pump. It should also be noted that the system could check if a set of components was not performing to specifications through the action of electronic sensors and/or pressure sensors. If the set of components was not performing the system would record that fault and skip those components in the future unless they were reset. Specifically, at each initiation of a pumping session 1102, 1108, 1114, 1120, a different motor 1-4 is sequentially activated 1104, 1110, 1116, 1122 until the session is ended 1106, 1112, 1118, 1124.

Figure 12:
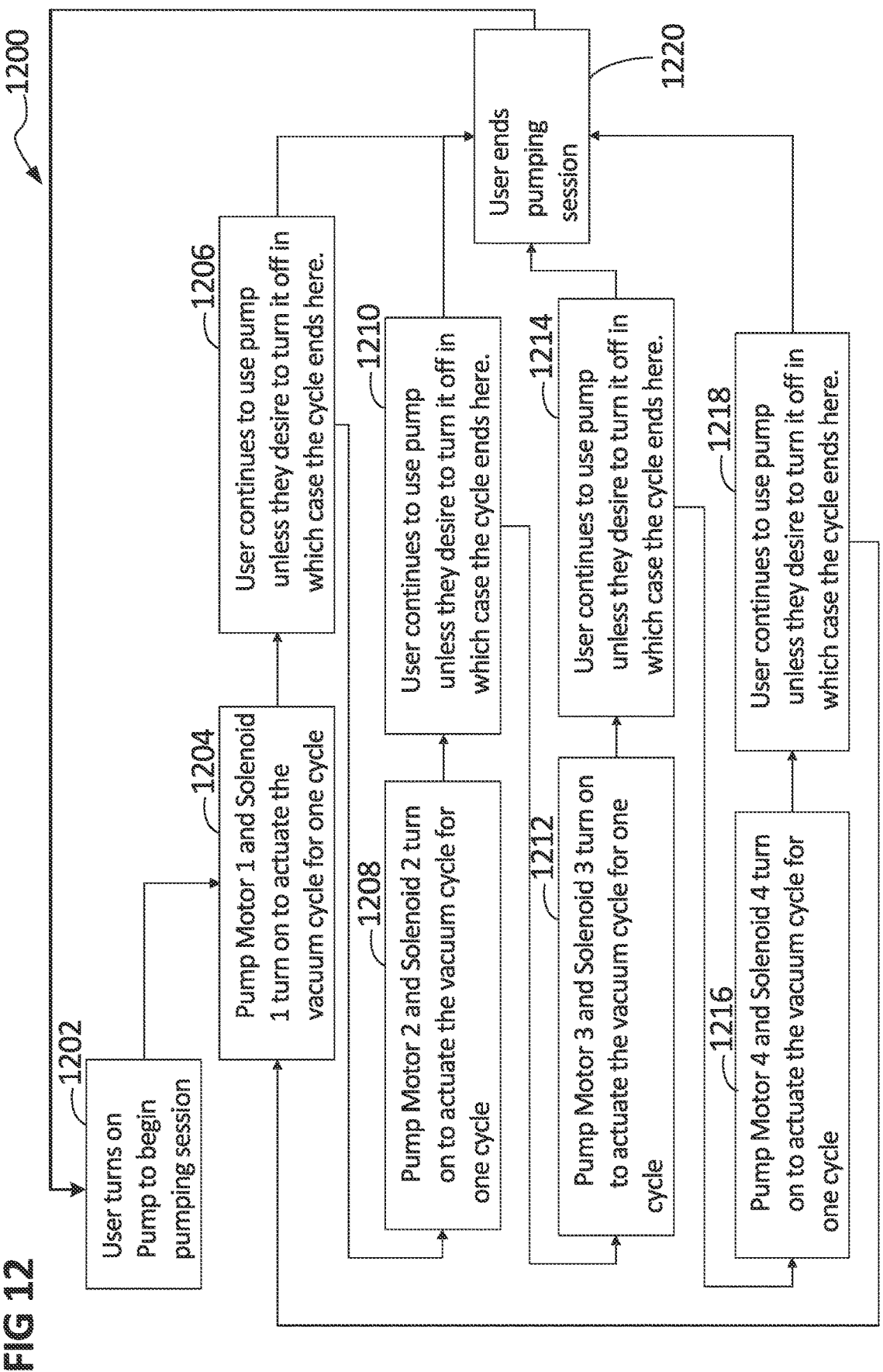
FIG. 12 depicts an exemplary flow diagram of a system turning on select components in a sequential step for each individual cycle of a pump action in order to ensure components wear evenly over an extended useful life of a pump

FIG. 12 depicts an exemplary flow diagram 1200 of a system turning on select components in a sequential step for each individual cycle of a pump action in order to ensure components wear evenly over an extended useful life of a pump. The sequential step of each cycle could result in the continued cycling of the pump by sequential components or the user could turn off the system. At the time a user turns of the system the pump could re-set to start again on component set number one or it could remember which was the last component set that it was using to start again on the next one in the series after the last one used. Additionally, if a component set is recorded to have failed by the pump it could skip those components in the series unless the user manually overrides the fault to continue using that set of components until the next fault.

Specifically, upon initiation of a pumping session 1202, each pump motor and solenoid pumps sequentially for one cycle 1204, 1208, 1212, 1216 as long as the user continues to desire pumping 1206, 1210, 1214, 1218. Pumping ceases when the user ends the pumping session 1220.

Figure 13:
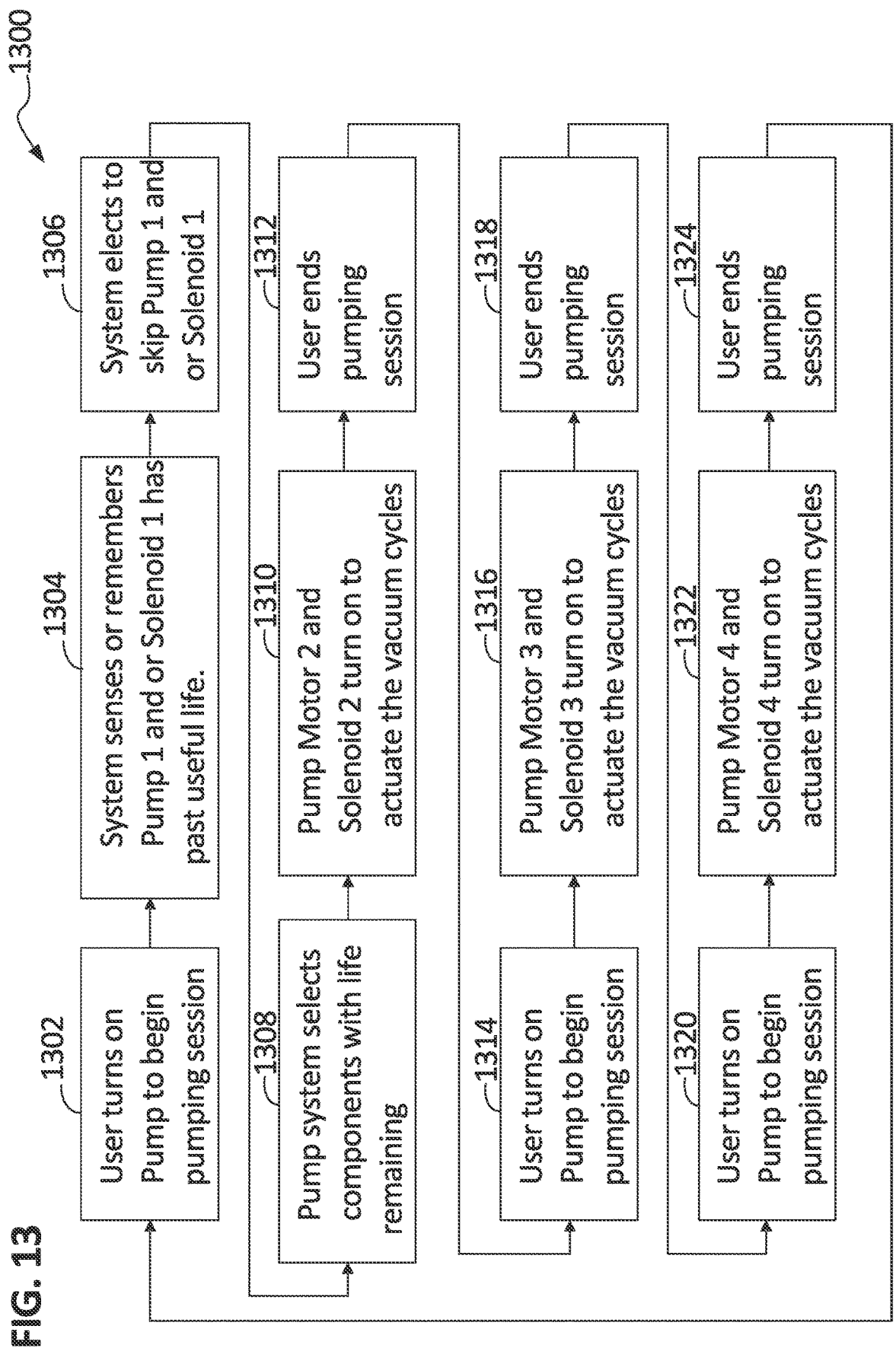
FIG. 13 depicts an exemplary flow diagram providing for a system turning on select components in a sequential step to preserve the useful life of components but first having the system check to see if components are functional and/or skipping non-functional components for the action of the pump.

FIG. 13 depicts an exemplary flow diagram 1300 providing for a system turning on select components in a sequential step to preserve the useful life of components but first having the system check to see if components are functional and/or skipping non-functional components for the action of the pump. The checking step could measure individual components or component sets such that if motor 1 failed but solenoid 1 did not fail the pump system could be configured to automatically skip both components or only motor number 1 which had failed.

Specifically, the user initiates pumping 1302, and the system identifies that pump 1 and/or solenoid 1 is past a useful life 1304 and skips that pump and/or solenoid 1306 in favor of pump 2 and/or solenoid 2 1308. Pumping continues with sequential selection of the remaining pumps and/or solenoids 1310, 1316, 1322 each time the user starts 1314, 1320 and stops 1312, 1318, 1324 a pumping session.

Figure 14:
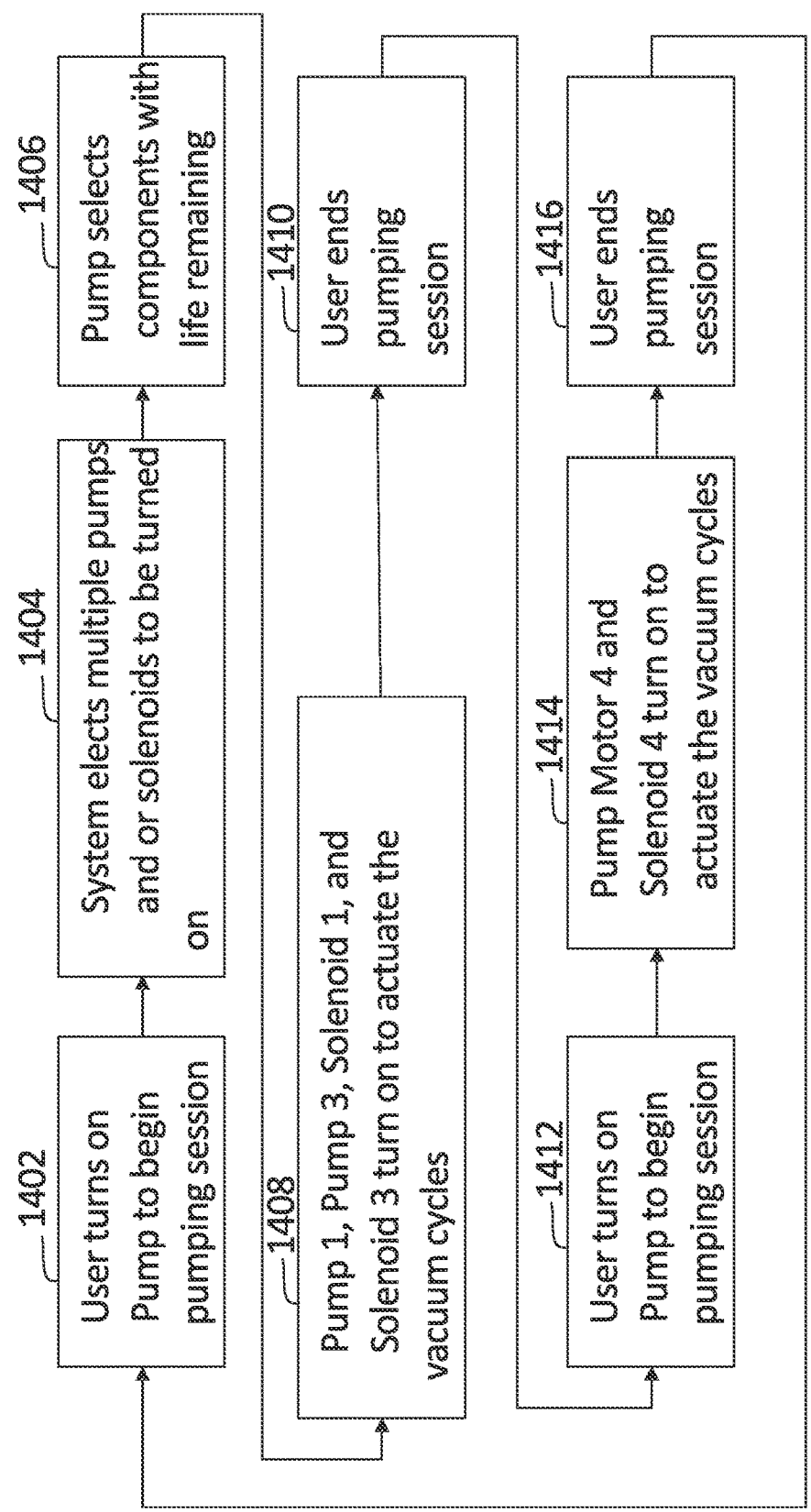
FIG. 14 depicts an exemplary flow diagram providing for a system turning on select components in a sequential step to preserve the useful life of components but also provide for options to turn on more than one set of components simultaneously to provide for additional suction or venting profile options.

FIG. 14 depicts an exemplary flow diagram 1400 providing for a system turning on select components in a sequential step to preserve the useful life of components but also provide for options to turn on more than one set of components simultaneously to provide for additional suction or venting profile options. As with other embodiments, sequential operation the system could be configured to skip components that were no longer functional. Specifically, at the start of each pumping session 1402, 1412, the system selects 1404 multiple pumps and solenoids 1404, 1406 for pumping 1408 or a single pump and solenoid 1414 until the session is stopped 1410, 1416.

Figure 15:
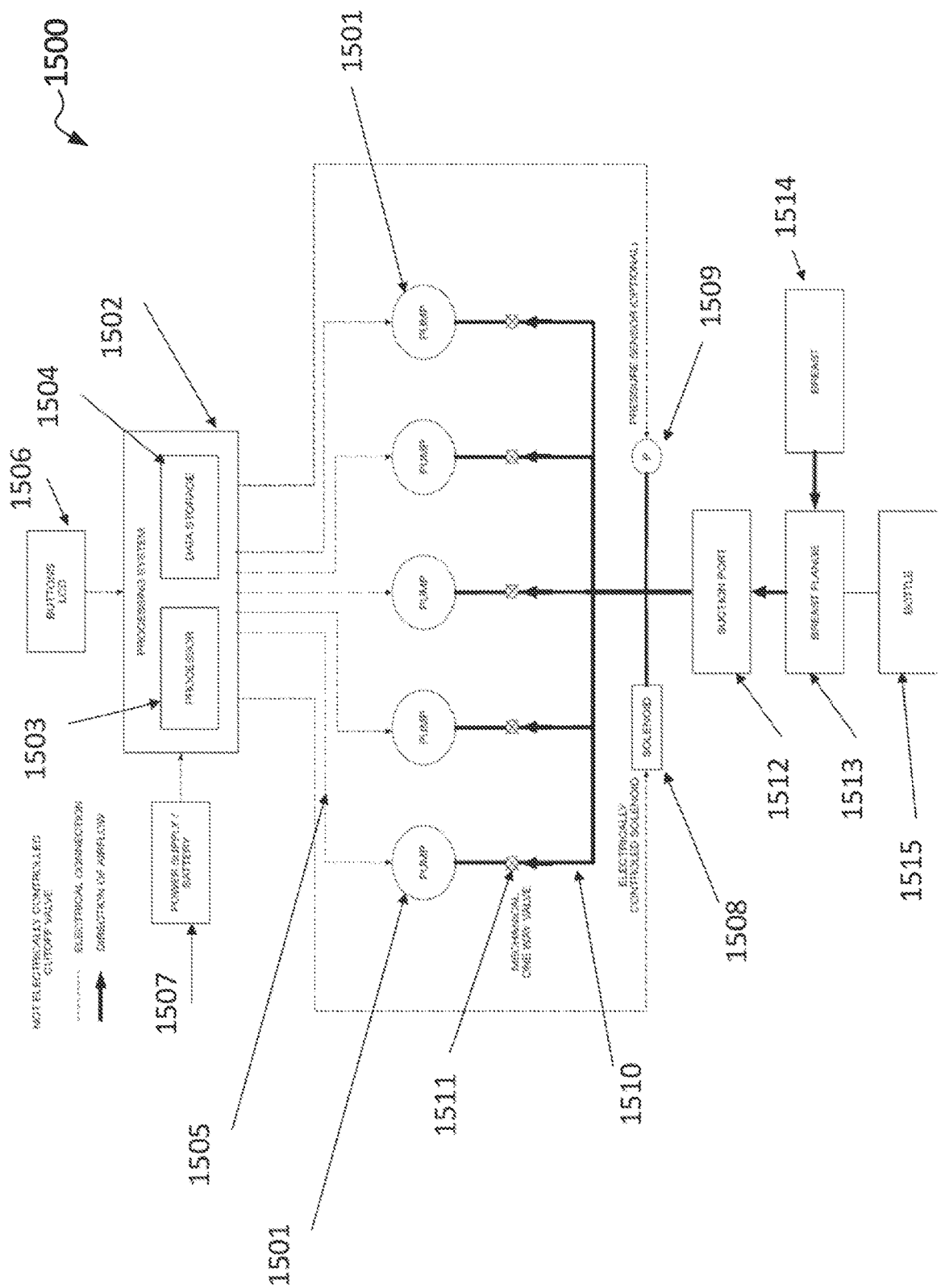
FIG. 15 depicts an exemplary schematic of a multiple breast pump systems with multiple pumps connected to the suction port via a mechanical one-way valve such that only the pumps that are active are in fluid connection to the suction port.

FIG. 15 depicts an exemplary breast pump schematic 1500 with multiple pump motors 1501 containing at least one suction diaphragm that are connected electrically by wires 1505 to a central processing system 1502 that contains a data storage 1504 and data processing units 1503. The system also may have a means for user interaction or display 1506, battery or power supply 1507, solenoid(s) 1508, and/or pressure sensors 1509. Each pump is only in connection with a fluid air suction path 1510 if it is active due to a mechanical restriction or one way valve 1511 which is only open when to connect a pump 1501 to the suction air fluid path when the pump 1501 is turned on by the processing system 1502. The pump system may also contain one or more suction ports 1512 as a source of suction for a breast shield flange system 1513 that accepts a breast 1514 to extract milk through at least partially by the action of suction of one or more pumps 1501 communicating vacuum through the flow path 1510 if they are active such that the mechanical valve 1511 allows the pumps to be in fluid communication with the flow path 1510. Milk extracted from the breast 1514 is received into the flange 1513 and then deposited into a storage container like a bottle 1515.

Figure 16:
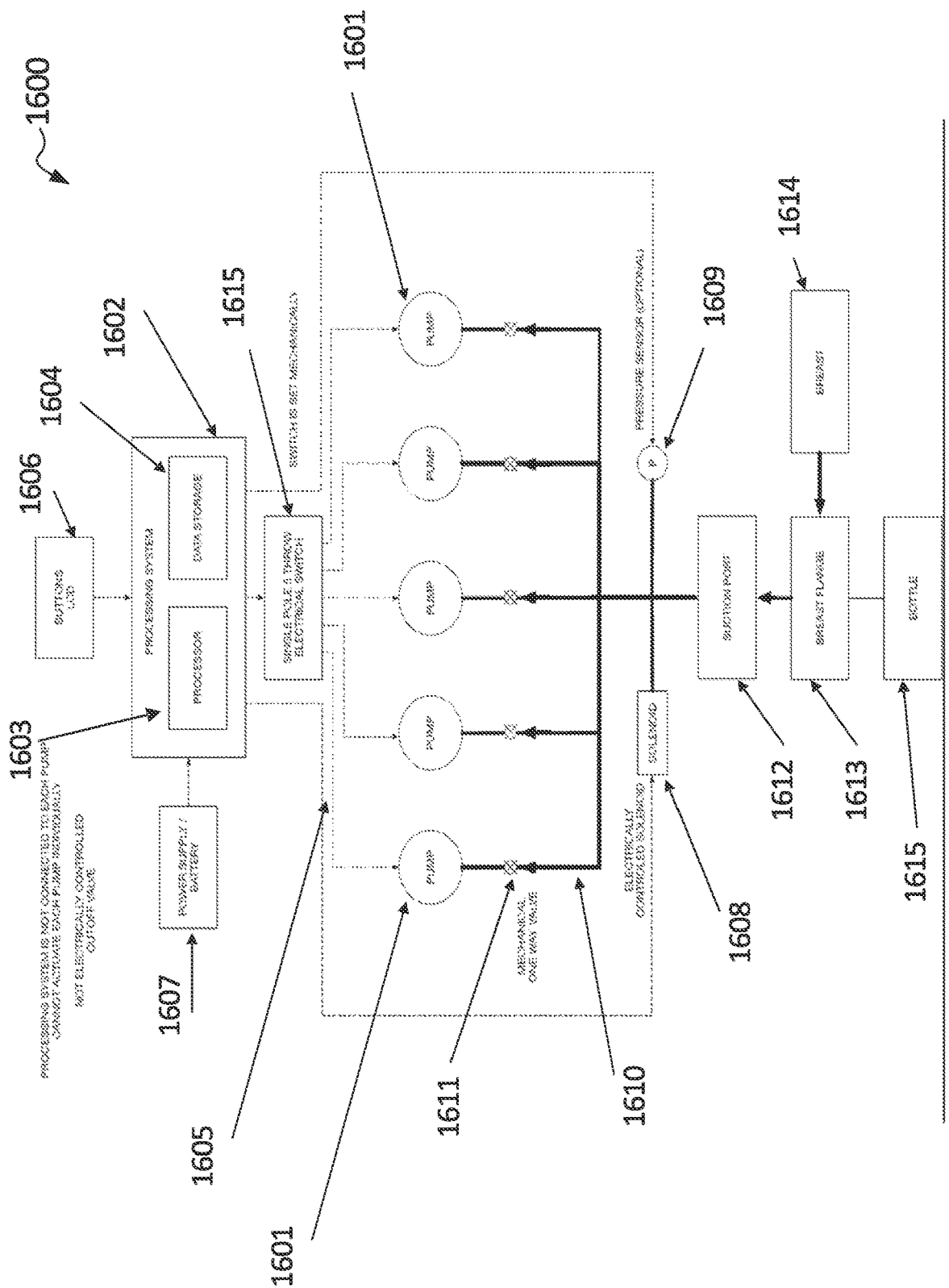
FIG. 16 depicts an exemplary schematic of a multiple pump breast pump system where the pumps are not individually connected to the processing system such that the end user will manually move an electrical switch to determine which motor is controlled by the processing system such that only one pump is active at one time.

FIG. 16 depicts an exemplary breast pump schematic 1600 with multiple pump motors 1601 containing at least one suction diaphragm that are connected electrically by wires 1605 to a central processing system 1602 that contains a data storage 1604 and data processing units 1603. The system also may have a means for user interaction or display 1606, battery or power supply 1607, solenoid(s) 1608, and/or pressure sensors 1609. Each pump may or may not only be in connection with a fluid air suction path 1610 if it is active due to a mechanical restriction or one way valve 1611 which is only open when to connect a pump 1601 to the suction air fluid path when the pump 1601 is turned on by the processing system 1602. In addition, the pumps 1601 are not individually connected to the processing system 1602 in this embodiment.

The end user will manually move at least one electrical switch 1615 which can be a throw switch, button slider, or similar, to determine and isolate which motor or motors 1601 is controlled by the processing system 1602. In this scenario, only one pump 1601 is active at one time unless the user desires to use the throw switch or switches 1615 to active more than one pump 1601. If the pressure sensor 1609 is present, the system can direct the user to adjust the switch 1615 to control a working pump 1601 or skip over a broken pump 1601. If the pressure sensor 1609 is not present, the user may also be provided with the ability to notify and record in the processing system 1602 through a user interface 1606 capability of a failed pump 1601, and the processing system 1602 will direct the user to adjust the switch 1615 to control a working pump 1601 in any future use scenario when the failed pump 1601 is requested to be used.

The pump system may also contain one or more suction ports 1612 as a source of suction for a breast shield flange system 1613 that accepts a breast 1614 to extract milk through at least partially by the action of suction of one or more pumps 1601 communicating vacuum through the flow path 1610 if they are active such that the mechanical valve 1611 allows the pumps to be in fluid communication with the flow path 1610. Milk extracted from the breast 1614 is received into the flange 1613 and then deposited into a storage container like a bottle 1616.

Figure 17:
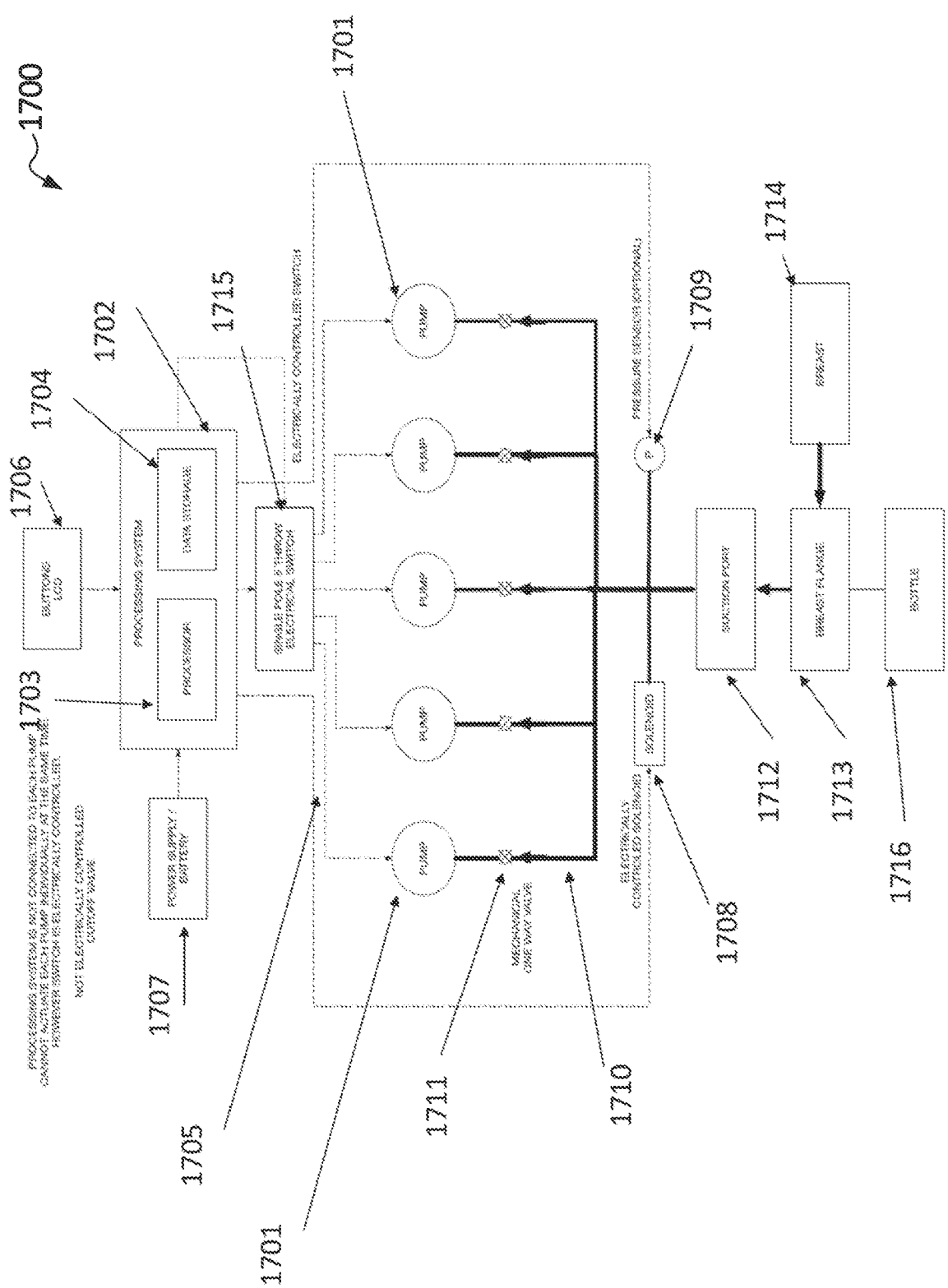
FIG. 17 depicts an exemplary high reliability breast pump schematic with multiple pump motors containing at least one diaphragm such that an electrical switch can be controlled electronically as a relay so the processing system can control which pump is on to ensure only one pump can be on at a time.

FIG. 17 depicts an exemplary breast pump schematic 1700 with multiple pumps 1701 containing at least one suction diaphragm that are connected electrically by wires 1705 to a central processing system 1702 that contains a data storage 1704 and data processing units 1703. The system also may have a means for user interaction or display 1706, battery or power supply 1707, solenoid(s) 1708, and/or pressure sensors 1709. Each pump may or may not only be in connection with a fluid air suction path 1710 if it is active due to a mechanical restriction or one way valve 1711 which is only open when to connect a pump 1701 to the suction air fluid path when the pump 1701 is turned on by the processing system 1702. In addition, the pumps 1701 are not individually connected to the processing system 1702 in this embodiment.

The end user will manually move at least one electrical switch 1715 that can be controlled electronically such as a relay 1715 to determine and isolate which pump or pumps 1701 is controlled by the processing system 1702. In this scenario, only one pump 1701 is active at one time unless the user desires to provide input to the system 1702 to throw switch or switches 1715 to active more than one pumps 1701. If the pressure sensor 1709 is present, the system can adjust the switch 1715 to control a working pump 1701 or skip over a broken pump 1701. If the pressure sensor 1709 is not present, the user may also be provided with the ability to notify and record in the processing system 1702 through a user interface 1706 capability of a failed pump 1701, and the processing system 1702 will direct the system to adjust the switch 1715 to control a working pump 1701 in any future use scenario when the failed pump 1701 is requested to be used.

The pump system may also contain one or more suction ports 1712 as a source of suction for a breast shield flange system 1713 that accepts a breast 1714 to extract milk through at least partially by the action of suction of one or more pumps 1701 communicating vacuum through the flow path 1710 if they are active such that the mechanical valve 1711 allows the pumps to be in fluid communication with the flow path 1710. Milk extracted from the breast 1714 is received into the flange 1713 and then deposited into a storage container like a bottle 1716.

Figure 18:
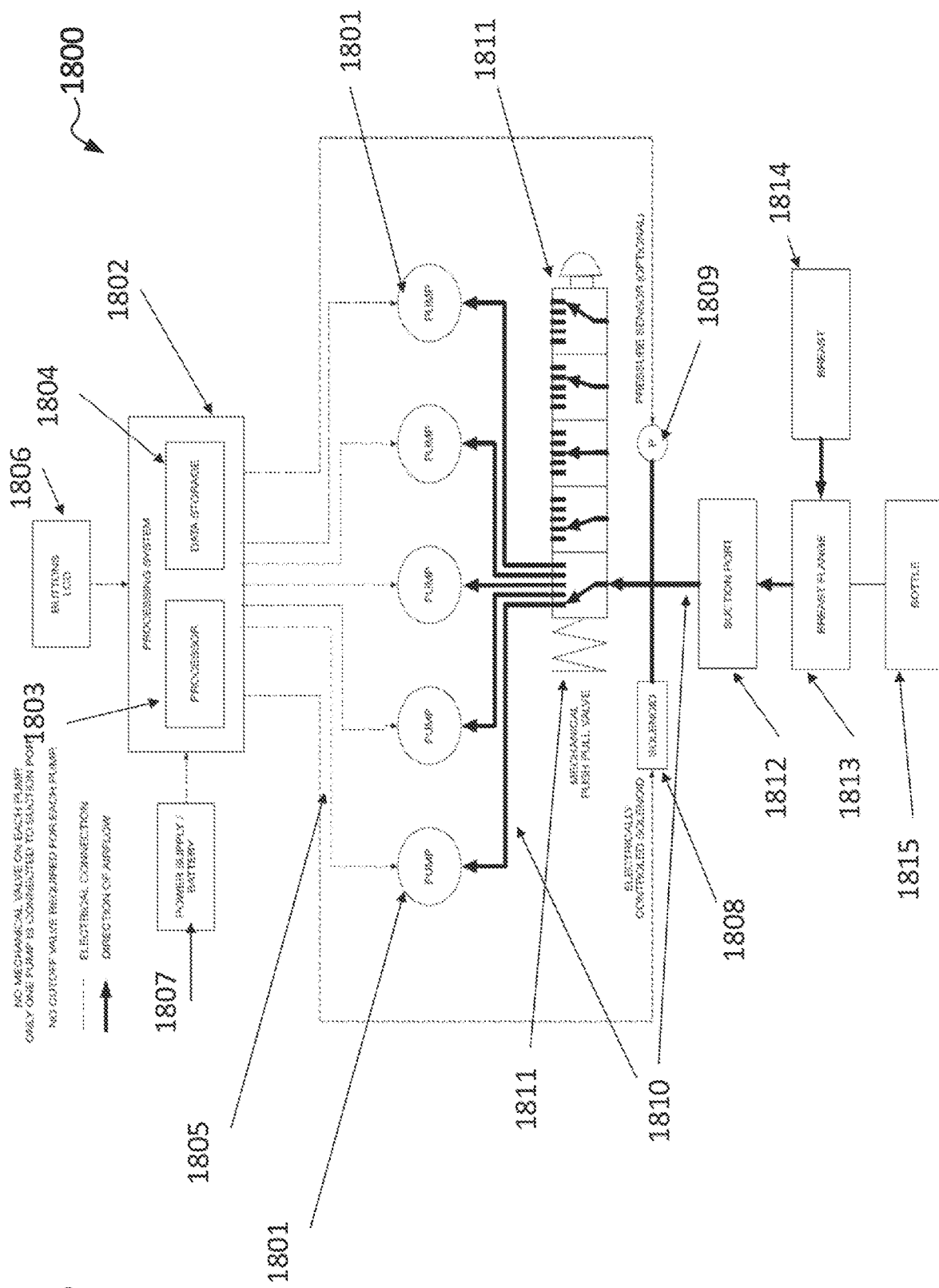
FIG. 18 depicts an exemplary breast pump system with multiple redundant components such that the pumps are individually controlled by the processing system but the pumps are not directly connected to the suction port unless a mechanical push/pull valve is placed in the right configuration to select which motor forms the fluid connection to the suction port.

FIG. 18 depicts an exemplary breast pump schematic 1800 with multiple pump motors 1801 containing at least one suction diaphragm that are connected electrically by wires 1805 to a central processing system 1802 that contains a data storage 1804 and data processing units 1803. The system also may have a means for user interaction or display 1806, battery or power supply 1807, solenoid(s) 1808, and/or pressure sensors 1809. Each pump is only in connection with a fluid air suction path 1810 if it is active due to a user activated mechanical valve 1811 such as a slide valve, rotary valve, pin valve, button turn valve, push/pull valve, or any other valve or piping system which would be actuated by the user to create a selective fluid pathway 1810 between one or more pumps 1801 and a suction port 1812 by the manual action of the user which is only open when to connect a pump 1801 to the suction air fluid path when the pump 1801 is turned on by the processing system 1802. The pump system may also contain one or more suction ports 1812 as a source of suction for a breast shield flange system 1813 that accepts a breast 1814 to extract milk through at least partially by the action of suction of one or more pumps 1801 communicating vacuum through the flow path 1810 if they are active such that the mechanical valve 1811 allows the pumps to be in fluid communication with the flow path 1810.

Milk extracted from the breast 1814 is received into the flange 1813 and then deposited into a storage container like a bottle 1815. In the event that the pressure sensor 1809 detects that one or more pumps 1801 is no longer performing well or has failed then the system 1802 could elect to actuate a motor which blocks some of the pumps 1801 from being receptive to a connection path 1810 that would be created by the valve 1811 being placed in a specific configuration. Alternatively or in addition, warning lights, sounds, or other signals could be communicated on the display system 1806 to the user to indicate which configuration the pump needs to be placed in to work well in any case of a deficient pump 1801.

Figure 19:
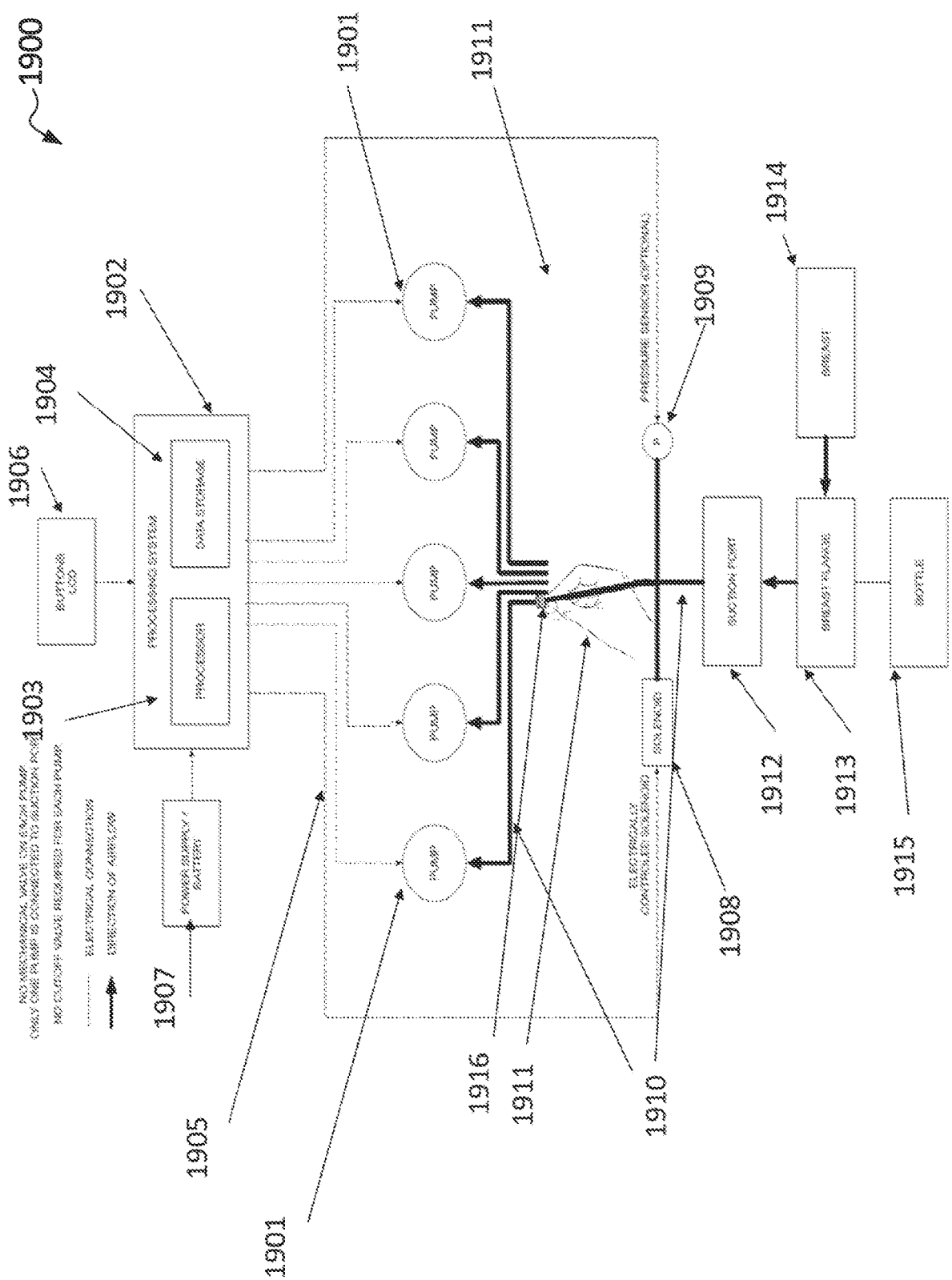
FIG. 19 depicts an exemplary breast pump system with multiple redundant components such that a user would physically connect or disconnect one or more pumps by hand using suction tubing with connectors to ensure only the right number of pump or pumps the user desires are in line with the system to be used at any one time.

FIG. 19 depicts an exemplary breast pump schematic 1900 with multiple pump motors 1901 containing at least one suction diaphragm that are connected electrically by wires 1905 to a central processing system 1902 that contains a data storage 1904 and data processing units 1903. The system also may have a means for user interaction or display 1906, battery or power supply 1907, solenoid(s) 1908, and/or pressure sensors 1909. Each pump is only in connection with a fluid air suction path 1910 if it is active due to a user creating a connection between tubing manually 1911 to create a selective fluid pathway 1910 between one or more pumps 1901 and a suction port 1912 by the manual action of the user which is only open when to connect a pump 1901 to the suction air fluid path when the pump 1901 is turned on by the processing system 1902. The pump system may also contain one or more suction ports 1912 as a source of suction for a breast shield flange system 1913 that accepts a breast 1914 to extract milk through at least partially by the action of suction of one or more pumps 1901 communicating vacuum through the flow path 1910 if they are active such that the user making a connection of the line 1911 allows the pumps to be in fluid communication with the flow path 1910.

Milk extracted from the breast 1914 is received into the flange 1913 and then deposited into a storage container like a bottle 1915. In the event that the pressure sensor 1909 detects that one or more pumps 1901 is no longer performing well or has failed then the system 1902 could elect to actuate a motor which blocks some of the pumps 1901 from being receptive to a connection path 1910 that would be created by manual line connection 1911 being placed in a specific configuration and the suction line connector 1916 making a connection between the pumping line and the suction port lines 1910. Alternatively or in addition, warning lights, sounds, or other signals could be communicated on the display system 1906 to the user to indicate which configuration the pump needs to be placed in to work well in any case of a deficient pump 1901.

Figure 20:
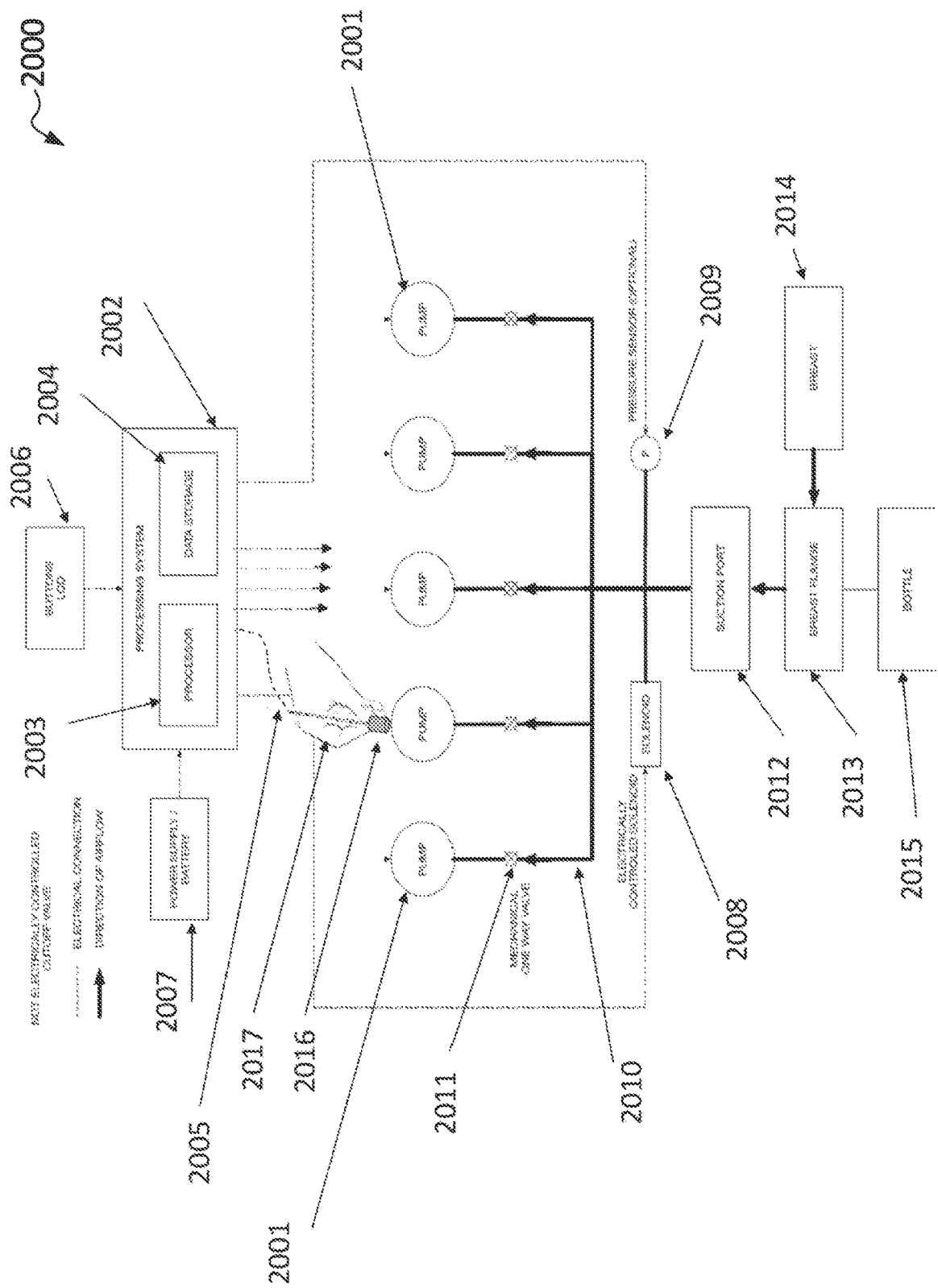
FIG. 20 depicts an exemplary breast pump system with multiple redundant components such that a user would physically connect or disconnect one or more pumps by hand using electrical wiring connections with removable/reusable connectors to ensure that only the desired pump or pumps is on at any one time as desired by the user.
Figure 23B:
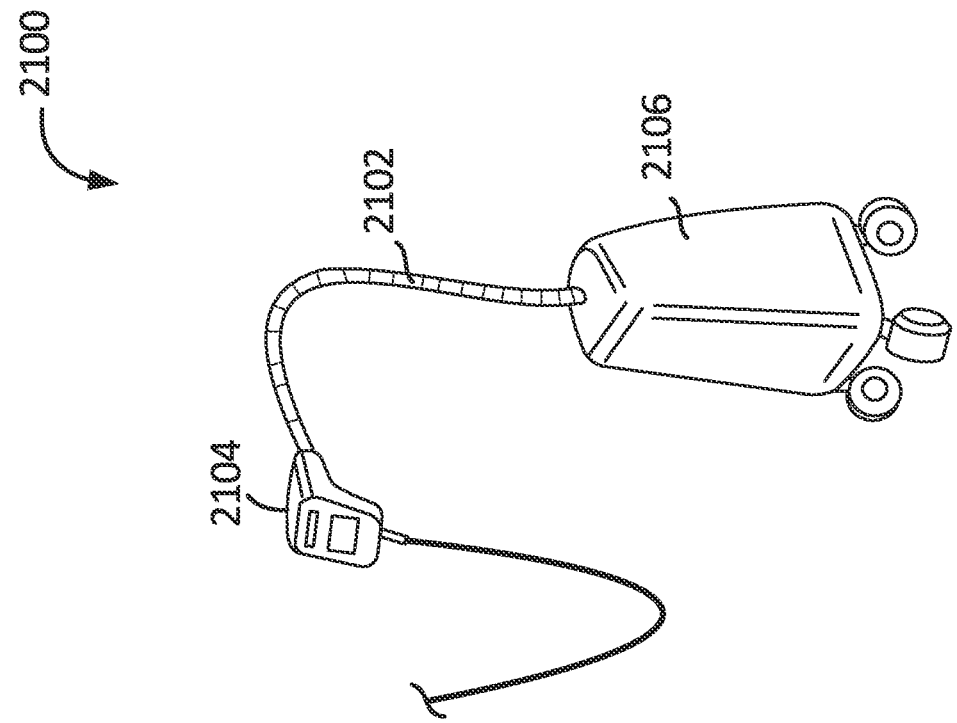
FIGS. 23A and 23B depict exemplary side views of proposed embodiments of a breast pump with a pivoting hinge pole that connects a control unit and suction tubing interactive portion with a base unit containing a center of mass and or the vacuum mechanism and or battery unit or power supply.
Figure 23A:
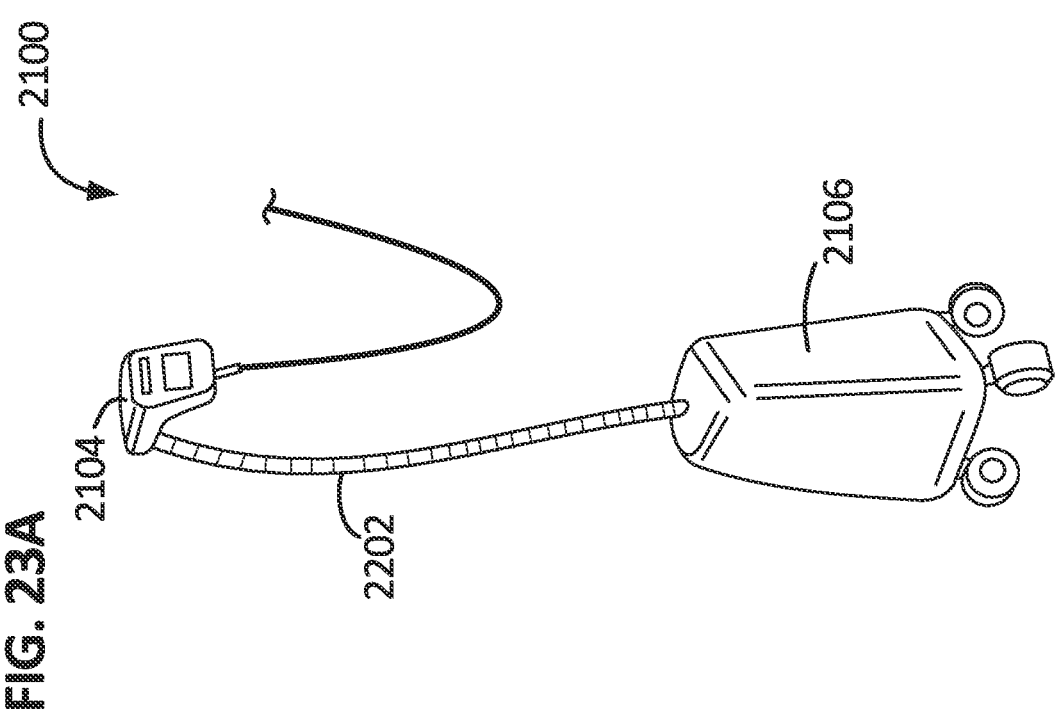
Figure 24A:
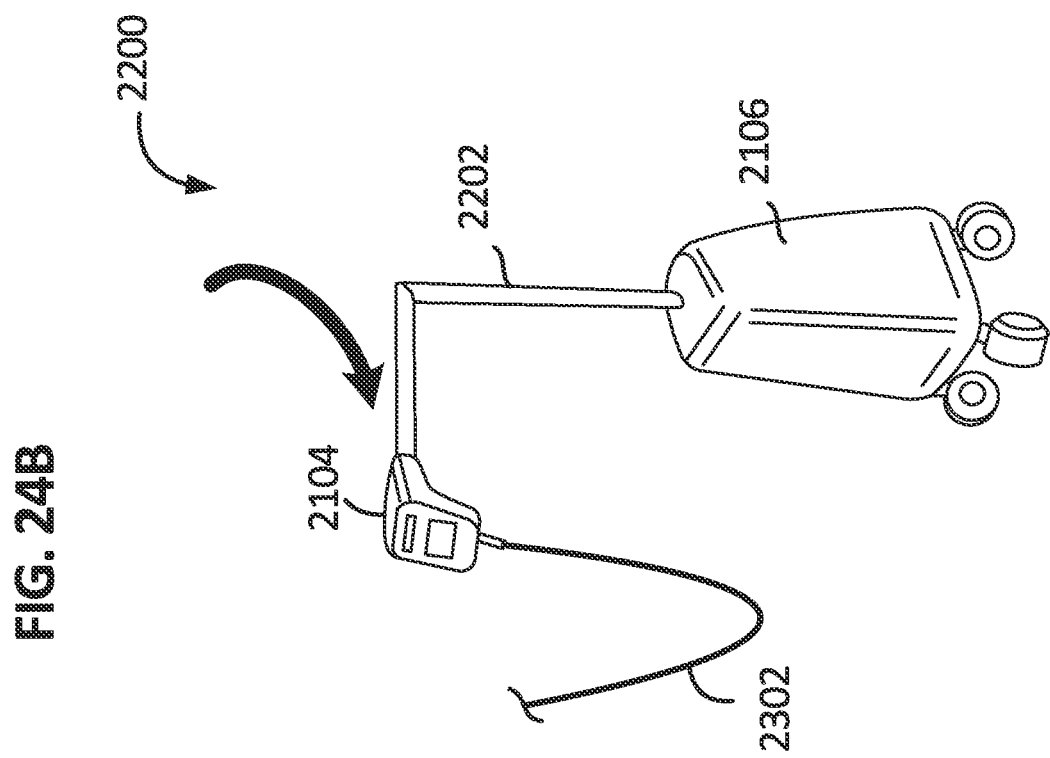
FIGS. 24A and 24B depict exemplary side views of proposed embodiments of a breast pump with a snake like or bendable semi ridged and partially flexible tubing pole that allows for a power conduit and or suction conduit tube to run through it and be used by a user along with a control unit at a variety of heights and dimensions.
Figure 24B:
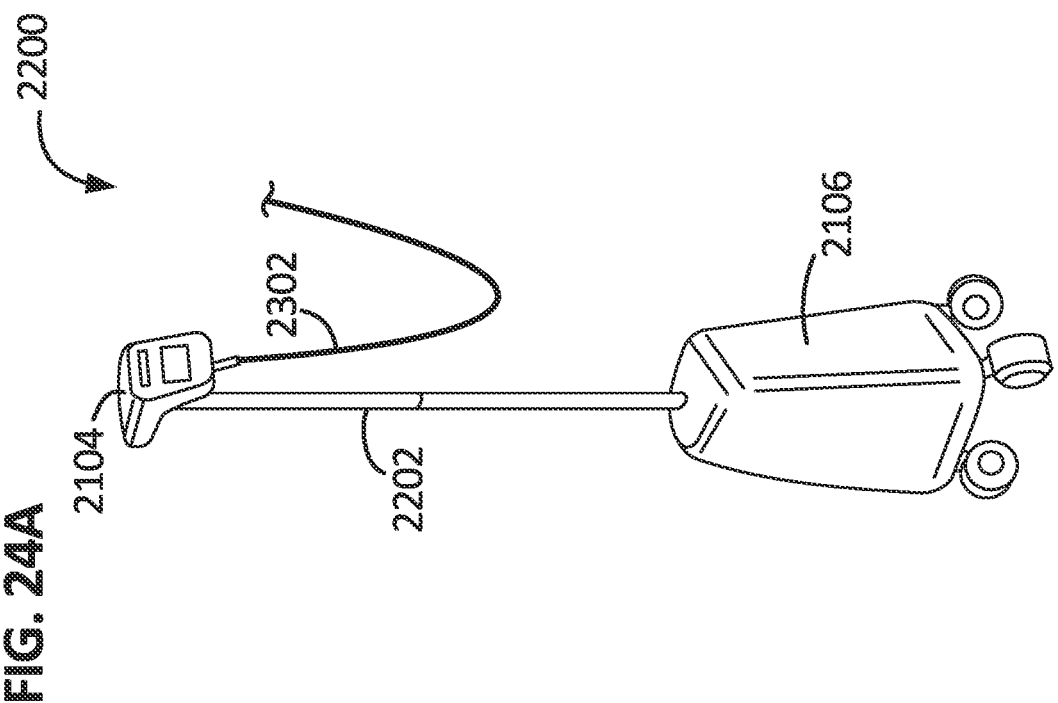

FIG. 20 depicts an exemplary breast pump schematic 2000 with multiple pump motors 2001 containing at least one suction diaphragm that are connected electrically by wires 2005 to a central processing system 2002 that contains a data storage 2004 and data processing units 2003. The system also may have a means for user interaction or display 2006, battery or power supply 2007, solenoid(s) 2008, and/or pressure sensors 2009. Each pump is only active to create a vacuum pressure in the fluid air suction path 2010 if it is active due to a user manually 2017 creating an electrical connection 2016 between the processing system 2002 and the chosen pump or pumps 2001 by at least a partial manual action of the user. The pump system may also contain one or more isolation valves 2011 that may be mechanically or electrically activate to provide connection between the pump or pumps 2001 that are activated with the action of the user plugging a plug 2016 in the power circuit. The pump system may also contain one or more suction ports 2012 as a source of suction for a breast shield flange system 2013 that accepts a breast 2014 to extract milk through at least partially by the action of suction of one or more pumps 2001 communicating vacuum through the flow path 2010.

Milk extracted from the breast 2014 is received into the flange 2013 and then deposited into a storage container like a bottle 2015. In the event that the pressure sensor 2009 detects that one or more pumps 2001 is no longer performing well or has failed then the system 2002 could elect to close off the plug port 2016 such that the user would not be able to use that motor 2001 when it is unplugged. Alternatively or in addition, warning lights, sounds, or other signals could be communicated on the display system 2006 to the user to indicate which configuration the pump needs to be placed in to work well in any case of a deficient pump 2001.

Referring now generally to FIGS. 21-50, other disclosed embodiments include devices where the control unit may be located remotely (e.g., moved some distance away) from at least a portion of a main part of a breast pump configuration. Such embodiments may or may not include multiple motors as described above.

In some embodiment, this distance is created by a mechanism having a breast pump unit at a lower center of gravity than a movable control unit. In other embodiments, this is accomplished by the vacuum suction being part of a secondary device or structure that the control unit can connect to and be movable in space relative to an outlet suction portion via a tube. In yet other embodiments, the control unit and pump are housed in one unit but that unit is only one part of a greater system which includes a docking station such that the user could move part of the pumping mechanism to a different area of space without needing to be connected physically to this other main part of the pumping system.

This disclosure provides multiple different embodiments such that a user could use adjust the position of major parts of the pumping system in space relative to each other with ease to facilitate easier workflows within the breast pumping regime.

For example, in the case of a compact pump that is able to be rolled and the control unit for the pump can be adjusted to different heights that would enable the user to store the pump on wheels under a NICU incubator in a tight space while pumping. This may better facilitate a mom to be able to pump at the NICU bedside instead of being sequestered into a separate room.

In another example, the same mom could use a different version of the proposed design to connect directly to the source of in house hospital suction next to the NICU incubator bed such that the mom would not have any type of physical unit blocking the floor and the source of suction would be comprised at a different location than the NICU but facilitated to the delivery point through tubing in the wall and the control unit device and pressure modulator that the mom was using.

In another embodiment a docking station could be stored in the same or different location to a NICU bedside or even as part of a storage compartment on a NICU incubator so that a pump could be removed or checked out and used by the mom with ease without needing the rolling trolley that moms have to use today which take up lots of space in the NICU. Additionally, a pump could be built into the bottom area of a NICU incubator itself or attached to the NICU incubator by hanging down from it or clicking onto it and that would allow mom to pump directly next to baby without additional space required.

FIGS. 21A, 21B, 23A, 23B show an example breast pump 2100 in which where a mom could either be laying down, sitting, hunched over, or standing using a snake like bendable flexible control unit arm 2102 which allows a control unit 2104 to be moved at any different position away from a pump housing 2106 without the housing necessarily having to move. A mom would use a breast shield flange, freemie cup, primo lacto, or other milk capture collection mechanism in order to contain the milk expressed from the breast by at least partially applying a source of suction to the front region of the breast. This source of suction would express the milk in combination or without the combination of a massaging effect from a secondary compression device or the action of the user or other person.

Specifically, the flexible pole 2102 allows a user to configure the control unit 2104 to be at various heights and positions across the X Y Z dimensions. In this embodiment, the control unit 2104 is physically connected to a mobile vacuum source that is comprised in the unit itself but the connected such that the control unit 2104 can move in many different physical locations away or towards the main vacuum setup.

The traditional breast pump mechanism would be contained in the pump housing 2106 of the unit including a solenoid, source of power, and a vacuum pump with one or more diaphragms and one or more motors or other components as desired for longevity of the device. Various suction waveforms of reducing the pressure could be used including a random waveform pattern and or vibration waveforms. These waveforms could be applied to any embodiment disclosed herein.

FIGS. 22A, 22B, 24A, 24B describe a similar breast pump 2200 with a pivoting arm 2202 between the control unit 2104 and the base source of vacuum. The rotation allows for movement of the pivoting arm 2202 with the control unit 2104 and a suction tubing 2302 at the top for connection to a breast pump collection unit such as a breast shield or flanges.

The pump 2200 may or may not also contain wheels, rollers, sliders, or other mechanisms to make it easier for a user to move it including but not limited to additional handles, pull strings, push poles, or other structural features that would make it easy to transport. In addition, the breast pump housing 2106 may or may not also contain motorized wheels and proximity sensors that, through the action of the control unit 2104, could be used to summon the pump 2200 to a specific room or return a storage pump to a room after a pumping session has concluded. Finally, the wheels can include brakes that allow the pump 2200 to be immobilized when in a desired position.

The pump housing 2106 could also contain a weight that would be purposefully placed here to make the bottom heavier so it would not be prone to tip over as users would push it along with the wheels 2110. In addition, a combination of a snake or flexible arm with a pivoting arm may or may not be done to facilitate easier ergonomic movement.

Figure 25A:
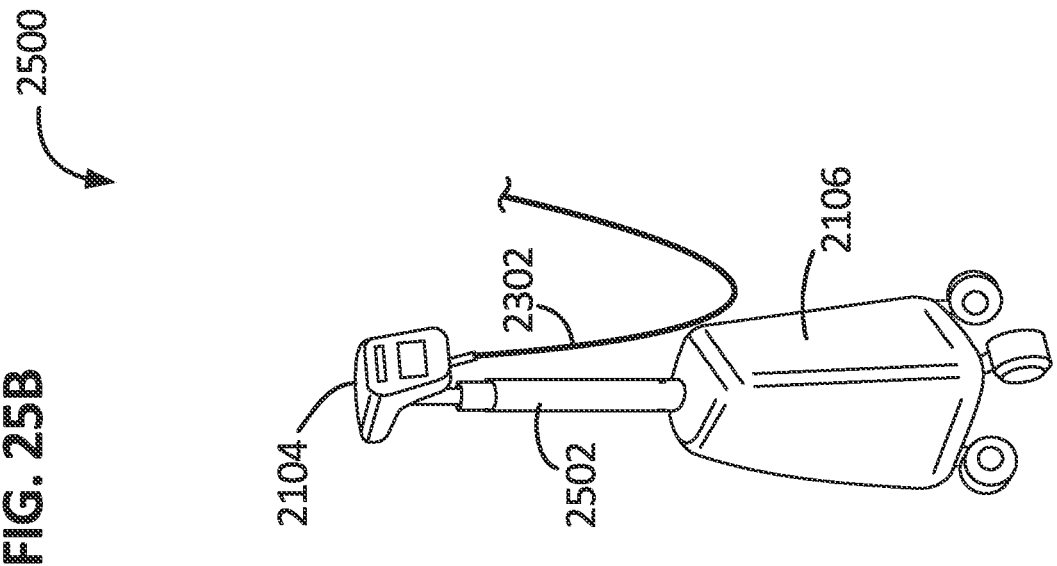
FIGS. 25A and 25B depict exemplary side views of proposed embodiments of a breast pump where the pump can be made to be extremely compact by telescoping downwards to a low center of mass on the pump where a control unit is perched near the top of a telescoping pole.
Figure 25B:
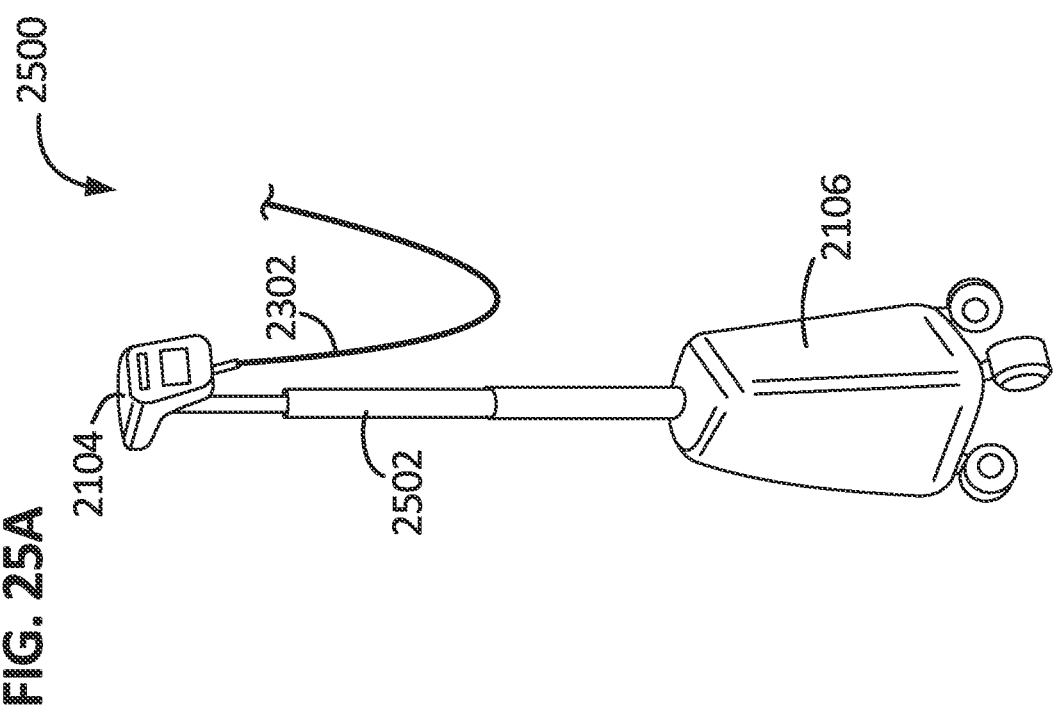

FIGS. 25A and 25B demonstrate a pump 2500 with a telescoping pole 2502 design where a user could configure the height of the control unit to be at varying positions if the user was laying down, sitting, hunched over, or standing.

Figure 26:
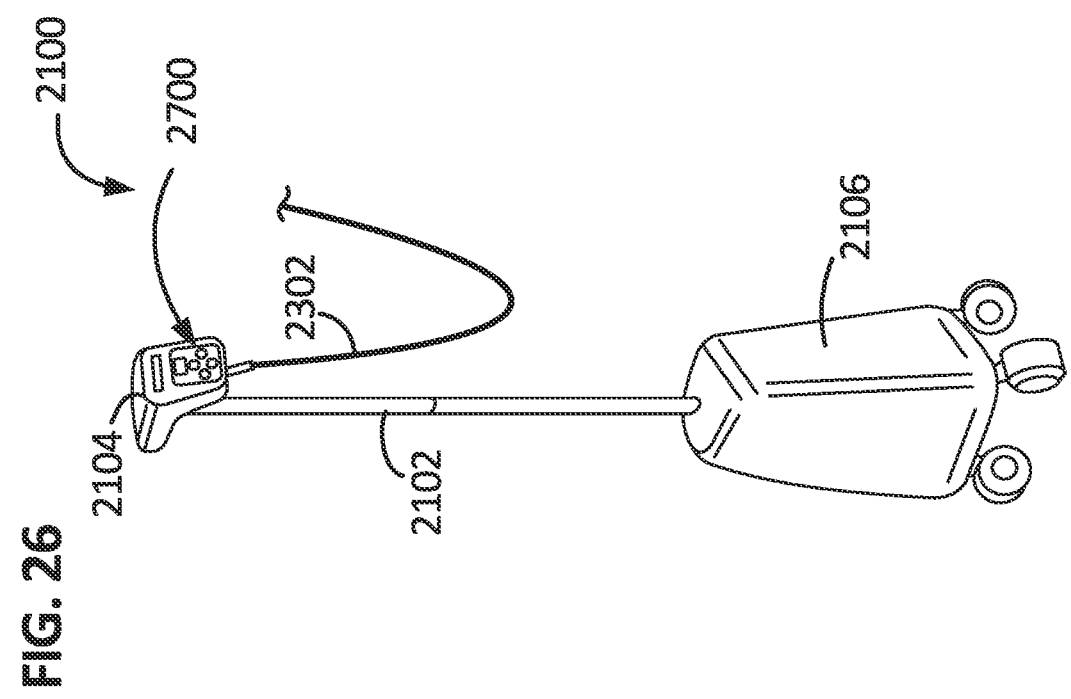
FIG. 26 depicts an exemplary control unit on top of a breast pump for one or multiple users with wheels or other rolling apparatuses that would allow the user to easily move the device before after or during use.

FIG. 26 depicts the exemplary control unit 2104 in an upright position such that the suction tube 2302 could also be flexible extending from the control unit 2104 to reach a user and connect to breast shields and flanges that would allow milk to be captured through the pump 2100 into a baby bottle or milk storage container such as but not limited to a milk storage bag.

Figure 27:
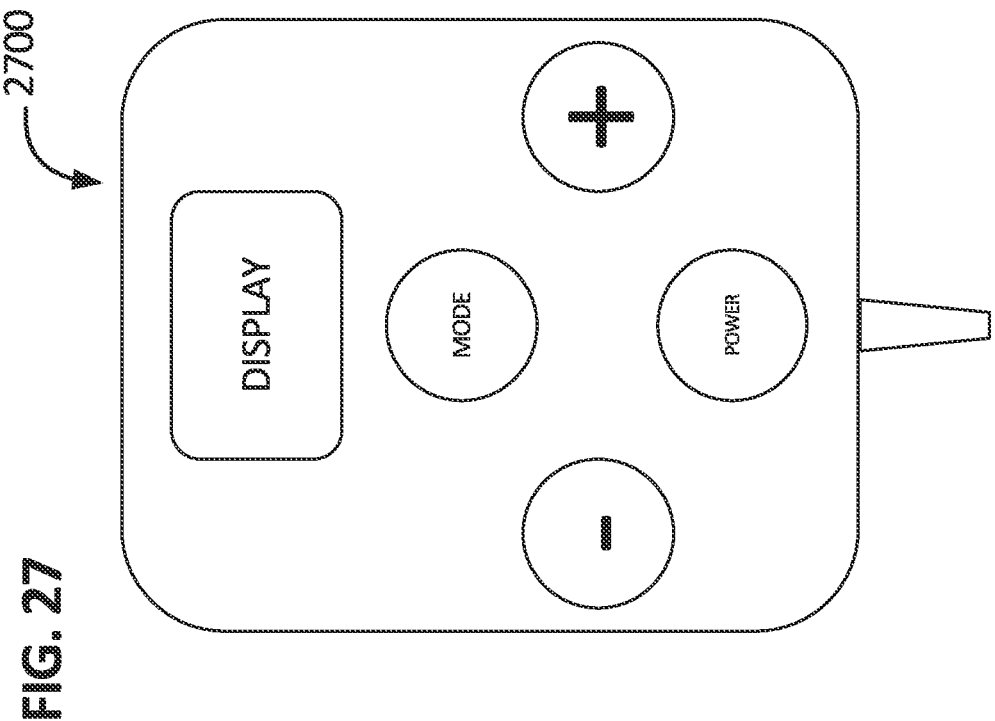
FIG. 27 depicts an exemplary display feature on the control unit of a breast pump device such that the control unit could have its position adjusted by the user at a different position away from a core pump unit which would remain stationary and that the user could activate the control unit with a variety of buttons or mechanisms as the system would display feedback.

FIG. 27 depicts an embodiment of an interface unit 2700 of the control unit 2104. In this example, the interface unit 2700 has a plus button (to increase pressure), a minus button (to decrease pressure), a mode button (to select a desired pumping mode), and a power button along with a display. This unit 2700 could also have accelerometer chips built in such that if a user tapped the phone onto the display unit and the phone was linked to the surrounding Bluetooth environment the pump would be able to compare the timestamp of the accelerometer trigger from the phone and the pump in order to know which phone to link to which pump.

Figure 28:
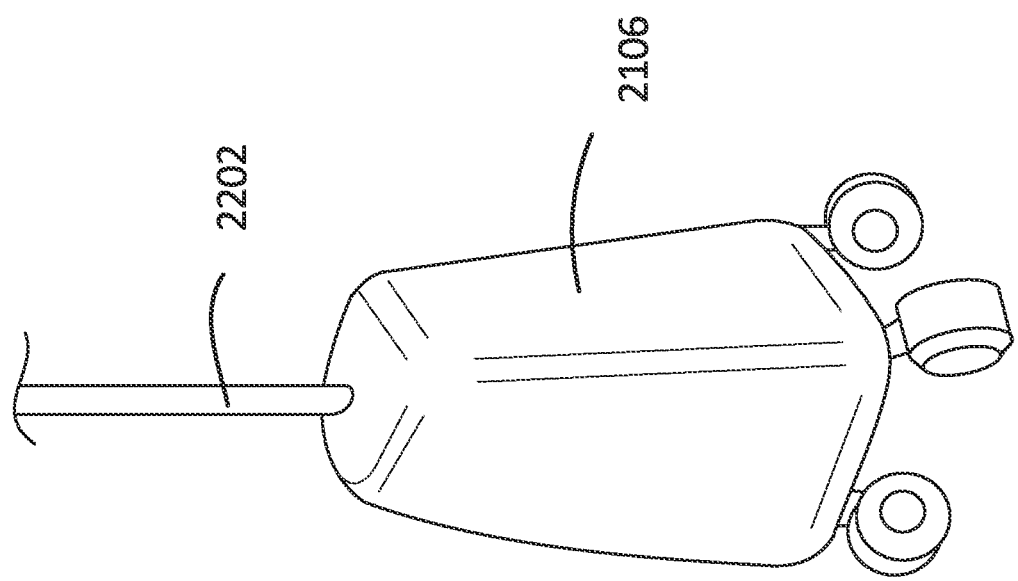
FIG. 28 depicts an exemplary side view of the base mechanism of a breast pump with a varied position control unit such that the base unit would have a vacuum pump and a mechanism to power that vacuum pump as well as the option to power the control unit if the control unit and or pump system is not battery powered separately.
Figure 29:
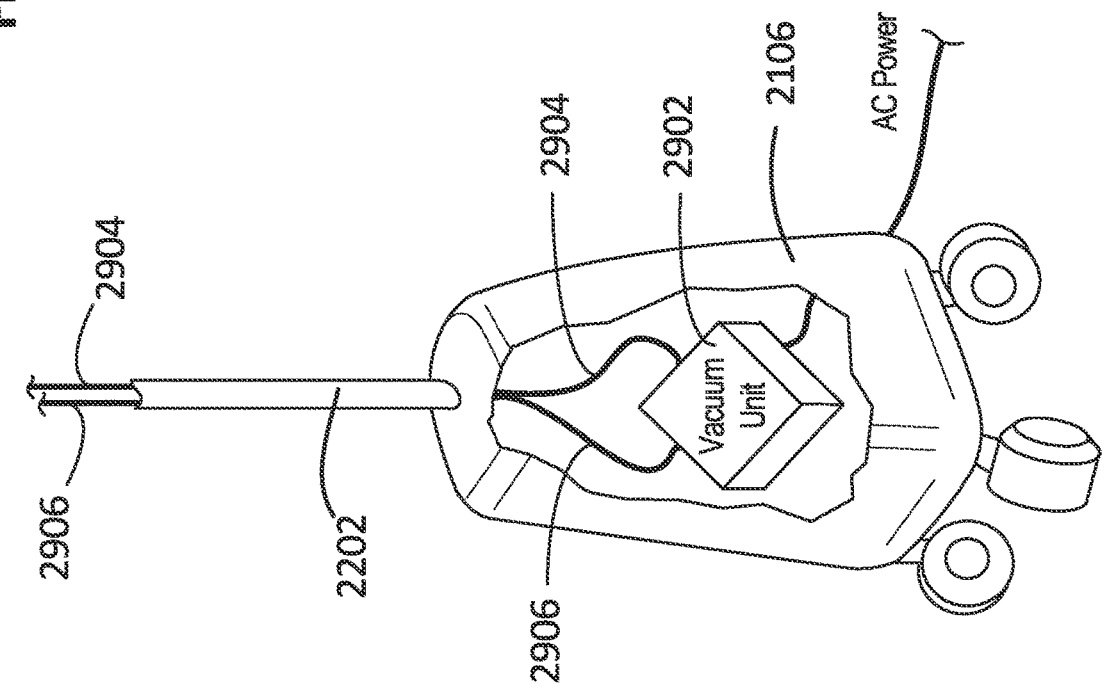
FIG. 29 depict an exemplary cross sectional view of a see through embodiment of a base unit with a vacuum unit that is controlled by a computerized microprocessor and powered by using AC power directly or through DC power from an internal battery that was previously charged or actively charged by AC powers source.

FIGS. 28 and 29 depict the pump housing 2106. The pump housing 2106 includes a mechanism to create suction such as, but not limited to, a vacuum unit 2902 including a piston pump, rotary vacuum pump, stepper motor with piston, and or other diaphragm type vacuum generation element such as a piezoelectric oscillator. The vacuum unit 2902 is connected to the control unit 2104 by one or more tubes 2904 and wires 2906 that are used to control the vacuum unit 2902.

This pump housing 2106 may or may not also contain a weight, a drive unit for a wheeled or motorized structure, and or other features to enable the system to easily move with or without user involvement. The pump housing 2106 may also necessitate a battery and or a power connection capability or wireless charging capability such that the unit itself could be powered or charged.

Figure 30:
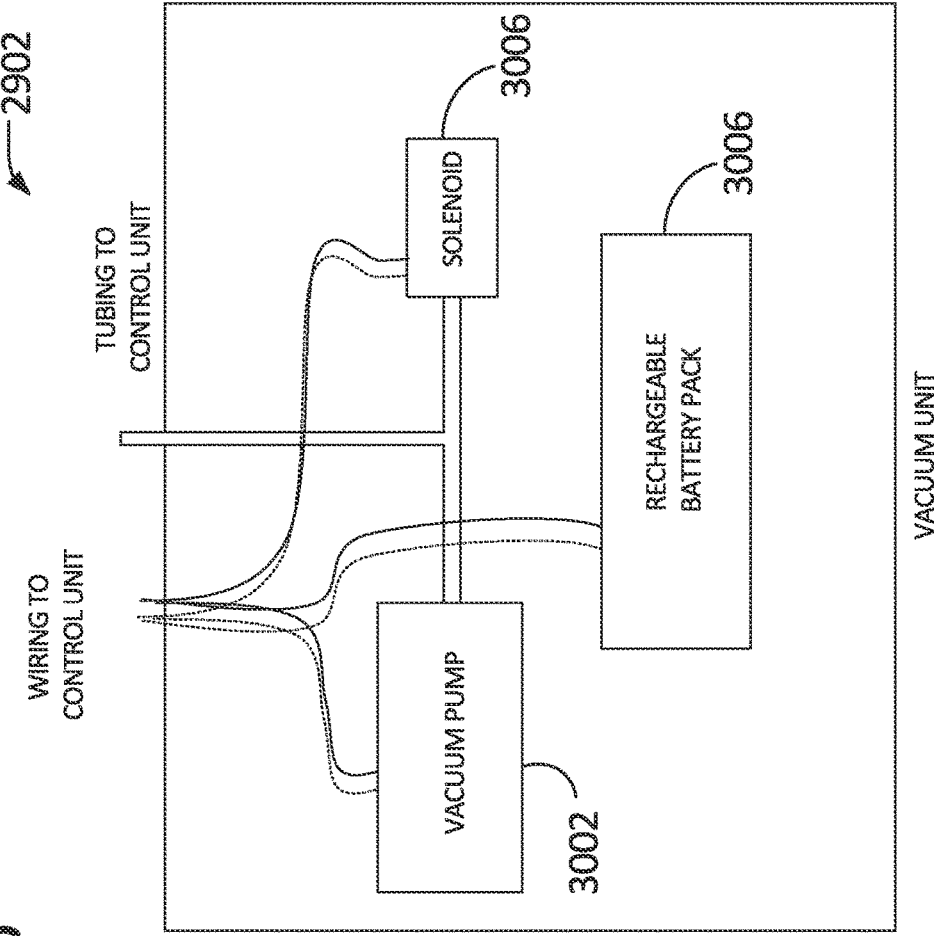
FIG. 30 depicts an exemplary internal mechanism of a breast pump for one or multiple users that contains wired linkages to a control unit in a different location than the main pumping unit as well as for long tubing to an outlet with breast flanges and cones for capturing breastmilk and a vacuum pump, battery, and solenoid to be used in concert with direction from the user via the control unit to operate the source of suction.

FIG. 30 comprises an internal view of the vacuum unit 2902 that comprises at least a vacuum pump 3002, a solenoid 3004, and a source of power such as but not limited to a battery pack 3006. The pump does not need a battery pack 3006 but one may be preferred to a power connection to the wall alone. In addition, the vacuum unit 2902 must have a connection tube that would be able to transmit the source of suction to the mom at the bedside and it could wirelessly communicate with the control unit through Bluetooth, Wi-Fi, RF, or other mechanism or alternatively it could communicate through wired communication. It may also contain a tracking unit such as a tile, RF chip, GPS tracker, Bluetooth chip, or other location system which would be used to help find the pump in the event that it was in one room or location or another.

FIG. 31 comprises an exemplary embodiment of a breast pump 3100 such that a breast pump control unit 3104 is connected to a source of suction 3102 by a flexible vacuum tube 3106 alone and the control unit 3104 stores the power internally. In addition, this control unit 3104 could be unpowered, instead using the wall suction 3102 to drive a spring actuated physical mechanism that would oscillate and release the vacuum pressure as a maximum vacuum limit of the pump 3100, which could be set by the user, was reached.

Figure 32:
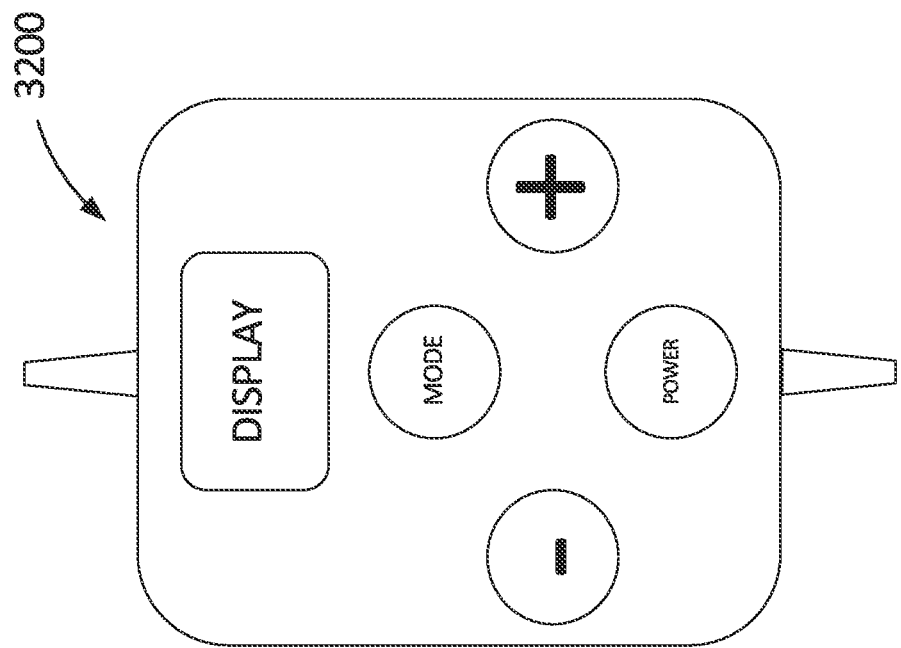
FIG. 32 depicts an exemplary control unit for a system where a source of suction and vacuum pump is detachably separate from the control unit.

FIG. 32 demonstrates an interface unit 3200 for use by a user to control the suction pressure waves and see various signals provided back to the user as feedback during the operation or setting of the control unit system. In this example (as with the interface unit 2700 described above), the unit 3200 has a plus button (to increase pressure), a minus button (to decrease pressure), a mode button (to select a desired pumping mode), and a power button along with a display.

Figure 33:
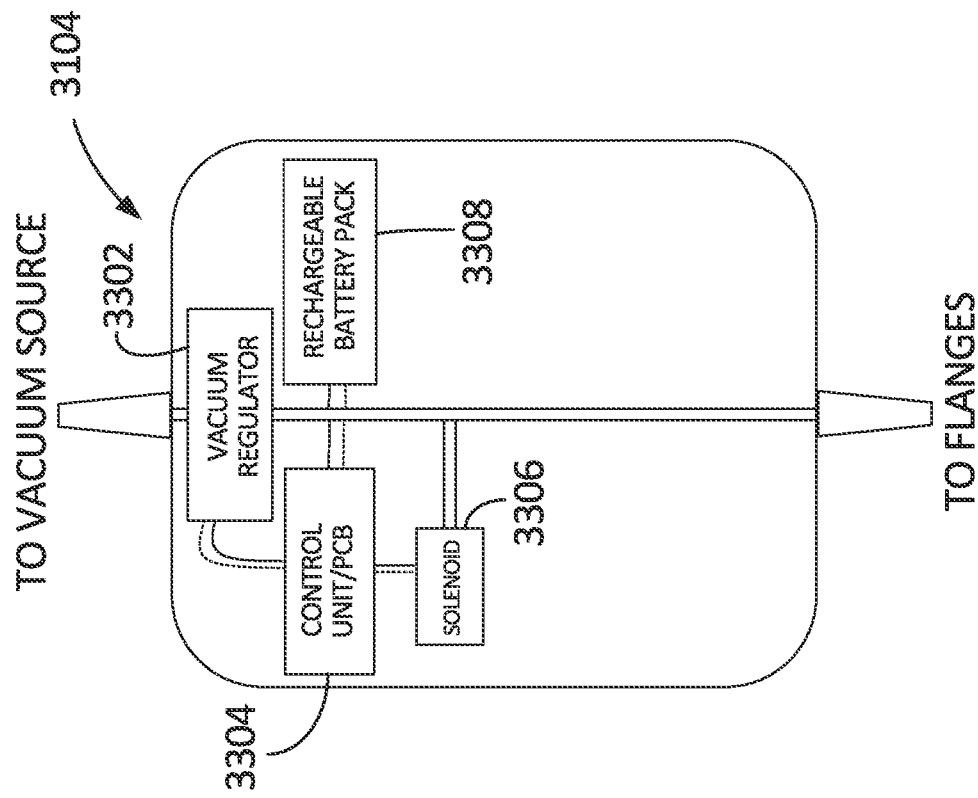
FIG. 33 depicts an exemplary internal mechanism for a breast pump device which may or may not have an additional vacuum motor inside but instead would depend at least partially on an outside source of suction such as that from a hospital vacuum system in the wall and that suction would be mediated by a vacuum regulator, control unit, and or solenoid which may be powered by the vacuum differential itself if mechanical or by the power supplied by a rechargeable battery or other AC or DC power source provided to the system.

FIG. 33 demonstrates the internal components of the control unit 3104 such that a vacuum regulator 3302, control unit and or circuit board 3304, and/or solenoid 3306 and/or battery pack 3308 are contained inside the control unit 3104 if a powered control unit. In the case of a non-powered control unit, a mechanical vacuum regulator and a spring driven pressure relief valve or multiple pressure relief valves could be used to create a suction waveform model based on central hospital suction from the wall. The suction would be piped from an inlet section in either case through a suction waveform oscillation system internal to the control unit and then that suction wave would be piped out to the flanges where the breast is accepted to allow for the vacuum wave to suck milk out of the breast.

Figure 34:
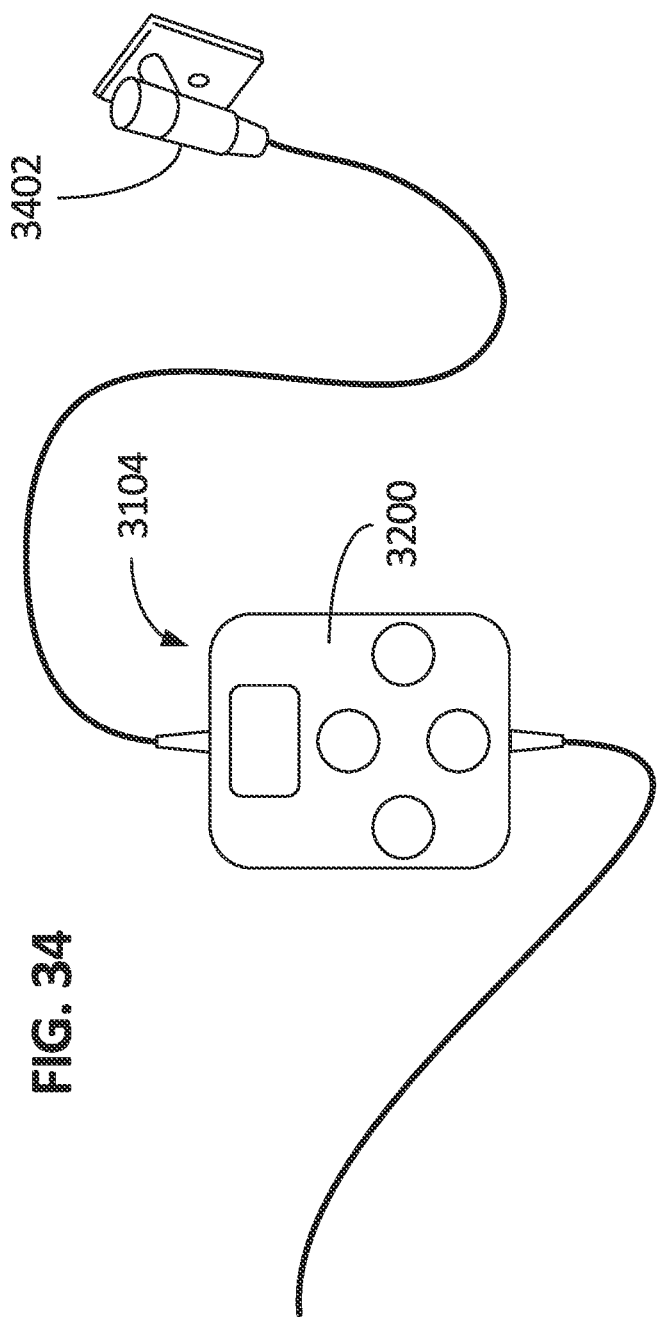
FIG. 34 depicts an exemplary side view of a mechanism for a breast pump control unit that is detachably removable from a main source of suction that may or may not be optionally mediated by a vacuum wall regulator.
Figure 35:
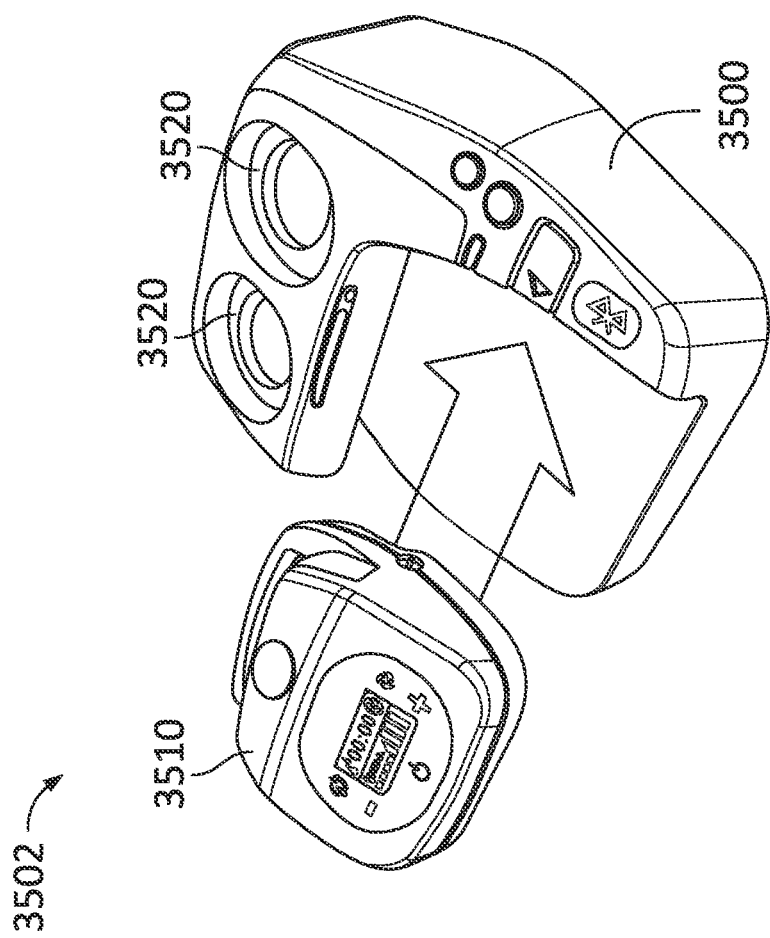
FIG. 35 depicts an exemplary view of a pumping unit also containing a control unit that may be removably taken from a docking station that can facilitate charging, data transfer, and or vacuum suction recharging if the removable component contained a vacuum suction reservoir.

FIG. 34 demonstrates an exemplary outer view of how the control unit 3104 could be connected to the wall including an optional vacuum regulator 3402 at the wall, which has a source of suction. In addition, the control unit 3104 could modulate the waveform and suction level shown at the wall and or prompt the user if the vacuum regulator at the wall needs to be adjusted in order for the pump to work properly. In this case, the control unit 3104 can move away from a primary source of vacuum that it is physically connected to through tubing.

Figure 36:
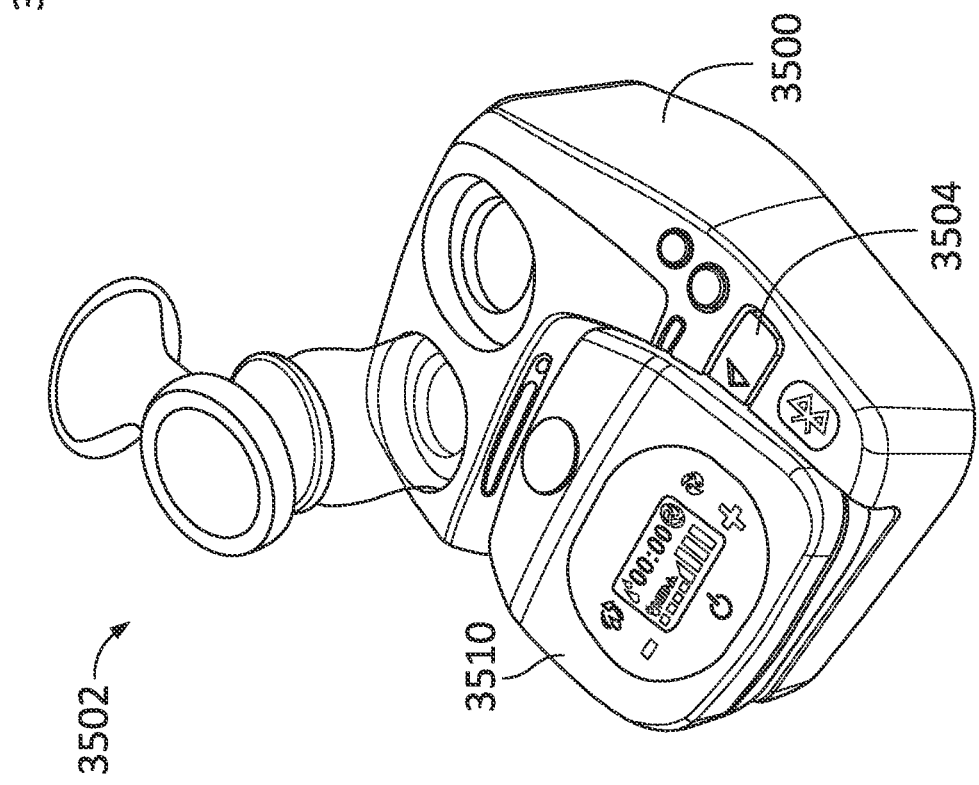
FIG. 36 depicts an exemplary view of the control unit being removed from the pumping unit of FIG. 35.
Figure 37:
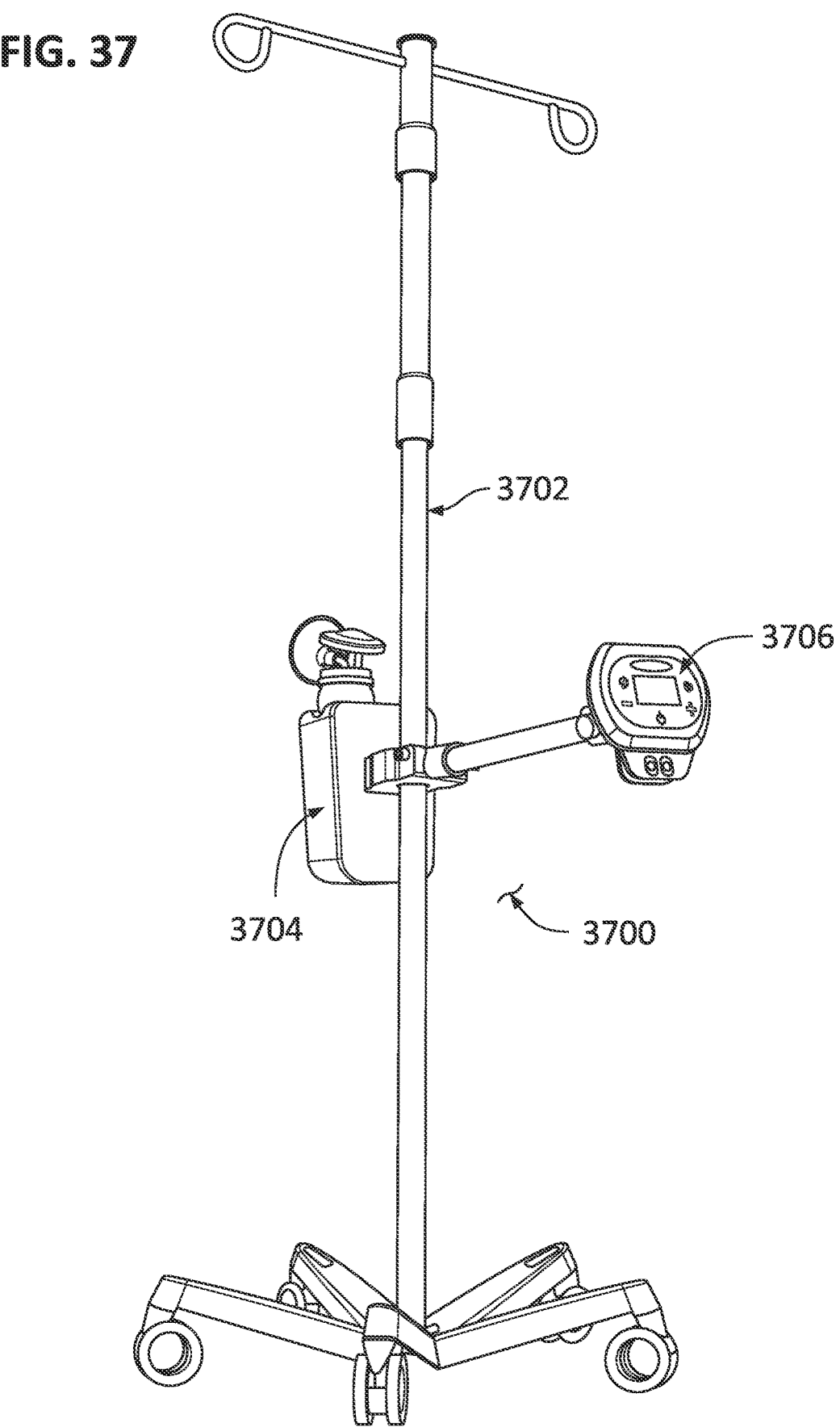
FIG. 37 depicts an exemplary view of another pump system being mounted to a trolley.
Figure 38:
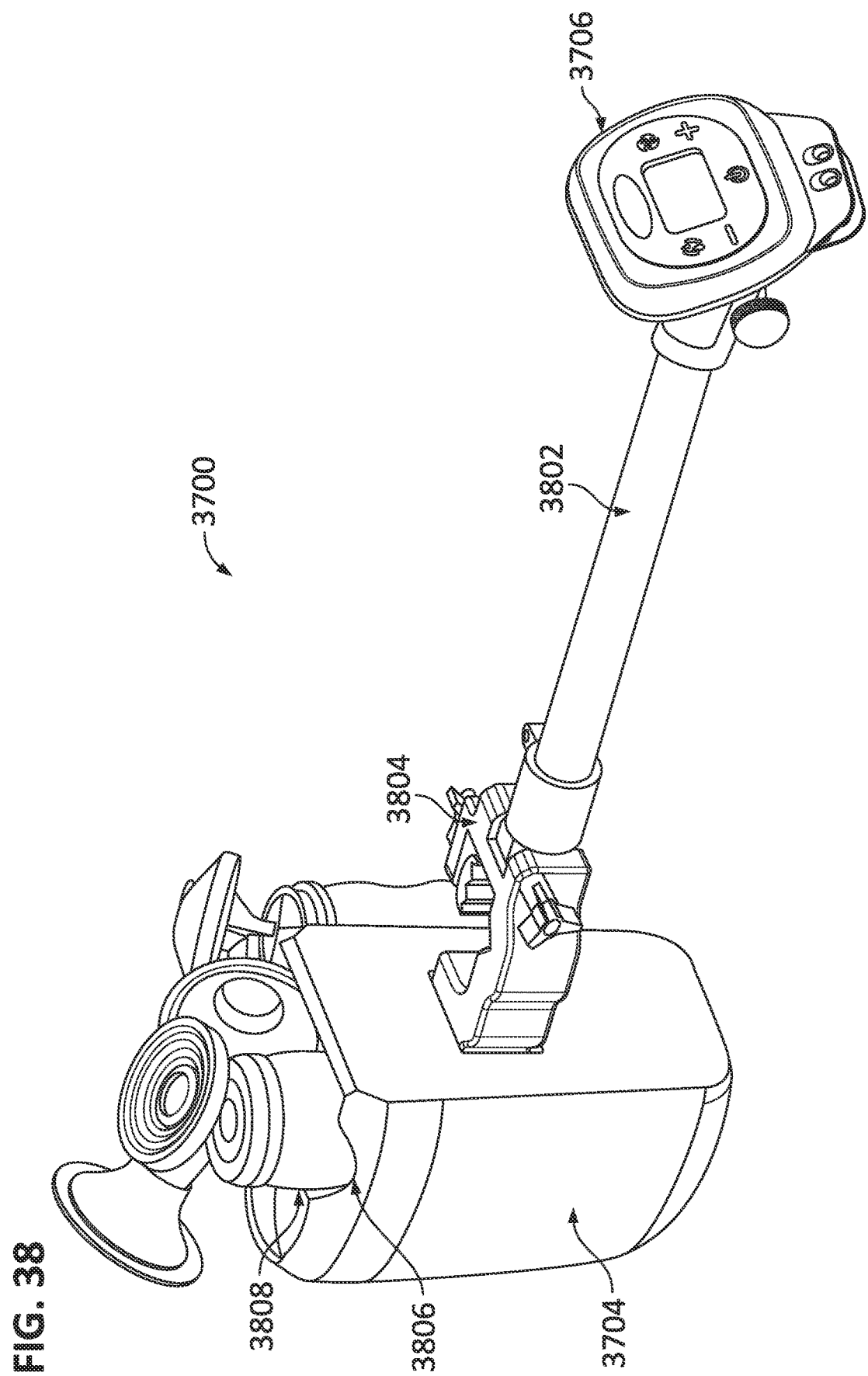
FIG. 38 depicts an exemplary view of the pump system of FIG. 37 in isolation.
Figure 39B:
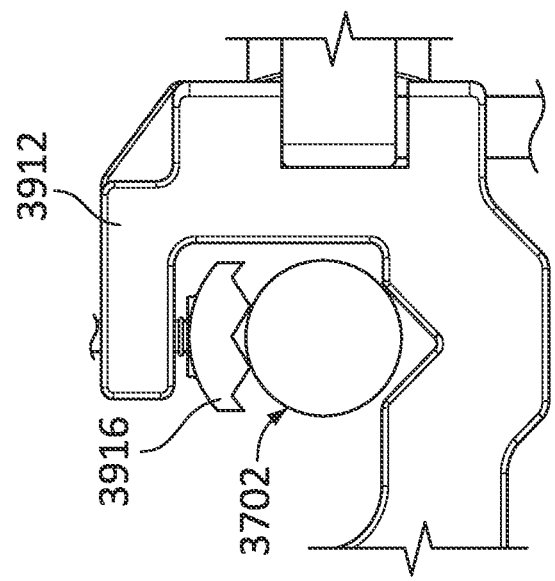
FIGS. 39A and 39B depict exemplary views of an attachment mechanism of the pump system of FIG. 38.
Figure 39A:
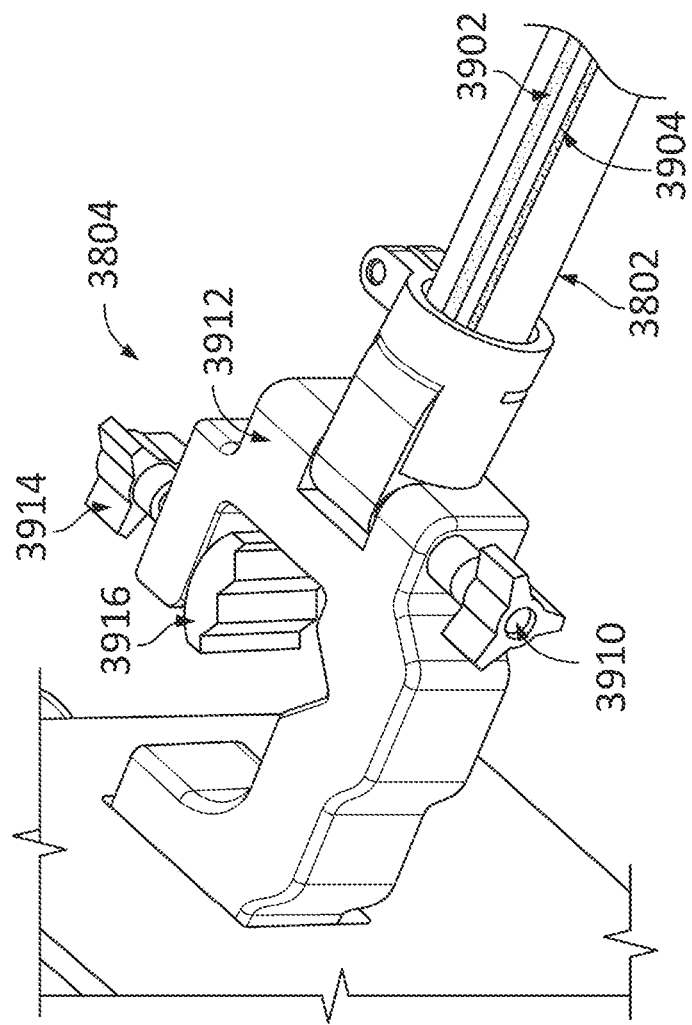
Figure 40B:
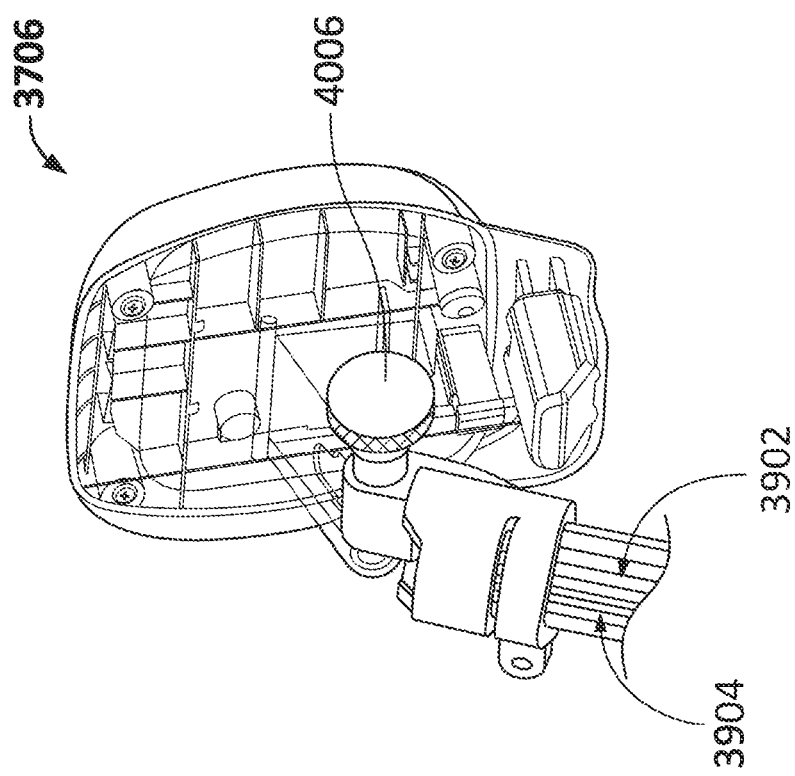
FIGS. 40A and 40B depict exemplary views of a control unit of the pump system of FIG. 38.
Figure 40A:
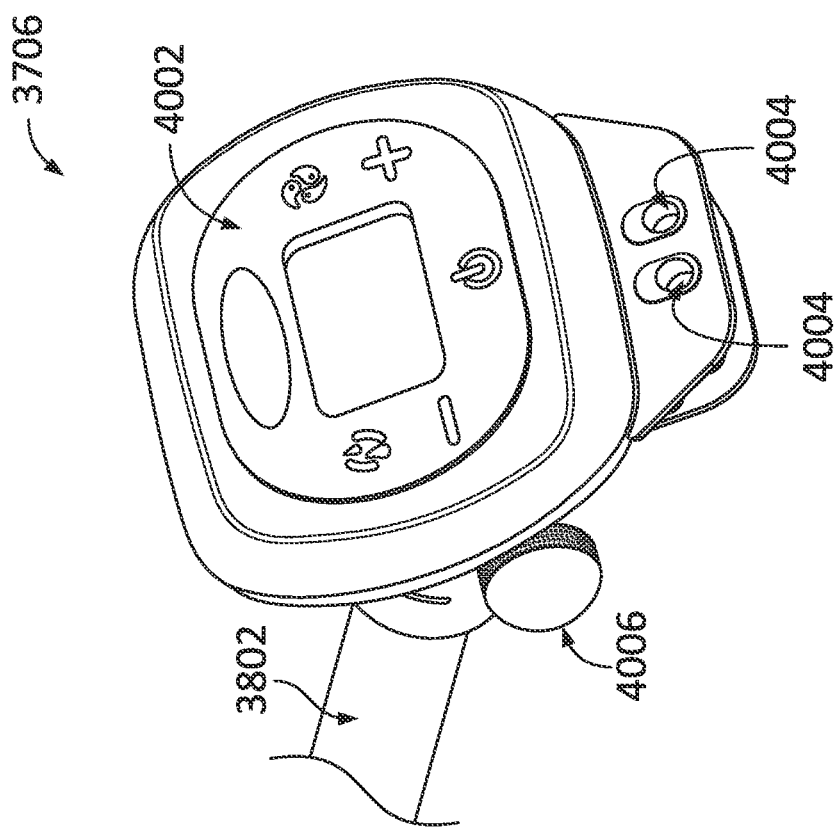

FIGS. 35A and 36 demonstrate a docking station 3500 where a breast pump unit 3502 can be separated into two components. One component comprises a pumping mechanism 3510 that could be taken with the user to a different location to pump, and a second component could comprise a unit that is likely to remain stationary, likely plugged into a source of power or data transfer, such as the docking station 3500. The pumping mechanism 3510 could be returned to the docking station 3500 for data transfer and or recharging. The docking station 3500 may also have bottle holders 3520 and additional buttons on it but it not necessarily need them. In this case, the removable component comprises a control unit and vacuum pump in one unit 3510 that moves together away from a secondary component of the breast pump system.

FIG. 36 demonstrates that the breast pump unit 3510 can be detached from the docking stations 3500 by pressing an ejection button 3504 moved away from a docking station 3500 that may also be used for data transfer and or other features such as but not limited to a night light and or bottle warmers, coolers, or holders. The system is detachable from itself such that the control unit and vacuum unit are comprised as one but can be moved away from other key elements of the embodiment.

FIGS. 37-44 depict an exemplary pole mount pump system 3700 where a pump housing 3704 is mounted to a standard hospital IV pole 3702. In this instance, a control head 3706 is separated from the pump housing 3704. The control head 3706 is placed at the end of a conduit 3802 extending between the control head 3706 and the pump housing 3704.

As described further herein, the pump housing 3704 can hold a single pump motor or optionally multiple pump motors and function as provided above The conduit includes a vacuum line 3902 and electrical lines 3904 extending between the control head 3706 and the pump housing 3704. In example embodiments, the conduit 3802 separating the control head 3706 and the pump housing 3704 is at least one foot, 1.5 feet, or two feet. Other distances can be used. For example, longer extensions can be provided with corresponding counterweights to allow for stability. In the horizontal position, the control head 3706 is located very close to the user.

An exemplary IV pole clamp system 3804 includes a V-Block clamp bracket 3912 and a control head angle adjustment 3910. The control head angle adjustment 3910 can be loosened and tightened to allow the control head 3706 to be pivoted between horizontal (FIG. 43) and vertical (FIG. 44 positions).

The clamp bracket 3912 includes a sliding v-block 3916 that is controlled by a pole clamp adjustment mechanism 3914 to capture the IV pole 3702 therein. Specifically, the clamp bracket 3912 can be screwed clockwise to capture the clamp bracket 3912 on the IV pole 3702 at the desired height.

The example control head 3706 includes a touch pad 4002 to allow the user to manipulate the pump system 3700, such as turn on and off the pump and increase/decrease the pumping pressure. Vacuum ports 4004 allow provided to allow the user to connect vacuum tubes thereto.

An angle of the control head 3706 can be adjusted using an angle adjustment screw 4006. When loosened, the control head 3706 can be pivoted about the screw 4006. When tightened, the screw 4006 fixes the angular orientation of the control head 3706.

Figure 42:
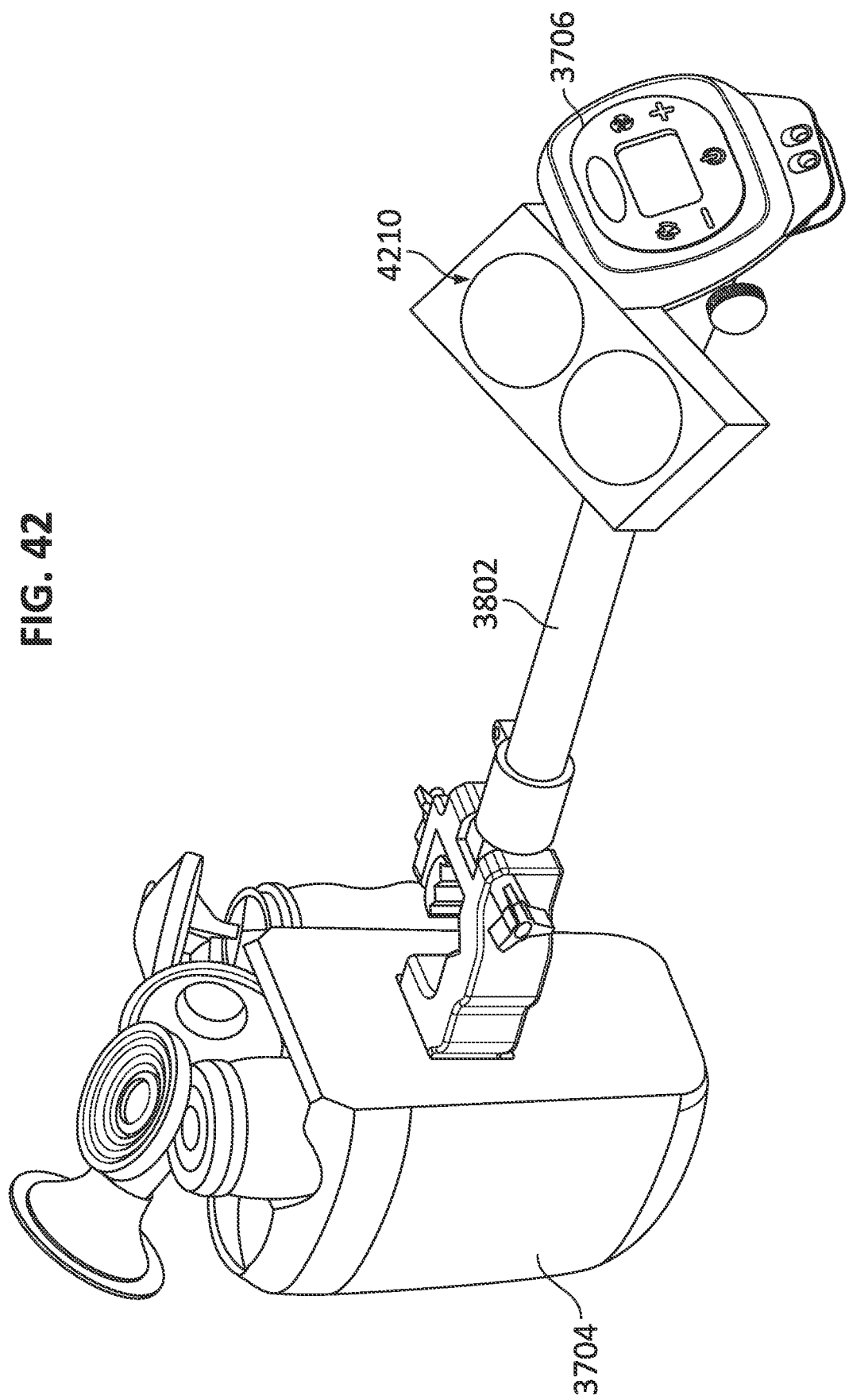
FIG. 42 depicts another exemplary view of the pump system of FIG. 38 including an alternative bottle holder.

The exemplary pump housing 3704 includes two types of bottle holders. One bottle holder version captures the bottles in a recessed area 3808. The other bottle holder version utilizes recesses in the housing wall holding the flanges 3806 in place while the bottle hangs off the side of the housing. FIG. 42 depicts an exemplary alternate bottle holder 4210.

In the depicted example, the pump housing 3704 houses multiple motors positioned in a multiple motor/silencer box assembly 4102. The silencer box 4102 is designed to significantly reduce pump noise. The motors can be the same ones used in personal, single user pumps. The use of multiple, smaller motors helps avoid the use of much larger, heavier stepper motors. The power consumption is lower, and the resulting rechargeable battery is smaller.

Figure 43:
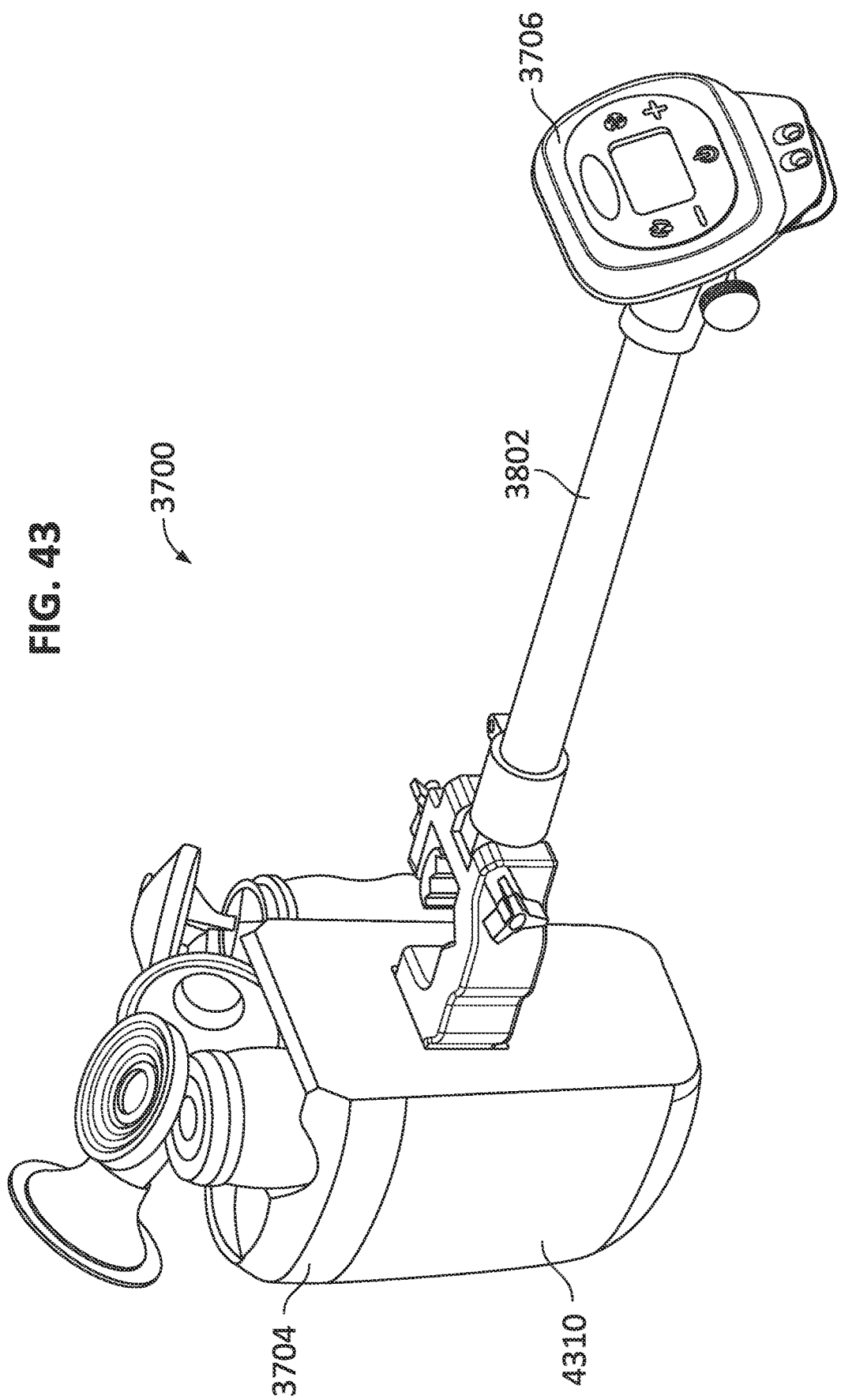
FIG. 43 depicts an exemplary view of the pump system of FIG. 38 in a horizontal orientation.
Figure 44:
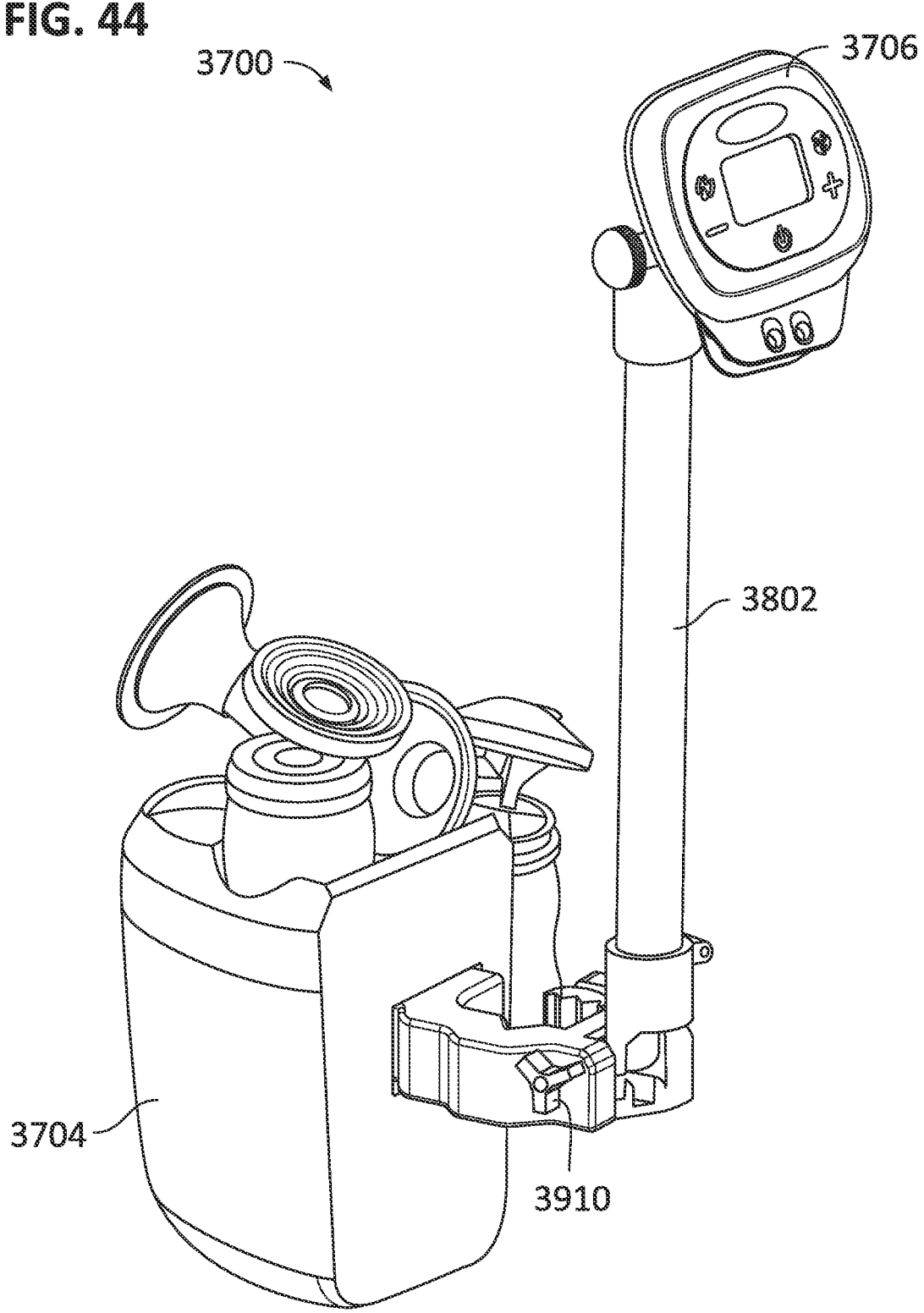
FIG. 44 depicts an exemplary view of the pump system of FIG. 38 in a vertical orientation.

FIG. 43 depicts an exemplary variation of the system 3700. Specifically, the pump motors are located within the control head 3706. This eliminates running the vacuum line down the conduit 3802. A counterweight 4310 is used to help balance the additional weight placed at the control end of the conduit 3802.

A power cable can run down the conduit 3802 to power the control head 3706 and the motors, PCB, and solenoid apparatus located within the control head housing. Additionally, batteries could be enclosed within the control head 3706 in order to power the system and or the power cable could be plugged directly into the control head by the user without needing to run down or alongside the conduit 3802. Similarly, a power cable could run down the conduit 3802 from the control head and batteries or other portable power storage apparatus could be housed within the counterweight housing 4310, which could be plugged in by the user or powered through another conduit leading down the pole 3702 to a power outlet. Bottle holders or a recessed area for accessory storage 3808 could additionally be located on the control head 3706 if desired.

The control head 3706 and whatever apparatus essential to operate the system mechanism may be able to orient around a pivot point from the stand support 3702 such that the control head 3706 can cantilever towards the user. The cantilevered stand 3802 plus a breast pump apparatus could be configured such that the pump apparatus 4102 and controls 3706 could be housed together at the end of the cantilever 3802 or it could be apart split with components 4102 on the stand housing and control unit 3706 at the end of the cantilever 3802.

FIGS. 45A and 45B depict an exemplary alternate pole mount pump system 4500. Specifically, a retractable arm 4502 with the control head 3706 mounted thereon can be extended towards and away from the user. In addition, a mount 4504 at the end of the arm 4502 slides in a rail 4506 to allow a height of the control head 3706 to be further manipulated.

Figure 46:
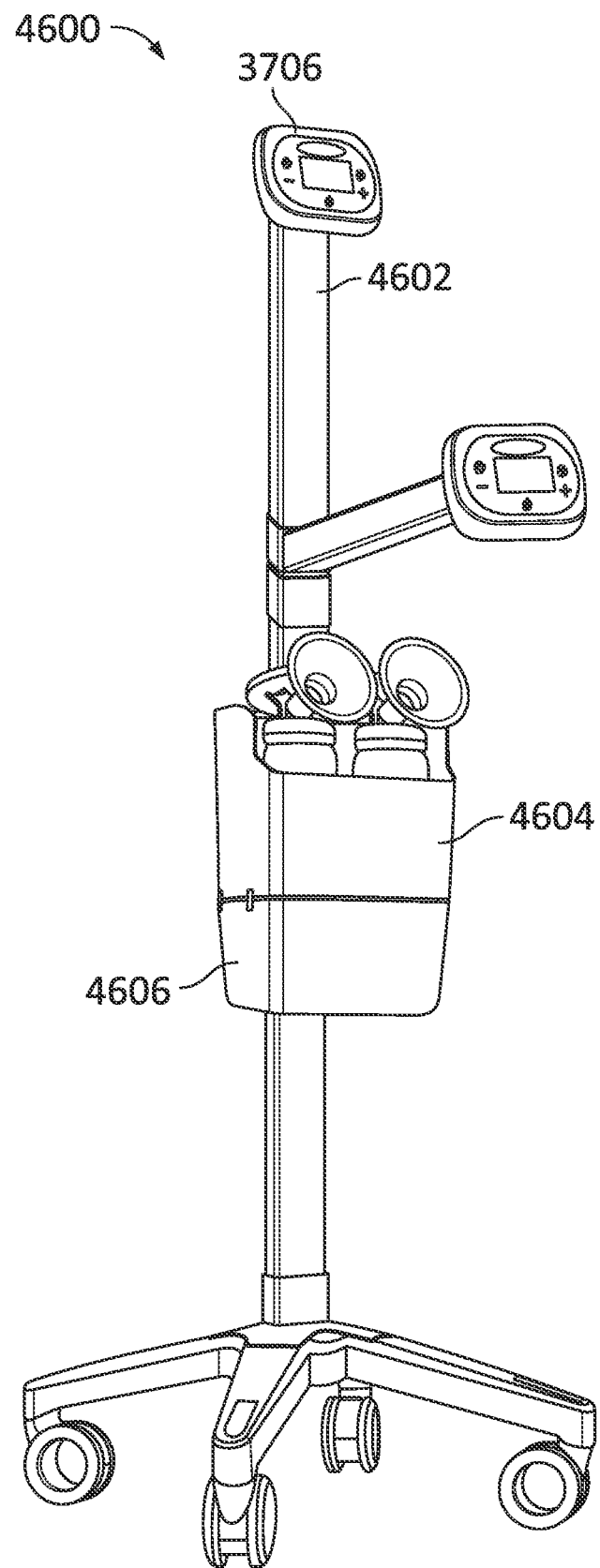
FIG. 46 depicts an exemplary view of an alternative pump system.
Figure 47:
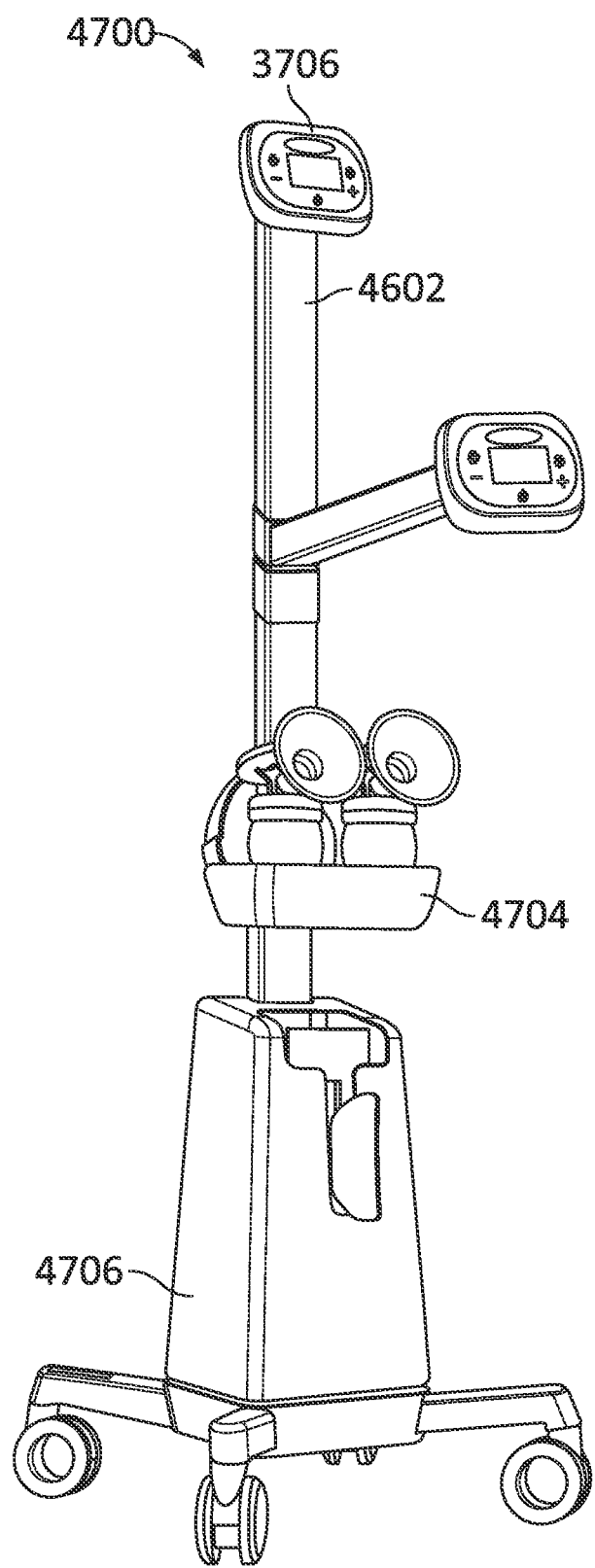
FIG. 47 depicts an exemplary view of an alternative pump system.

FIG. 46 depicts an exemplary alternate pole mount pump system 4600. The control head is incorporated into the pole or trolley 4602. In this instance, there is a storage/bottle holder 4604 located just above the pump motors 4606. FIG. 47 depicts an alternate pole mount pump system 4700 in which the pump motors are located at a base 4706 of the trolley 4602. The design also includes bottle holders 4704.

Figure 48:
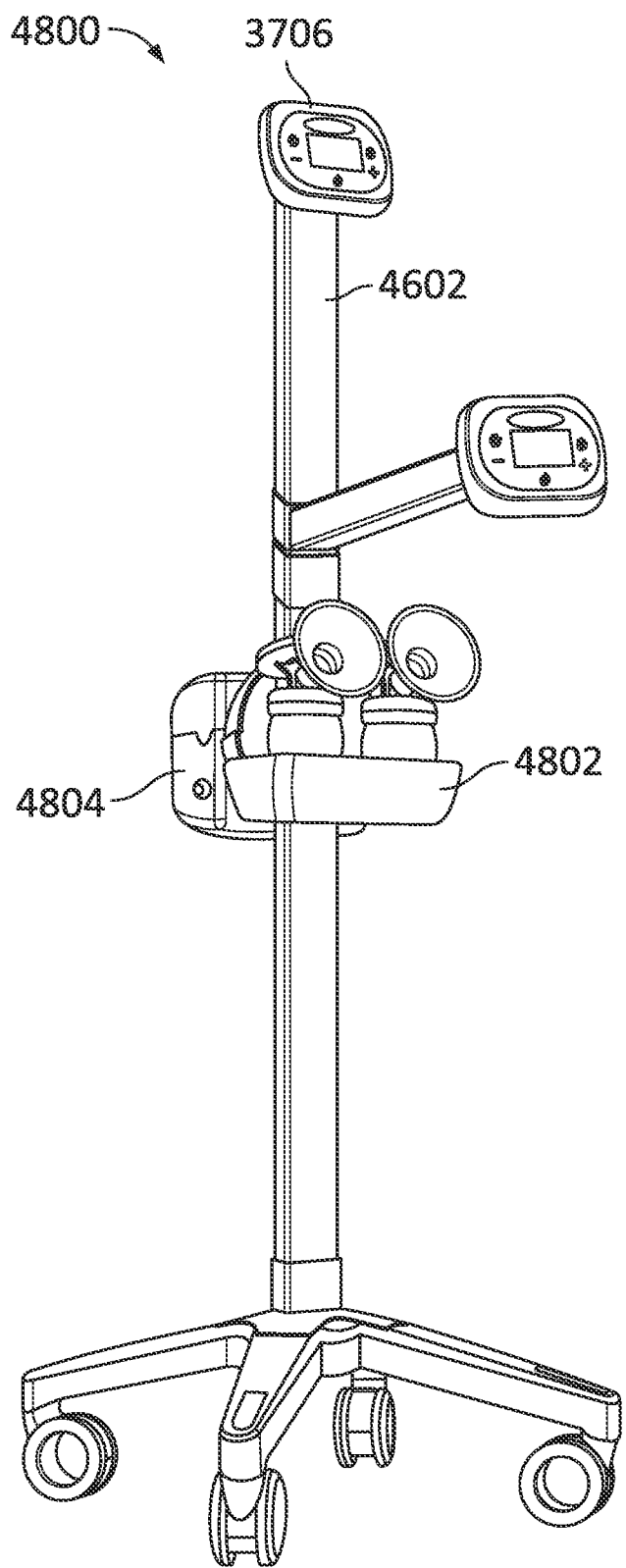
FIG. 48 depicts an exemplary view of an alternative pump system.

FIG. 48 depicts an exemplary alternate pole mount pump system 4700 in which the pump motors 4804 are located opposite the bottle holders 4802

Figure 49:
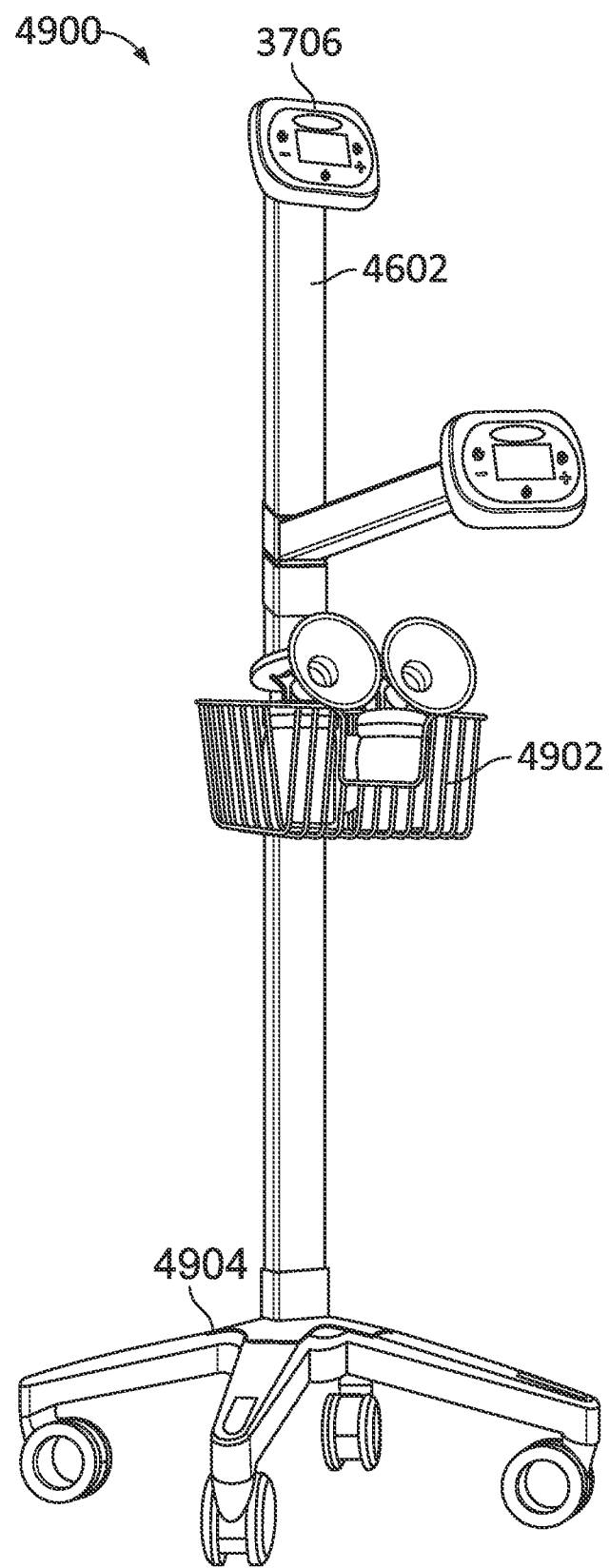
FIG. 49 depicts an exemplary view of an alternative pump system.
Figure 50:
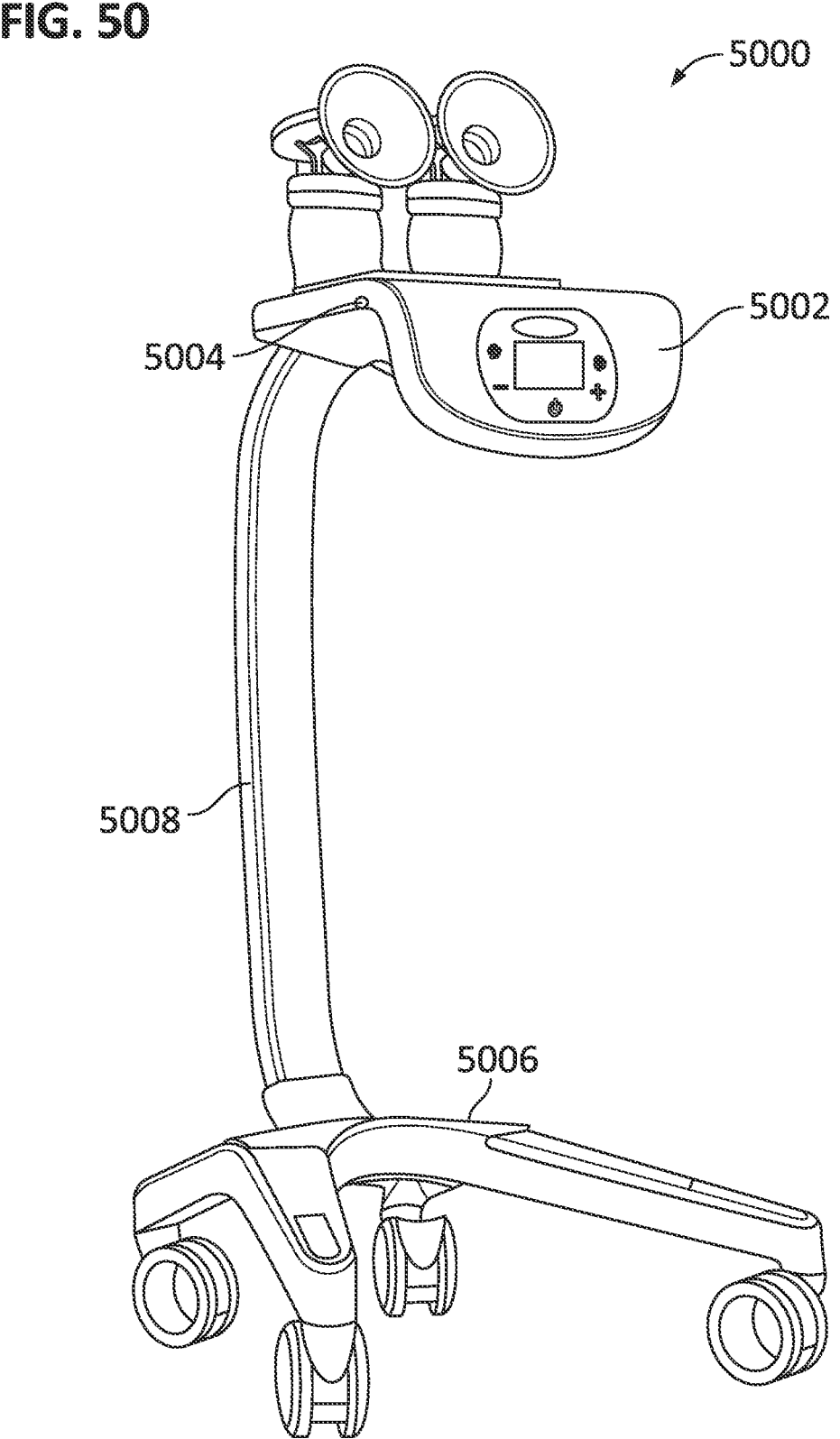
FIG. 50 depicts an exemplary view of an alternative pump system.
Figure 51A:
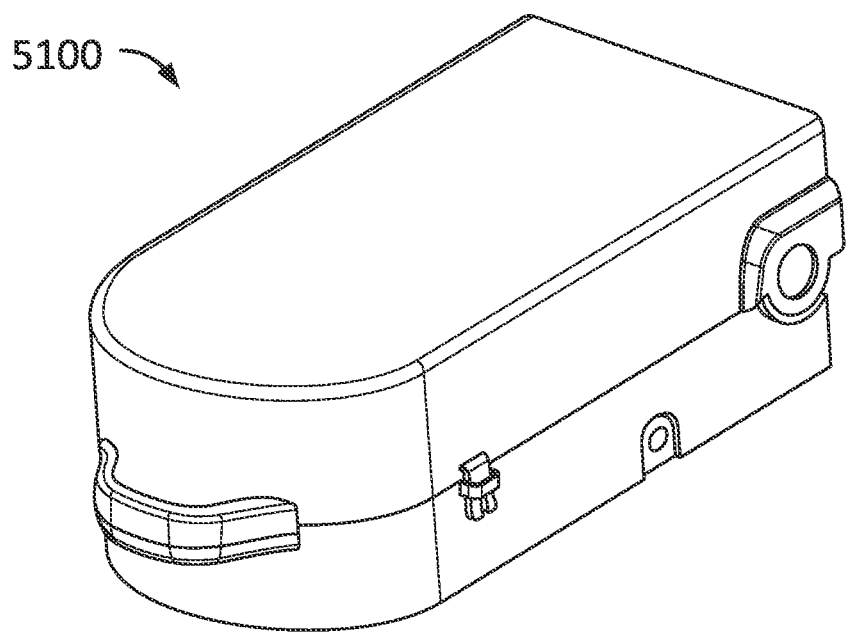
Figure 51B:
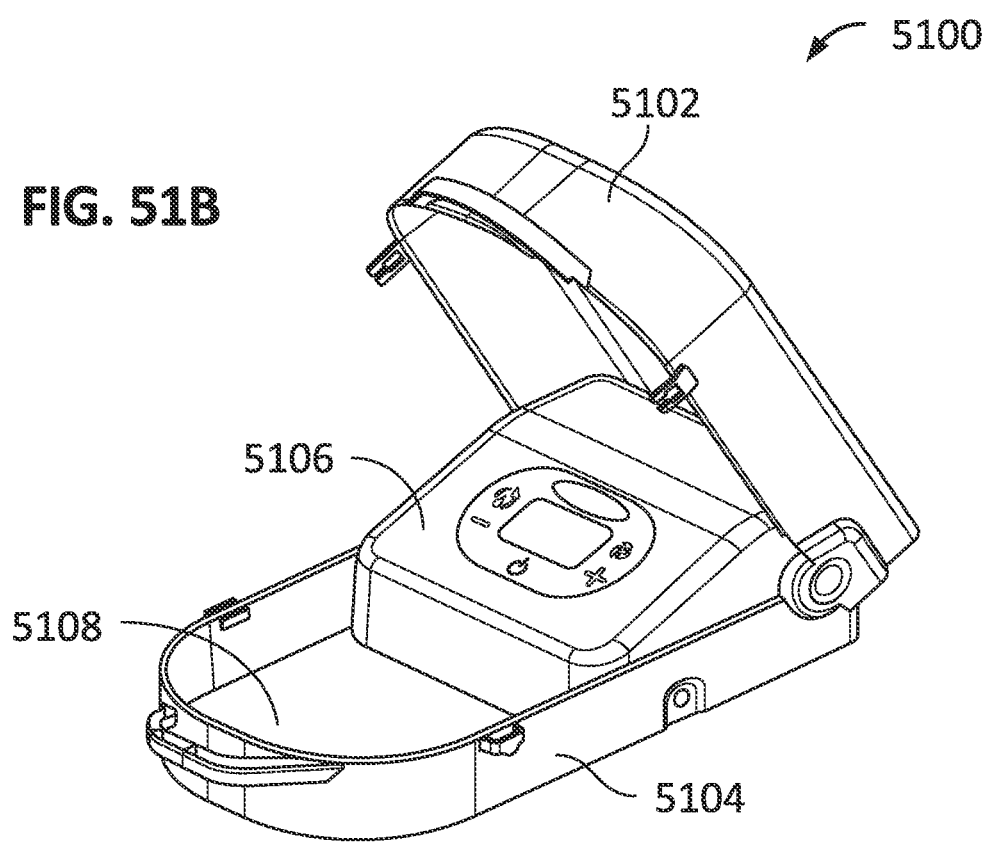
Figure 52D:
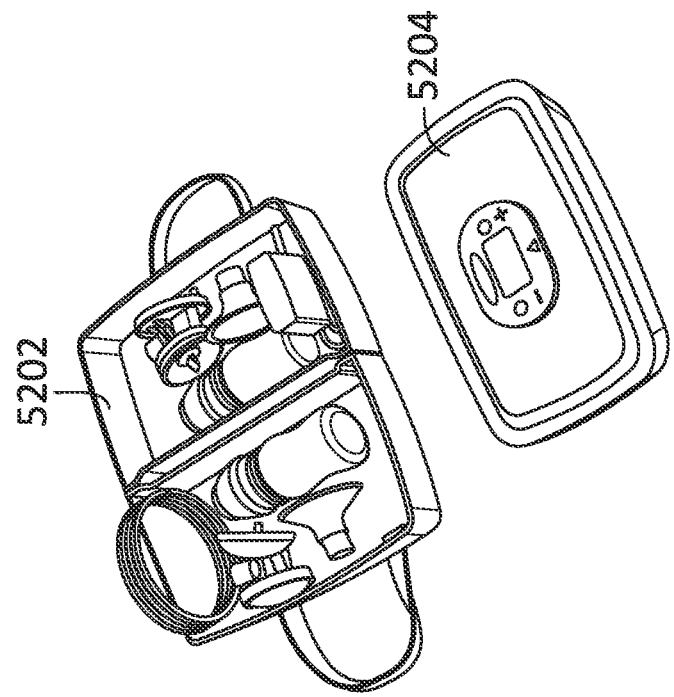
Figure 52C:
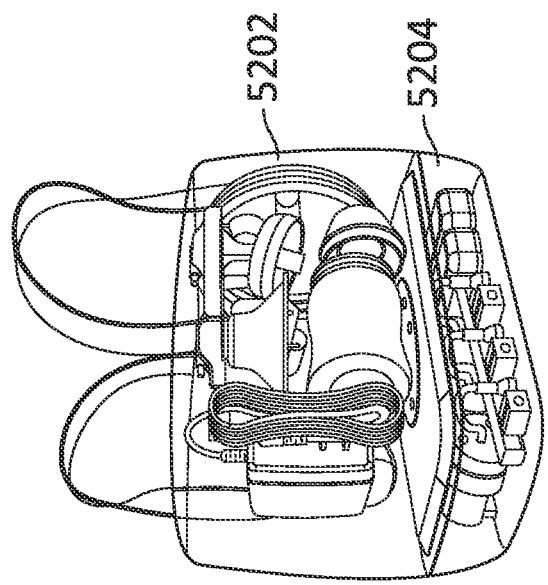
Figure 53D:
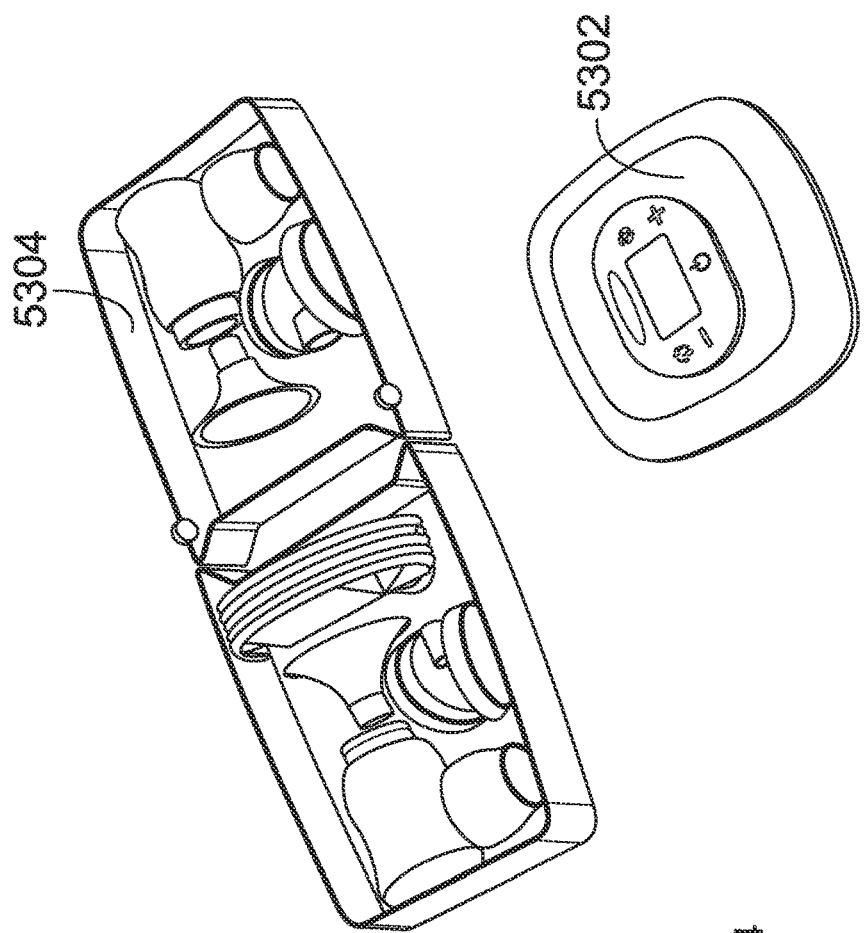
Figure 53C:
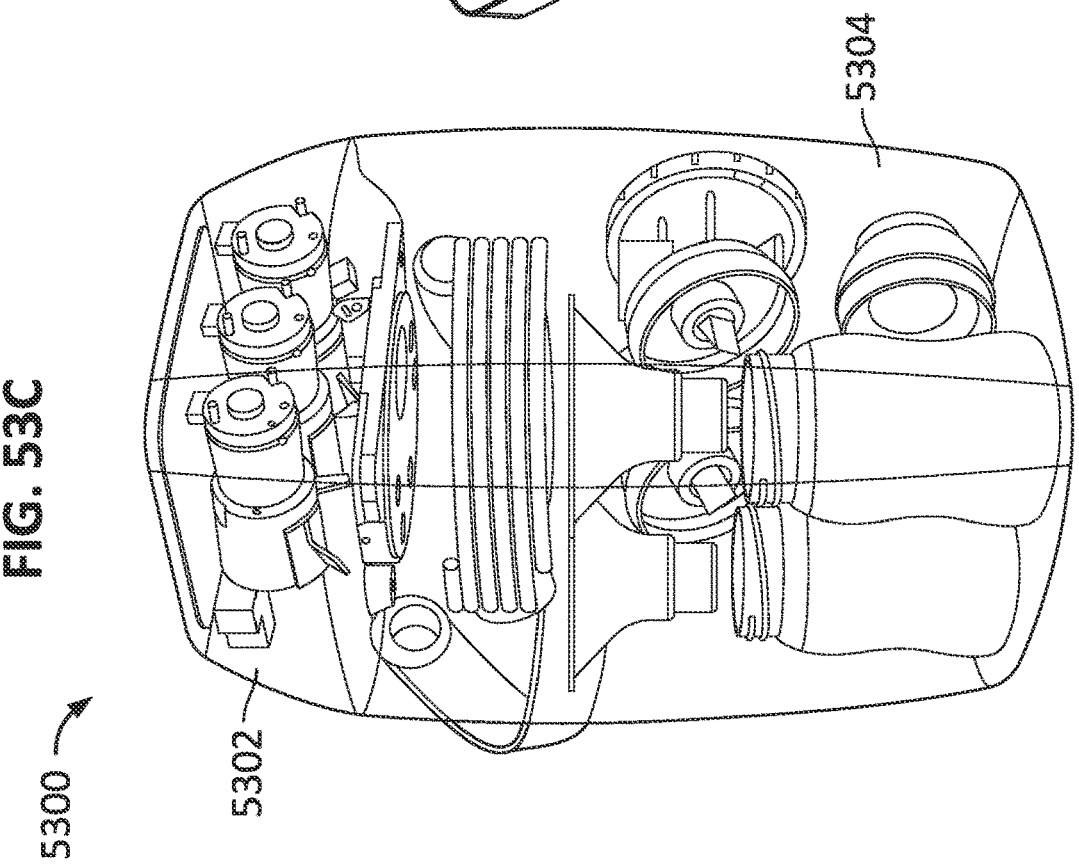
Figure 54A:
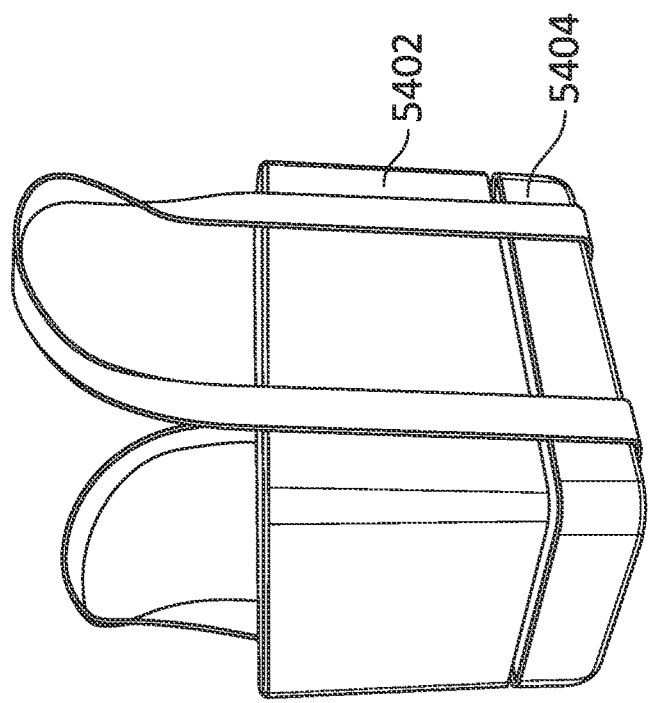
FIGS. 54A-54D depict an exemplary view of an alternative portable pump system.
Figure 54B:
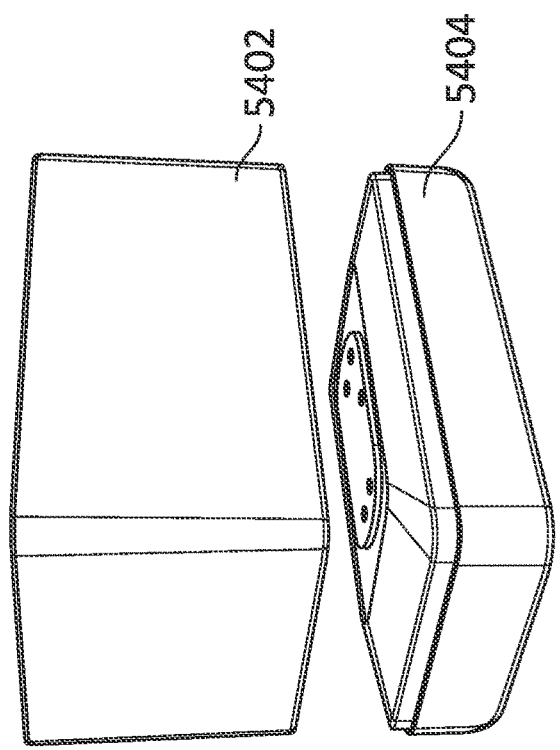
Figure 54D:
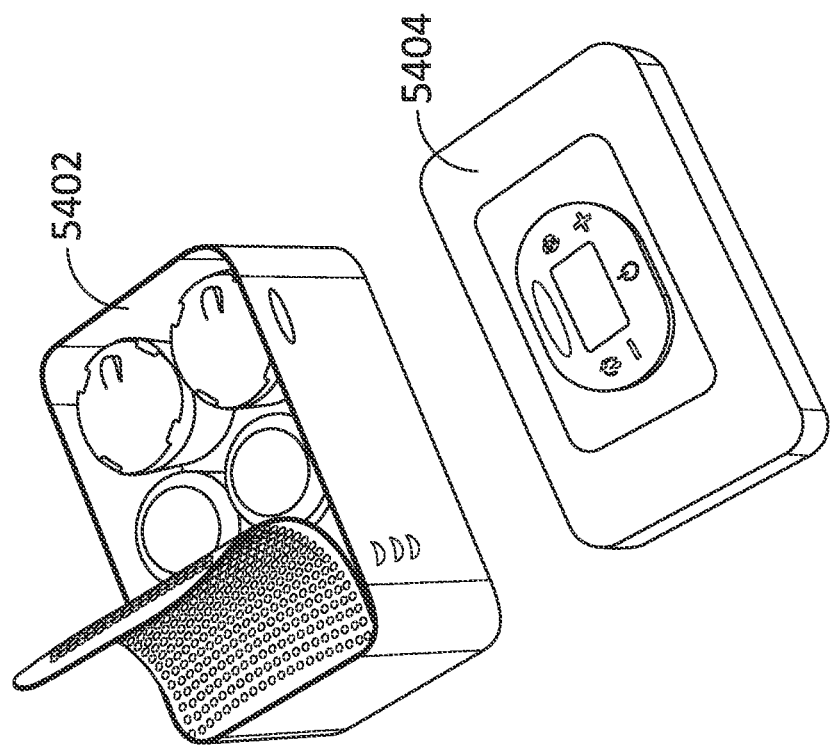
Figure 54C:
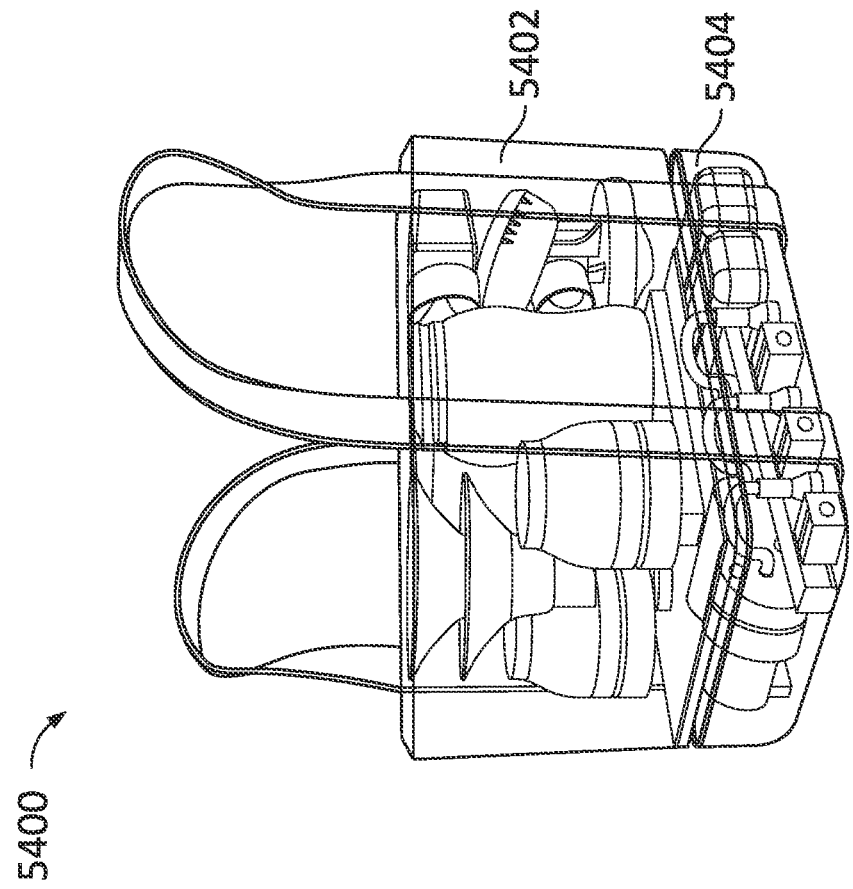
Figure 55D:
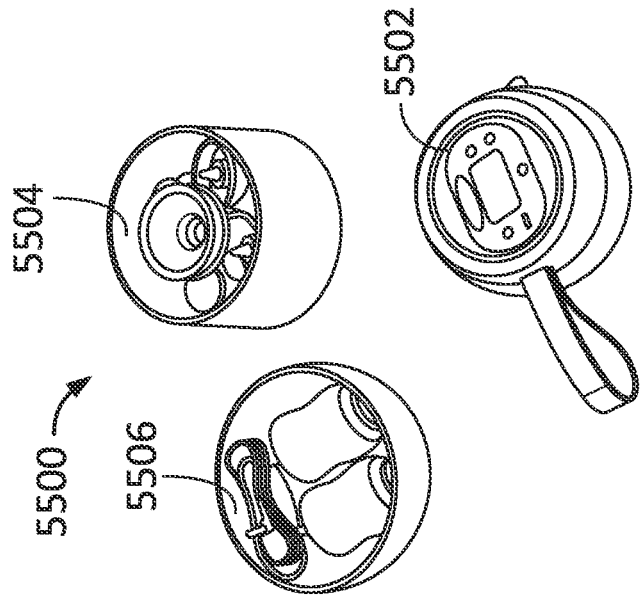
Figure 55C:
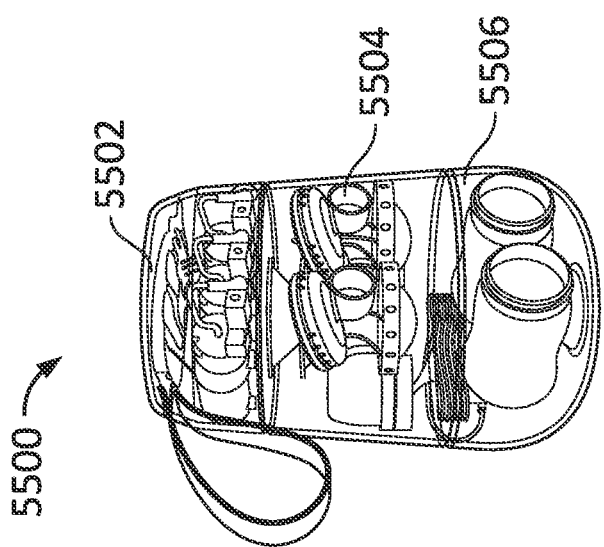
Figure 57A:
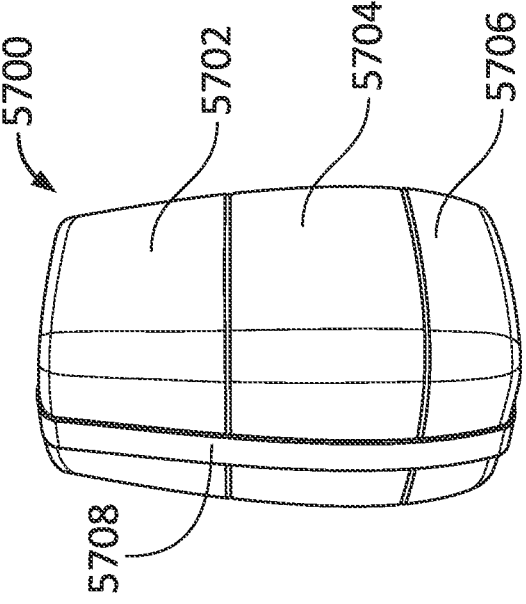
FIGS. 57A-57D depict an exemplary view of an alternative portable pump system.
Figure 57B:
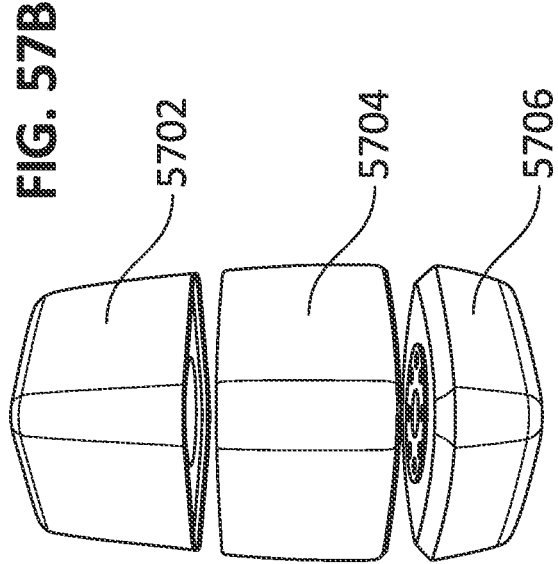
Figure 57C:
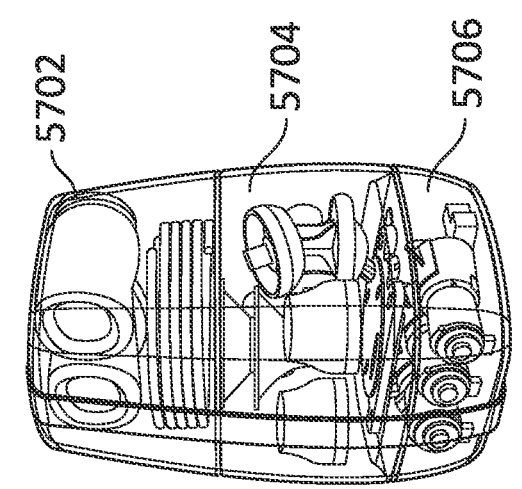
Figure 57D:
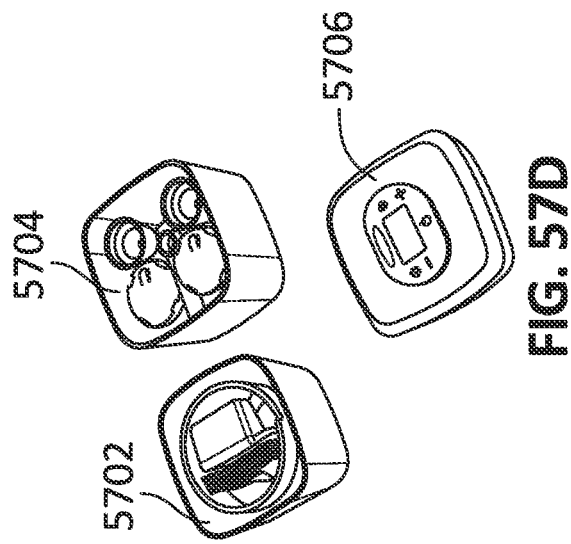
Figure 58B:
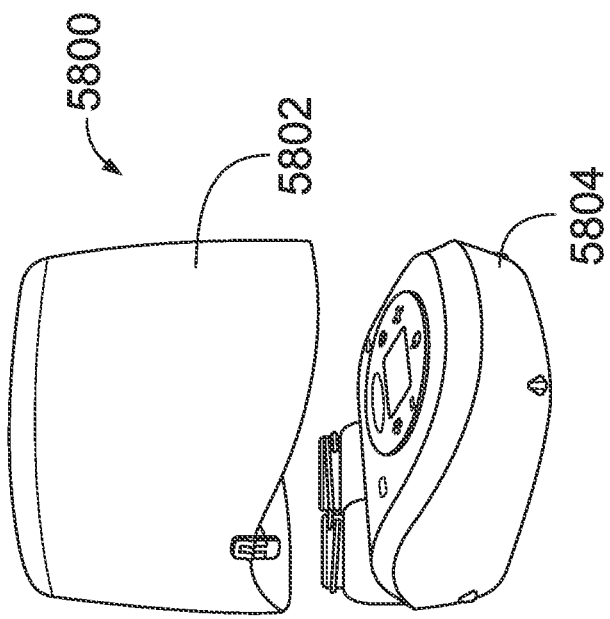
FIGS. 58A-58D depict an exemplary view of an alternative portable pump system.
Figure 58A:
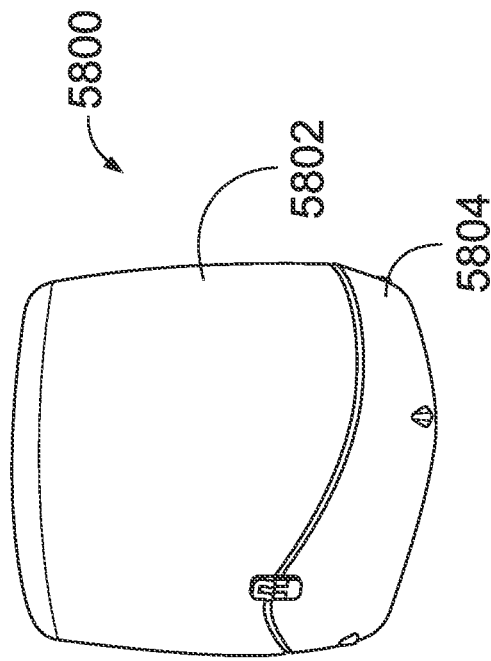
Figure 58D:
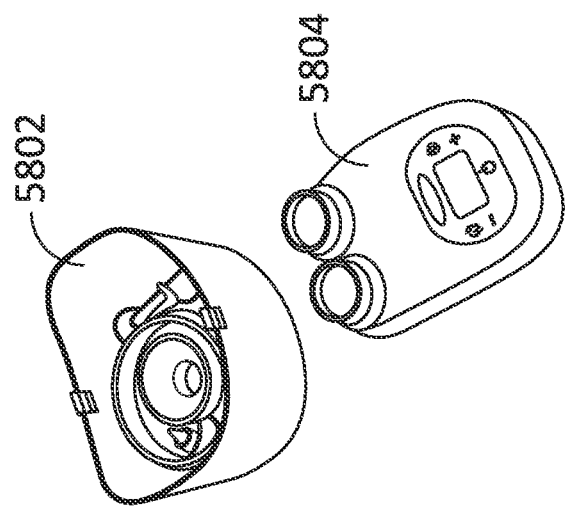
Figure 58C:
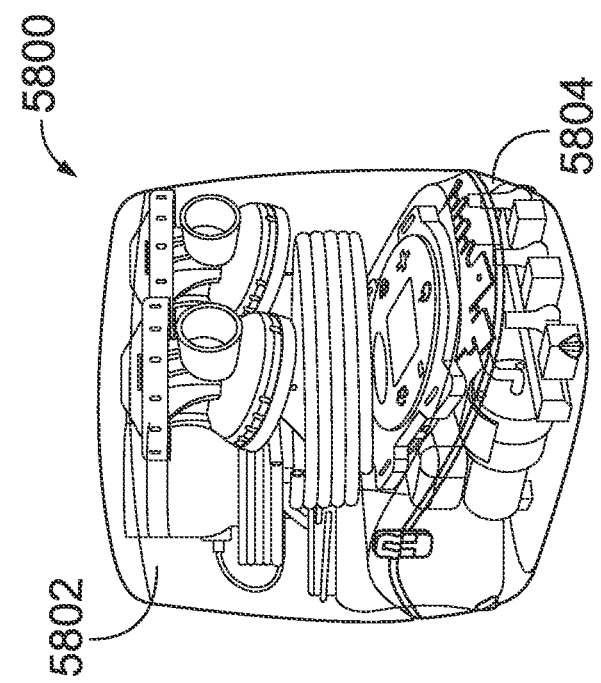
Figure 59D:
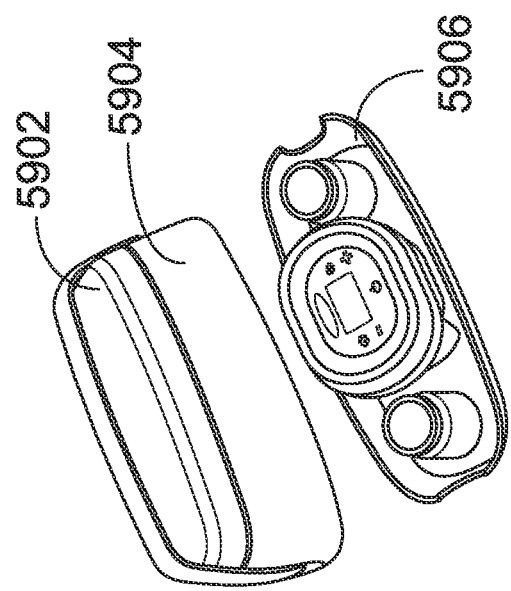
Figure 59C:
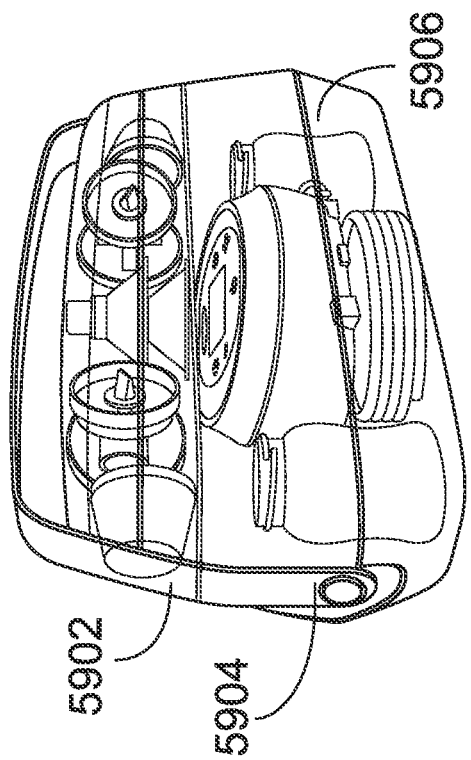

FIG. 49 depicts another exemplary alternate pole mount pump system 4900 in which the motor/silencer assemblies 4904 are located in the base of the trolley 4602. Finally, FIG. 50 depicts an exemplary alternate pole mount pump system 5000. Specifically, a specialized, C-shaped trolley 5008 is used. The motor/silencer assemblies 5006 are located are integrated into the base of the trolley 5008 or, alternatively, included as part of the upper portion 5004 forming the control head 5002.

In yet further alternative designs, the pump system can be a combination of two or more of the embodiments described herein. For example, the pump system can include a combination of flexible, bendable and/or telescoping components that allow the user to position the control unit as desired. For example, in one alternative embodiment, the pump system can include a telescoping portion that moves up and down to a desired height, and a bendable portion that extends laterally towards and away from the user. Other combinations are possible.

Referring now to FIGS. 51-60, alternative designs for breast pump systems integrated into carrying cases are provided. These allow the pump systems to be even more portable.

More specifically, these breast pump systems can include a control unit and vacuum unit with a plurality of pump motors. The systems can also include a carrying case to hold the control unit and vacuum unit, along with pumping accessories like bottles, vacuum tubes, and breast shields. The carrying case is configured to be carried and opened to reveal the control unit, vacuum unit, and pumping accessories.

FIGS. 51A-51F illustrate a pump system 5100. This pump system 5100 is integrated into a case with an upper portion 5102 and a lower portion 5104 that together house the various pump components. A control head 5106 and silencer box 5120 are integrated into the interior of the system 5100. Further, the lower portion 5104 includes an open area 5108 for carrying pumping accessories like bottles and vacuum tubes.

FIGS. 52A-52D illustrate another pump system 5200 including a case with handles 5210. The system 5200 includes a first portion 5202 that houses pumping accessories and a second portion 5204 that houses the control unit and vacuum unit. The second portion 5204 can include a silencer assembly with multiple motors positioned therein. The first portion 5202 snaps or is otherwise coupled to the second portion 5204. The pump system 5200 can generally be carried to a desired location. The first portion 5202 can then be separated from the second portion 5204 to access and use the pump.

FIGS. 53A-53D illustrate another pump system 5300 including a case with handles. The system 5300 includes a first portion 5302 that houses the control unit and vacuum unit, and a second portion 5304 that houses the pumping accessories. The first portion 5302 snaps or is otherwise coupled to the second portion 5304. The pump system 5300 can generally be carried to a desired location. The first portion 5302 can then be separated from the second portion 5304 to access and use the pump. Further, the second portion 5304 folds open to more easily reveal the pumping accessories contained therein.

FIGS. 54A-54D illustrate another pump system 5400 including a case with handles. The system 5400 includes a first portion 5402 that houses pumping accessories and a second portion 5404 that houses the control unit and vacuum unit. The second portion 5404 can include a silencer assembly with multiple motors positioned therein. The first portion 5402 snaps or is otherwise coupled to the second portion 5404. The pump system 5400 can generally be carried to a desired location. The first portion 5402 can then be separated from the second portion 5404 to access and use the pump.

FIGS. 55A-55D illustrate another pump system 5500 including a case with a handle. The system 5500 includes first and second portions 5502, 5504 that house pumping accessories and a third portion 5506 that houses the control unit and vacuum unit. The third portion 5506 can include a silencer assembly with multiple motors positioned therein. The portions snap or are otherwise coupled to one another in a stacked configuration. The pump system 5500 can generally be carried to a desired location. The portions can then be separated to access and use the pump.

FIGS. 56A-56D illustrate another pump system 5600 including a case with handles. The system 5600 includes a first portion 5602 and a second portion 5604 that fold apart to reveal the control unit and vacuum unit and pumping accessories. The first portion 5602 snaps to the second portion 5604. The pump system 5600 can generally be carried to a desired location. The first portion 5602 can then be unsnapped from the second portion 5604 to fold open and use the pump.

FIGS. 57A-57D illustrate another pump system 5700 including a case. The system 5700 includes first and second portions 5702, 5704 that house pumping accessories and a third portion 5706 that houses the control unit and vacuum unit. The third portion 5706 can include a silencer assembly with multiple motors positioned therein. The portions are held in a stacked configuration during transport by a band 5708. The pump system 5700 can generally be carried to a desired location. The band 5708 is then removed so that the portions can be separated to access and use the pump.

FIGS. 58A-58D illustrate another pump system 5800 including a case. The system 5800 includes a first portion 5802 that houses pumping accessories and a second portion 5804 that houses the control unit and vacuum unit. The second portion 5804 can include a silencer assembly with multiple motors positioned therein. The first portion 5802 snaps or is otherwise coupled to the second portion 5804. The pump system 5800 can generally be carried to a desired location. The first portion 5802 can then be separated from the second portion 5804 to access and use the pump.

FIGS. 59A-59D illustrate another pump system 5900 including a case with a handle 5910. The system 5900 includes first and second portions 5902, 5904 that house pumping accessories and a third portion 5906 that houses the control unit and vacuum unit. The third portion 5906 can include a silencer assembly with multiple motors positioned therein. The portions are held in a stacked configuration during transport by the handle 5910. The pump system 5900 can generally be carried to a desired location. The handle 5910 is then removed so that the portions can be separated to access and use the pump.

FIGS. 60A-60D illustrate another pump system 6000 including a case. The system 6000 includes a first portion 6002 holding pumping accessories and a second portion 6004 holding the control unit and vacuum unit. The first portion 6002 snaps to the second portion 6004. The pump system 6000 can generally be carried to a desired location. The first portion 6002 can then be unsnapped from the second portion 6004 to open and use the pump.

Although this detailed description has set forth certain embodiments and examples, the present disclosure extends beyond the specifically disclosed embodiments to other alternative embodiments and/or uses of the embodiments and modifications and equivalents thereof. Thus, it is intended that the scope of the present disclosure should not be limited by the particular disclosed embodiments described above.

What is claimed is:

1. A breast pump system, comprising:
a control unit including an electronic interface to control the breast pump system;
a vacuum unit controlled by the control unit and including a plurality of pump motors to create suction for pumping milk;
a support mechanism located remotely from the control unit; and
a member extending between the control unit and the support mechanism, the member being coupled to the control unit and movable in multiple dimensions to allow the electronic interface of the control unit to be repositioned relative to the support mechanism while being supported by the member;
wherein the member is a conduit, wherein the conduit defines a channel through which one or more of a vacuum line and electrical lines extend between the control unit and the vacuum unit.

2. The system of claim 1, wherein the support mechanism includes a trolley with wheels.

3. The system of claim 2, wherein the trolley forms a vertical pole, and further comprising a clamp that allows the control unit and the vacuum unit to be coupled to the vertical pole at a desired height.

4. The system of claim 3, wherein the control unit is positioned at a first end of the conduit and the vacuum unit is positioned at a second end of the conduit.

5. The system of claim 4, wherein the vacuum unit is sized to counterbalance the control unit.

6. The system of claim 1, further comprising an accessory area formed to hold pumping accessories.

7. A breast pump system, comprising:
a control unit including a processor and memory, the control unit including an electronic interface to control the breast pump system;
a vacuum unit controlled by the control unit, the vacuum unit including a plurality of pump motors to create suction for pumping milk;
a support mechanism located remotely from the control unit; and
a member extending between the control unit and the support mechanism, the member being coupled to the control unit and movable in multiple dimensions to allow the electronic interface of the control unit to be repositioned relative to the support mechanism while being supported by the member;
wherein the memory encodes instructions which, when executed by the processor, cause the breast pump system to:
select at least a first pump motor from the plurality of pump motors for a first pumping timeframe; and
select at least a second pump motor from the plurality of pump motors for a second pumping timeframe, wherein the second pumping timeframe starts at the same time or a time after the first pumping timeframe begins; and
wherein the support mechanism comprises a trolley with wheels, wherein the trolley forms a vertical pole to which the control unit and the vacuum unit are coupled.

8. The system of claim 7, wherein the memory encodes further instructions which, when executed by the processor, cause the pump system to iteratively select between the first pump motor and the second pump motor for each subsequent pumping timeframe.

9. The system of claim 7, wherein the second pumping timeframe starts after one of: a portion of a single pumping cycle by the first pump motor; a single pumping cycle by the first pump motor; a single pumping session by the first pump motor; a malfunction of the first pump motor; and a useful life of the first pump motor.

10. The system of claim 7, further comprising a plurality of solenoids, wherein the memory encodes further instructions which, when executed by the processor, cause the pump system to select a first solenoid of the plurality of solenoids for the first pumping timeframe and a second solenoid of the plurality of solenoids for the second pumping timeframe.

11. A breast pump system, comprising:
a control unit including a processor and memory, the control unit including an electronic interface to control the breast pump system;
a vacuum unit controlled by the control unit, the vacuum unit including a plurality of pump motors to create suction for pumping milk;
a support mechanism located remotely from the control unit; and
a member extending between the control unit and the support mechanism, the member being coupled to the control unit and movable in multiple dimensions to allow the electronic interface of the control unit to be repositioned relative to the support mechanism while being supported by the member;
wherein the memory encodes instructions which, when executed by the processor, cause the breast pump system to:
select at least a first pump motor from the plurality of pump motors for a first pumping timeframe; and
select at least a second pump motor from the plurality of pump motors for a second pumping timeframe, wherein the second pumping timeframe starts at the same time or a time after the first pumping timeframe begins; and
wherein the member is a conduit defining a channel through which one or more of a vacuum line and electrical lines extend between the control unit and the vacuum unit.

12. The system of claim 7, further comprising a clamp that allows the control unit and the vacuum unit to be coupled to the vertical pole at a desired height.

13. The system of claim 7, further comprising an accessory area formed to hold pumping accessories.

14. The system of claim 7, wherein the member is a conduit, and wherein the control unit is positioned at a first end of the conduit and the vacuum unit is positioned at a second end of the conduit.

15. The system of claim 14, wherein the vacuum unit is sized to counterbalance the control unit.

* * * * *